United States Patent
Lukyanov et al.

(10) Patent No.: US 7,803,922 B2
(45) Date of Patent: Sep. 28, 2010

(54) METHODS AND COMPOSITIONS FOR SELECTIVELY CLEAVING DNA CONTAINING DUPLEX NUCLEIC ACIDS IN A COMPLEX NUCLEIC ACID MIXTURE, AND NUCLEASE COMPOSITIONS FOR USE IN PRACTICING THE SAME

(75) Inventors: Sergey A. Lukyanov, Moscow (RU); Denis V. Rebrikov, Moscow (RU); Dmitriy A. Shagin, Moscow (RU)

(73) Assignee: Evrogen JSC, Moscow (RU)

( * ) Notice: Subject to any disclaimer, the term of this patent is extended or adjusted under 35 U.S.C. 154(b) by 376 days.

(21) Appl. No.: 12/012,156

(22) Filed: Jan. 30, 2008

(65) Prior Publication Data

US 2008/0138825 A1    Jun. 12, 2008

Related U.S. Application Data

(60) Division of application No. 10/845,366, filed on May 12, 2004, now Pat. No. 7,435,794, which is a continuation-in-part of application No. PCT/US02/38808, filed on Dec. 3, 2002.

(60) Provisional application No. 60/337,125, filed on Dec. 4, 2001, provisional application No. 60/393,699, filed on Jul. 2, 2002.

(51) Int. Cl.
*C07H 21/02* (2006.01)
*C07H 21/04* (2006.01)
*C12N 15/00* (2006.01)
*C12Q 1/68* (2006.01)

(52) U.S. Cl. .................. 536/23.1; 435/6; 435/320.1

(58) Field of Classification Search .................. None
See application file for complete search history.

(56) References Cited

U.S. PATENT DOCUMENTS

2004/0006033 A1    1/2004    Zhu

OTHER PUBLICATIONS

Chou et al., "Shrimp hepatopancreatic deoxyribonuclease—purification and characterization as well as comparison with bovine pancreatic deoxyribonuclease," Biochim. Biophys. Acta, 1990, 1036(2):95-100.
GenBank Accession No. CAB55635, "Deoxyribonuclease I [*Marsupenaus japonicus*]", Apr. 10, 2000.
Lin et al., "Thermal inactivation of shrimp deoxyribonuclease with and without sodium dodecyl sulfate," Biochim. Biophys. Acta, 1994, 1209(2):209-214.
Menzorova et al., "Isolation and Characterization of Ca2+, Mg2+ -Dependent Endonuclease From Hepatopancreas of the Crab," Biochemistry (Mosc.), 1993, 58(5):681-691.
Menzorova et al., "Highly Stable Ca2+, Mg2+ -Dependent DNase From Crab Hepatopancreas," Biochemistry (Mosc.), 1994, 59:321-325.
Wang et al., "Cloning and characterization of a novel nuclease from shrimp hepatopancreas, and prediction of its active site," Biochem. J, 2000, 346(Pt 3):799-804.

*Primary Examiner*—Teresa E Strzelecka
(74) *Attorney, Agent, or Firm*—Bret E. Field; Bozicevic, Field & Francis LLP

(57) ABSTRACT

Methods of selectively cleaving DNA containing duplex nucleic acids in a complex nucleic acid mixture, as well as nuclease containing compositions for use therein, are provided. In the subject methods, a nuclease or composition thereof is employed to provide for selective cleavage of DNA containing duplex nucleic acids in a complex nucleic acid mixture. Also provided are novel duplex-stranded specific nucleases and nucleic acids encoding the same, where the subject nucleases are enzymes that, preferentially cleave deoxyribonucleic acid molecules in perfectly matched nucleic acid duplexes as compared to non-perfectly matched nucleic acid duplexes of the same length and/or single stranded nucleic acids. The subject methods and compositions for practicing the same find use in a variety of different applications, including, but not limited to, nucleic acid analyte detection applications, gene expression profiling applications, detection of nucleic acid variants including single nucleotide polymorphisms applications, preparation of subtracted and normalized nucleic acid libraries, etc. Finally, kits for use in practicing the subject methods are provided.

5 Claims, 21 Drawing Sheets

| Substrate | Substrate structure | $T_{1/2}$, min |
|---|---|---|
| 20nt-ss | TAMRA-5'-tgggcagtgctcgcttagtg-DABCYL-3' | 406.8±37.0 |
| 7bp-ds | TAMRA-5'-tgggcagtgctcgcttagtg-DABCYL-3'<br>3'-cacgagc-5' | 241.9±39.2 |
| 8bp-ds | TAMRA-5'-tgggcagtgctcgcttagtg-DABCYL-3'<br>3'-cacgagcg-5' | 83.2±15.5 |
| 9bp-ds | TAMRA-5'-tgggcagtgctcgcttagtg-DABCYL-3'<br>3'-tcacgagcg-5' | 20.8±6.15 |
| 10bp-ds | TAMRA-5'-tgggcagtgctcgcttagtg-DABCYL-3'<br>3'-tcacgagcga-5' | 2.4±0.4 |
| 20bp-ds | TAMRA-5'-tgggcagtgctcgcttagtg-DABCYL-3'<br>3'-accgtcacgagcgaatcac-5' | 0.6±0.2 |

B.

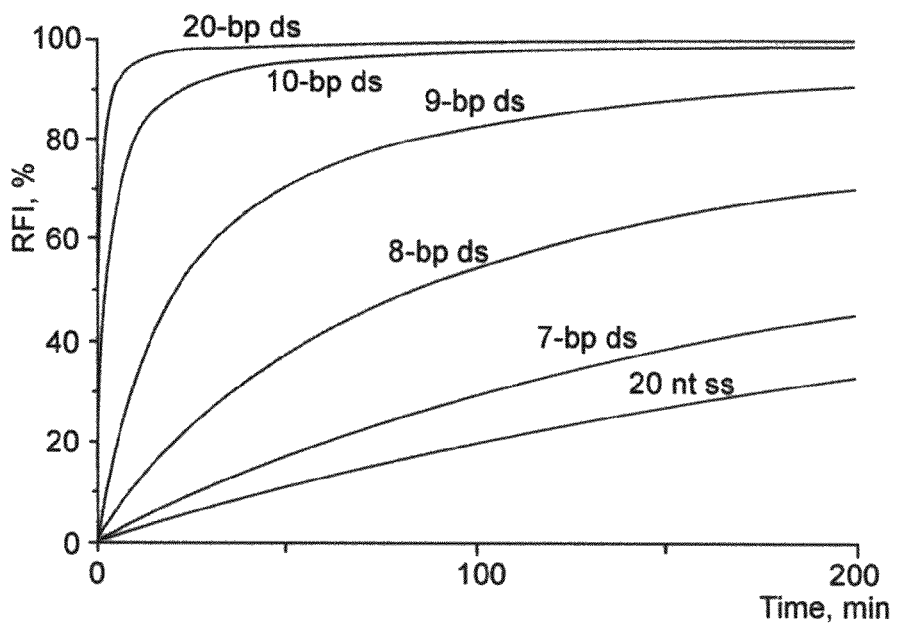

FIG. 10
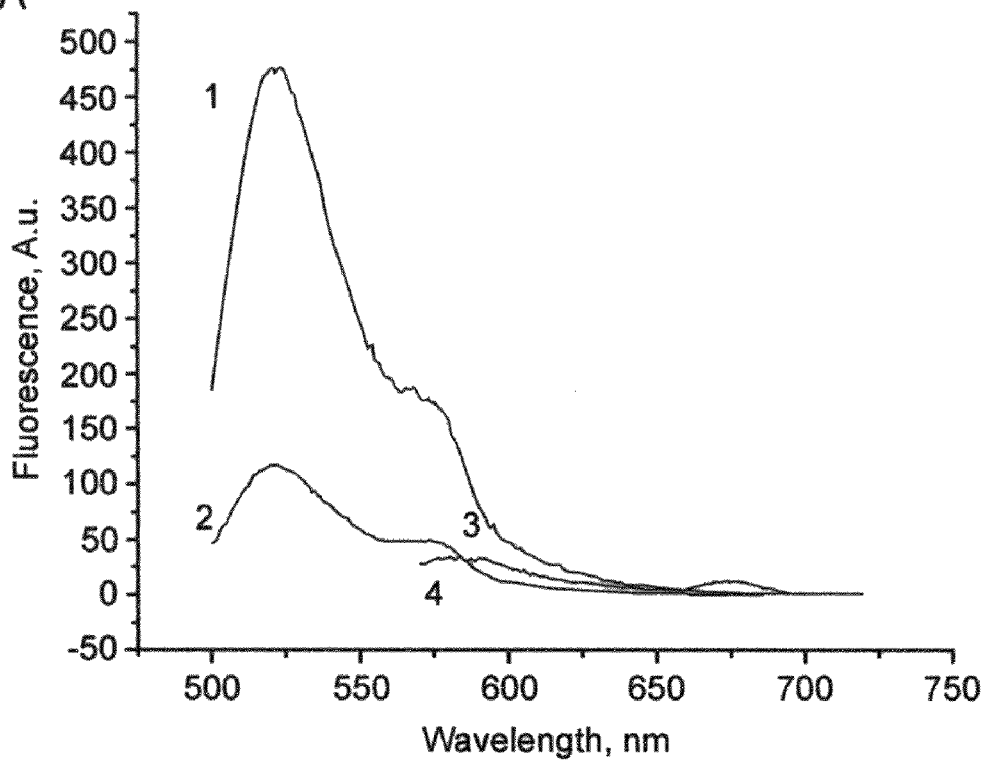
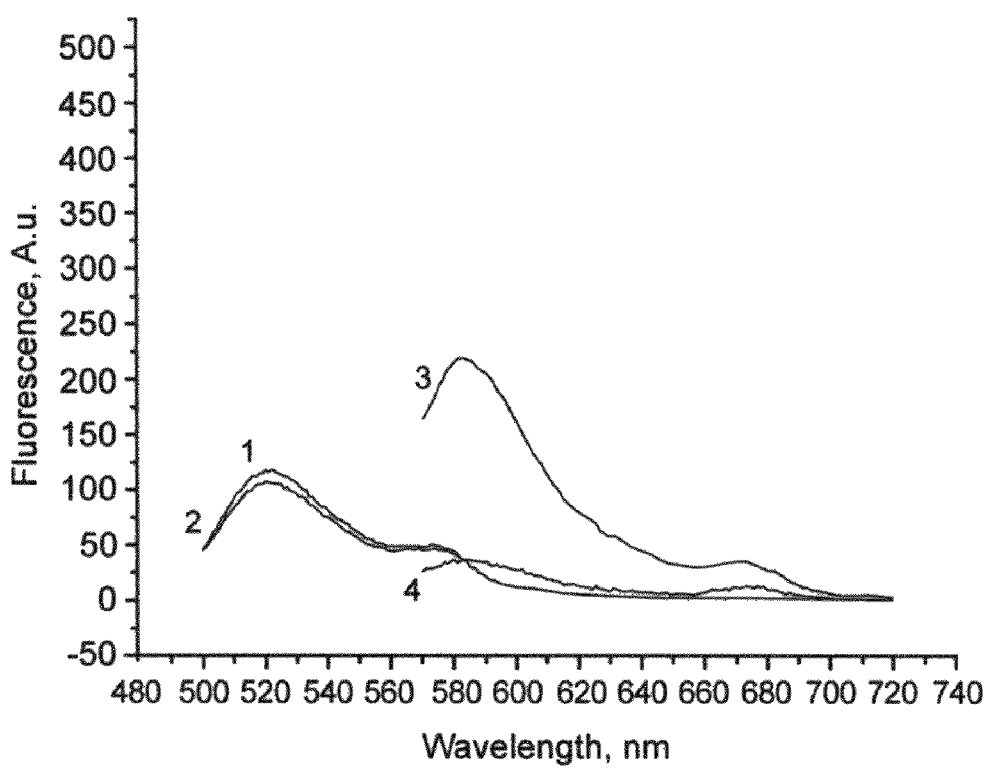

FIG. 15
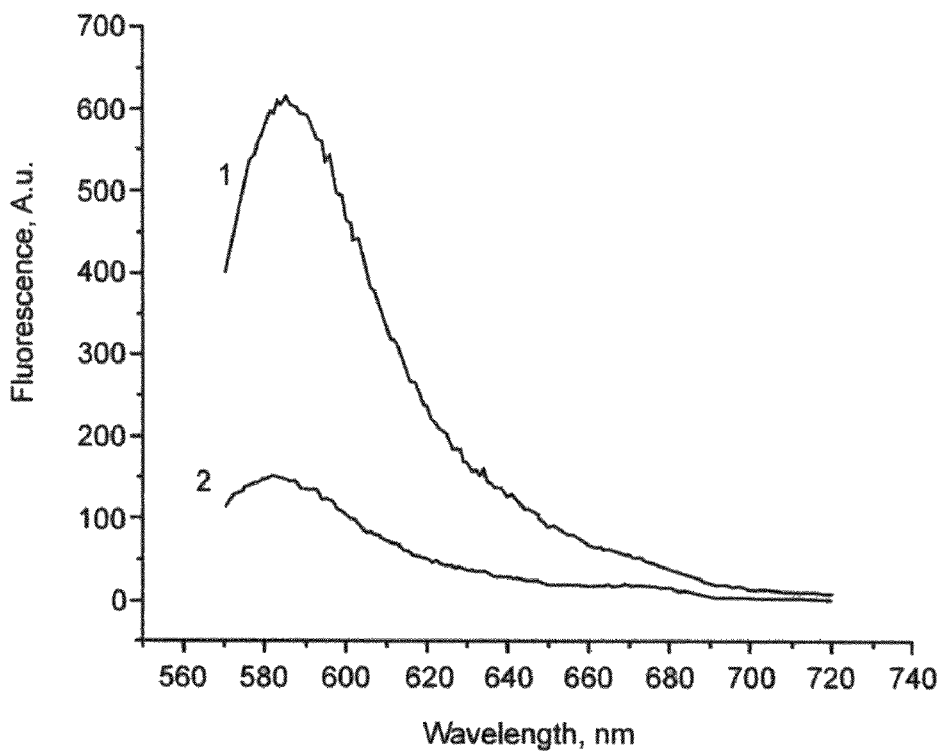
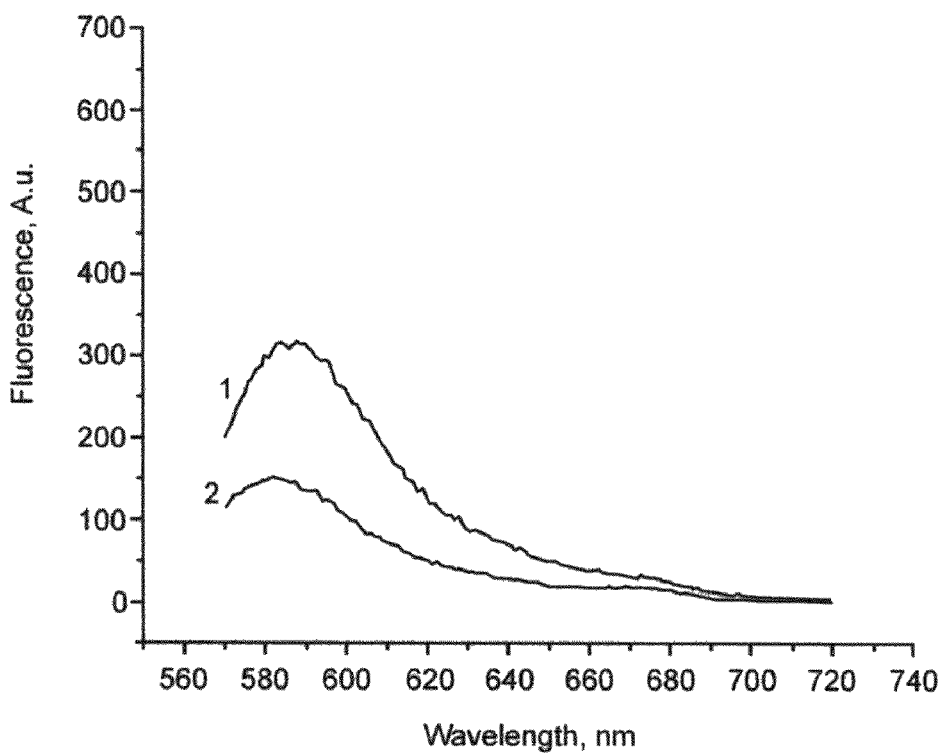

METHODS AND COMPOSITIONS FOR SELECTIVELY CLEAVING DNA CONTAINING DUPLEX NUCLEIC ACIDS IN A COMPLEX NUCLEIC ACID MIXTURE, AND NUCLEASE COMPOSITIONS FOR USE IN PRACTICING THE SAME

CROSS REFERENCE TO RELATED APPLICATIONS

This application is a divisional application of application Ser. No. 10/845,366 filed on May 12, 2004, which application is a continuation-in-part of PCT/US02/38808 filed on Dec. 3, 2002; which application claims priority to the filing date of the U.S. Provisional Patent Application Ser. No. 60/337,125 filed Dec. 4, 2001 and to the filing date of U.S. Provisional Application Ser. No. 60/393,699 filed on Jul. 2, 2002; the disclosures of which are herein incorporated by reference.

INTRODUCTION

1. Field of the Invention

The field of this invention is molecular biology, particularly enzymes and more particularly nucleases.

2. Background of the Invention

Nucleases are enzymes that degrade nucleic acids (e.g., deoxyribonucleic acids, DNA, and ribonucleic acids, RNA) and exist in various biological materials. These enzymes are involved in DNA and RNA metabolism, including degradation, synthesis and genetic recombination of nucleic acids. Several nucleases are digestive enzymes. Nucleases are generally classified into exonucleases and endonucleases according to their mode of action. The former type acts on the terminal of polynucleotide chain of nucleic acid molecule and hydrolyzes the chain progressively to liberate nucleotides, while the latter type cleaves a phosphodiester bond in nucleic acid molecule distributively to produce DNA or RNA fragments or oligonucleotides.

Among other uses, nucleases find use as reagents in a variety of protocols in molecular biology. Because of the ever increasing use of such protocols, there is continued interest in the identification of new nucleases with novel properties. Of particular interest would be the identification of nucleases and compositions thereof that are capable of selectively cleaving DNA containing duplex nucleic acids in a complex nucleic acid mixture, as such compositions could be used in methods of selectively manipulating such duplex nucleic acids and would find use in a variety of different applications in molecular biology and related fields. The present invention satisfies this need.

Relevant Literature

Reviews about nucleases and their applications include: Williams R J. Methods Mol Biol 2001; 160:409-429; Meiss G, Gimadutdinow O, Friedhoff P, Pingoud A M. Methods Mol Biol 2001; 160:3748; Fors L, Lieder K W, Vavra S H, Kwiatkowski R W. Pharmacogenomics 2000 May; 1(2):219-229; Cappabianca L, Thomassin H, Pictet R, Grange T. Methods Mol Biol 1999; 119:427-442; Taylor G R, Deeble J. Genet Anal 1999 February; 14(5-6):181-186; Suck D. Biopolymers 1997; 44(4):405-421; Liu Q Y, Ribecco M, Pandey S, Walker P R, Sikorska M. Ann N Y Acad Sci 1999; 887:60-76; Liao T H. J Formos Med Assoc 1997 July; 96(7):481-487; Suck D. J Mol Recognit 1994 June; 7(2):65-70; and Liao T H. Mol Cell Biochem 1981 Jan. 20; 34(1):15-22.

Articles disclosing nucleases from *Arthropoda* animals include: Menzorova, et al., Biochemistry (Moscow), vol. 58 (1993) (in Russian) pp. 681 to 691; Menzorova, et al., Biochemistry (Moscow), vol. 59 (1994) pp 321 to 325; Chou & Liao; Biochemica et Biophysica Acta, vol. 1036 (1990) pp 95 to 100; Lin et al., Biochemica et Biophysica Acta, vol. 1209 (1994) pp 209 to 214; Wang et al., Biochem. J., vol 346 (2000) pp 799 to 804.

SUMMARY OF THE INVENTION

Methods of selectively cleaving DNA containing duplex nucleic acids in a complex nucleic acid mixture, as well as nuclease containing compositions for use therein, are provided. In the subject methods, a nuclease or composition thereof is employed under conditions sufficient to provide for selective cleavage of DNA containing duplex nucleic acids in a complex nucleic acid mixture. Also provided are novel duplex-specific nucleases (DSN) and nucleic acids encoding the same, where the subject nucleases are enzymes that, under specific cleavage conditions (hereinafter denoted "DSN conditions"), preferentially cleave deoxyribonucleic acid molecules in perfectly matched nucleic acid duplexes as compared to non-perfectly matched nucleic acid duplexes of the same length and/or single stranded nucleic acids. The subject methods and compositions for practicing the same find use in a variety of different applications, including, but not limited to, nucleic acid analyte detection applications, sequence variant detection applications, gene expression profiling applications, preparation of subtracted and normalized nucleic acid libraries, etc. Finally, kits for use in practicing the subject methods are provided.

The file of this patent contains at least one drawing executed in color. Copies of this patent with color drawings will be provided by the Patent and Trademark Office upon request and payment of the necessary fee.

BRIEF DESCRIPTION OF THE FIGURES

FIGS. 4 A and B provide results of crab DSN DNAse activity assay performed on 7, 8, 9, 10, and 20-mer ds-DNA substrates labeled by TAMRA at 5'-end and DABCYL at 3'-end. Fluorescence intensity was measured at 570 nm (with excitation at 550 nm). The relative fluorescence increase in the oligonucleotide substrate, RFI, was defined as described in FIG. 3 (the first sequence shown in FIG. 4A is labelled 20-mer SEQ ID NO 57; the 7, 8, 9, 10 and 20-mer complements are SEQ ID NOs 58-62, respectively).

FIGS. 10 to 14 provide results obtained from assays demonstrating the ability to use a subject nuclease according to the subject invention in a SNP detection application:

FIGS. 10A and B provide results of SNP detection using crab DSN on PCR products, FT7normD (A) and TT79cD (B). Blue line and Red line —FT7normD and TT79cD specific oligonucleotide fluorescence before nuclease treatment, respectively. Black line and Green line—FT7normD and TT79cD specific oligonucleotide fluorescence after nuclease treatment.

FIG. 11. Detection of 7028 C-T SNP in the COX1 gene with the DSNP assay. PCR fragments of 69, 534 and 952 bp comprising 7028 T or 7028 C variants, and pT-Adv plasmids with 69 bp fragment insertions were used in SNP typing with a T variant-specific signal probe. "DSN+"—reaction with crab DSN; "DSN-"—control samples, no enzyme. (A) The multi-well PCR plate was photographed with Olympus SZX12 fluorescent stereomicroscope equipped with a green filter. (B) PCR strips with DSNP results for 69 bp fragments were photographed with Multi Image Light Cabinet (Alpha Innotech Corporation) under UV light.

FIG. 12. Analysis of p53 C309T, prothrombin 20210 G-to-A and MTHFR C677T polymorphous sites in homo- and heterozygous DNA by the DSNP assay (scheme 1). (A) Photographs obtained on the fluorescent stereomicroscope equipped with green (G) and red (R) filters. GR—computer superposition of images obtained with green and red filters. n/n—homozygous DNA samples comprising wild-type sequence variant, n/m—heterozygous DNA samples, m/m—homozygous DNA samples comprising mutant sequence variant. (B) Normalized emission spectra of these samples obtained on a spectrofluorimeter, with excitation at 480 nm (for green fluorescence) and 550 nm (for red fluorescence). Fluorescence values, ΔF, were normalized as described in Table 1. Green line—homozygous DNA samples comprising the wild-type sequence variant, red line—homozygous DNA samples comprising the mutant sequence, blue line—heterozygous DNA samples.

FIG. 13. Analysis of Factor V Leiden polymorphism G1691A in homozygous and heterozygous DNA samples by the DSNP assay. Photograph was obtained on the fluorescent stereomicroscope equipped with green (G) and red (R) filters. GR—computer superposition of images obtained with green and red filters. n/n—homozygous DNA samples comprising wild-type sequence variant, n/m—heterozygous DNA samples, m/m—homozygous DNA samples comprising mutant sequence variant. Non-normalized emission spectra of these samples after DSN cleavage reaction were obtained on a spectrofluorimeter, with excitation at 480 nm (for green fluorescence) and 550 nm (for red fluorescence). Green line—homozygous DNA samples comprising the wild-type sequence variant, red line—homozygous DNA samples comprising the mutant sequence, blue line—heterozygous DNA samples.

FIG. 14. Fluorescence intensity data obtained by DSNP assay on DNA samples containing wild-type and mutant ApoE sequences in different proportions.

FIG. 15 provides results obtained from assays demonstrating the ability to use a subject nuclease according to the subject invention in a nucleic acid analyte detection in RNA sample. (A) reaction with sense RNA. (B) reaction with antisense RNA (negative control). 1—fluorescence of the reaction mixture after crab DSN treatment; 2—probe fluorescence of the reaction mixture without nuclease treatment.

DESCRIPTION OF THE SPECIFIC EMBODIMENTS

Figure 1:
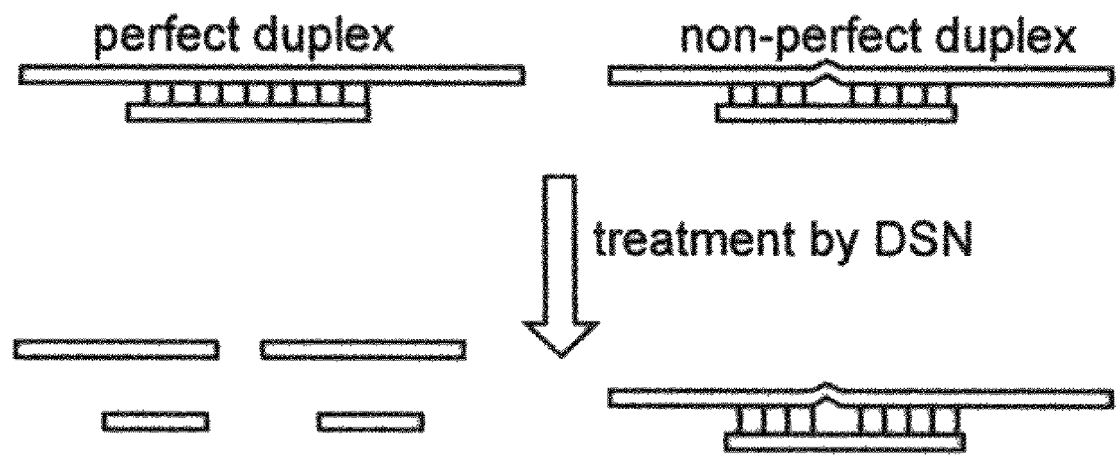
FIG. 1 provides a schematic illustration showing that a novel nuclease (DSN) described in the present application discriminates between short perfect (cleave) and non-perfect (not cleave) DNA-containing duplexes.

Methods of selectively cleaving DNA containing duplex nucleic acids in a complex nucleic acid mixture, as well as nuclease containing compositions for use therein, are provided. In the subject methods, a nuclease or composition thereof is employed under conditions sufficient to provide for selective cleavage of DNA containing duplex nucleic acids in a complex nucleic-acid mixture. Also provided are novel duplex specific nucleases and nucleic acids encoding the same, where the subject nucleases are enzymes that, under "DSN conditions", preferentially cleave deoxyribonucleic acid molecules containing perfectly matched nucleic acid duplexes as compared to non-perfectly matched nucleic acid duplexes of the same length and/or single stranded nucleic acids. The subject methods and compositions for practicing the same find use in a variety of different applications, including, but not limited to, nucleic acid analyte detection applications, sequence variant detection applications including detection of a single nucleotide polymorphisms (SNPs), gene expression profiling applications, detection of a specific PCR products, preparation of subtracted and normalized nucleic acid libraries, etc. Finally, kits for use in practicing the subject methods are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

In further describing the subject invention, the subject methods of selectively cleaving DNA containing duplex nucleic acids are described first in greater detail. Next, the novel nucleases which find use in the subject methods and nucleic acid compositions encoding the same, as well as methods for producing the subject nucleases, antibodies specific therefore and methods for the generation thereof are fully described. Finally, kits that include the subject nucleases are reviewed.

Methods of Selectively Cleaving DNA Containing Duplex Nucleic Acids

As summarized above, the subject invention provides methods of selectively cleaving DNA containing duplex nucleic acids in a complex nucleic acid mixture. By "selectively cleaving" is meant that the subject methods preferentially cut or digest, i.e., cleave, deoxyribonucleic acid molecules present in double-stranded nucleic acids, e.g., DNA-DNA duplexes and DNA-RNA duplexes. In many embodiments, the subject methods are methods of preferentially cleaving perfectly matched duplex nucleic acids. In other words, the subject methods provide for preferential cleavage of perfectly matched duplex nucleic acids, i.e., hybrid structures between perfectly complementary strands where no mismatches are present, as compared to non-perfectly matched nucleic acid duplexes of the same length. As such, when practicing the subject methods on a complex nucleic acid mixture (where the term "complex nucleic acid mixture" refers to a sample that includes two or more different types of nucleic acids, e.g., single and double stranded nucleic acids, RNA and DNA, etc.), perfectly matched DNA containing duplex nucleic acids are cleaved to a much greater extent than non-perfectly matched nucleic acid duplexes, non-DNA containing nucleic acid duplexes and/or single-stranded nucleic acids. In other words, the subject methods are able to cleave or cut target DNA containing duplex nucleic acids in a sample at a much greater rate than other nucleic acids that may be present in the sample being treated, where the rate of target DNA containing duplex nucleic acid cleavage is typically at least about 5 fold, usually at least about 10 fold and more usually at least about 50 fold, such as about 100 fold, greater than the rate of cleavage of other nucleic acids that may be present in the sample being treated.

In many embodiments, the DNA containing nucleic acid duplexes that are cleaved by the subject methods are DNA-DNA duplexes that include a stretch of perfectly matched complementary nucleic acids of at least about 8 bp long, in certain embodiments at least 9 bp long. In other embodiments, the DNA containing nucleic acid duplexes that are cleaved by the subject methods are DNA-RNA duplexes that include a stretch of perfectly matched complementary nucleic acids of at least about 13 bp long, in certain embodiments at least 15 bp long.

As the subject methods preferentially cleave-DNA in double-stranded nucleic acids, the subject methods result in substantially no cleavage activity with respect to single-stranded nucleic acids. As such, when a sample is treated according to the subject methods, the amount of DNA containing double-stranded or duplex nucleic acids that is cleaved in a complex nucleic acid mixture far exceeds the amount of single-stranded nucleic acids that is cleaved in the mixture, e.g., by at least about 5 fold, usually at least about 10 fold and more usually by at least about 50 fold, as measured using the cleavage activity assays briefly summarized below:

1. DSN activity on λ ds DNA and phage M13 ss-DNA is compared by agarose gel electrophoresis. The reaction is performed in a total volume of 10 μl comprising 1×DSN buffer (7 mM $MgCl_2$, 50 mM Tris-HCl, pH 8.0), 0.6 Kunitz units DSN, 150 ng λ DNA and 50 ng M13 DNA. To prevent ds structure formation in phage M13 DNA, the reaction mixture is incubated with active enzyme at 70° C. for 1, 5 or 5 min. The digestion products are visualized on a 0.9% agarose gel following ethidium bromide staining.

2. To compare cleavage rate of the nuclease enzyme on ds and ss DNA, synthetic oligonucleotide substrates are used. Oligonucleotides labeled with a fluorescent donor at the 5' end and a fluorescent quencher at the 3' end are used as ss DNA. To generate ds substrates, labeled oligonucleotides are mixed with equimolar amounts of complementary non-labeled oligonucleotides. Probes are prepared on ice. The cleavage reaction is performed in a total volume of 20 μl comprising 1×DSN buffer, 0.6 Kunitz units DSN, and 0.3 μM oligonucleotide substrate. The reactions are carried out several times (from 1 sec to 100 h) at 35° C. DNase activity is evaluated by estimating the change in fluorescence intensity of the reaction mixture during incubation with DSN. Fluorescence intensity is measured on a spectrofluorimeter Cary Eclypse (Varian) in 2 ml dishes. Cleavage curves are plotted to obtain half-time for substrate cleavage. Half-times of the cleavage for ds DNA and ss DNA were then compared.

RNase activity is measured essentially as described by Ho et al. (Ho H C., Shiau P. F., Liu F. C., Chung J. G., Chen L. Y. 1998. Purification, characterization and complete amino acid sequence of nuclease C1 from *Cunninghamella echinulata* var. *echinulata*. Eur J Biochem. 256: 112-118). The reaction mixture (20 μl) contains 50 mM Tris-HCl (pH 8.0), 5 mM $MgCl_2$, and 0.6 Kunitz units of DSN. After warming the mixture at 55° C. for 5 min, freshly prepared RNA (1.2% mass/vol., Baker's yeast, Sigma) is added and the incubation continued for 1 h. Following incubation, 0.1 volumes of ammonium acetate (7.5 M) and 3 volumes of 96% ethanol are added. The entire solution is mixed and centrifuged. The supernatant is diluted five-fold with water and absorbance at 260 nm is determined.

As indicated above, the subject methods are methods of selectively or preferentially cleaving deoxyribonucleic acid (DNA) molecules in double-stranded nucleic acids. As such, the subject methods are methods of selectively cleaving DNA in DNA-DNA duplexes, as well as DNA/RNA hybrid duplexes. Therefore, when a sample is treated according to the subject methods, DNA in DNA containing duplexes are cleaved at a rate that exceeds the rate of cleavage of any other duplex nucleic acids (e.g., RNA in RNA-RNA and RNA-DNA duplex nucleic acids) that may be present in the complex mixture being treated, in many embodiments by at least about 5 fold, usually at least about 10 fold and more usually by at least about 50 fold, as measured using the cleavage activity assays described above. The ribo- and deoxyribo-synthetic FRET-labeled oligonucleotides of different length described herein may be used to prepare DNA-DNA, RNA-DNA and RNA-RNA substrates in these assays.

Another feature of the subject methods is that they are methods of preferentially cleaving perfectly matched DNA containing duplex nucleic acids (DNA-DNA or DNA-RNA). As such, when a sample is treated according to the subject methods, completely matched DNA containing duplexes or complexes are cleaved at a rate that is at least about 5 fold, usually at least about 10 fold and more usually at least about 50 fold greater than the rate at which non-completely matched DNA containing complexes (that include at least one bp mismatch) are cleaved, as measured using the cleavage activity assay with fluorescently labeled oligonucleotide substrates described above. To prepare nuclease substrates, labeled oligonucleotides may be mixed with non-labeled oligonucleotides to form non-completely and completely matched duplexes. A schematic diagram of the discrimination of the completely matched DNA containing complexes from non-completely matched complexes using the subject nucleases is provided in FIG. 1.

In many embodiments, the discrimination between completely matched and non-completely matched DNA containing nucleic acid duplexes that are cleaved by the subject methods occurs when these duplexes are DNA-DNA duplexes of at least about 8 bp long, in certain embodiments from 9 to 15 bp long and most usually 10 bp long. In other embodiments, the discrimination between completely matched and non-completely matched DNA containing nucleic acid duplexes that are cleaved by the subject methods occurs when these duplexes are DNA-RNA duplexes of at least about 12 bp long, in certain embodiments from 13 to 25 bp long and most usually 15 bp long.

In practicing the subject methods, a sample to be treated according to the subject methods is contacted with an appropriate nuclease to provide for the selective cleavage of DNA in DNA containing duplex nucleic acids, as described above.

The subject methods are practiced on nucleic acid samples, i.e., samples that include nucleic acids. The samples may be obtained from a variety of different sources, depending on the particular application being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans, and the like. Particular samples of interest include biological fluids, e.g., blood, plasma, tears, saliva, urine, tissue samples or portions thereof, cells (including cell linear, cell lines, cell cultures etc) or lysates thereof, etc. The sample may be used directly from its naturally occurring source and/or preprocessed in a number of different ways, as is known in the art.

In some embodiments, the sample is treated to provide for linear nucleic acids in the sample, where a number of protocols are known in the art, e.g., mechanical shearing, restriction enzyme digest, etc. In some embodiments, the sample may be from a synthetic source. In many embodiments, the nucleic acids may be amplified using the methods known in the art like PCR etc. The PCR methods used in the methods of the present invention are carried out using standard methods (see, e.g., Ausubel et al., Current Protocols in Molecular Biology, John Wiley and Sons, New York, 1989; Erlich, PCR Technology, Stockton Press, New York, 1989; Innis et al., PCR Protocols: A Guide to Methods and Applications, Academic Press, Harcourt Brace Javanovich, New York, 1990; Sambrook et al., Molecular Cloning: A Laboratory Manual, Cold Spring Harbor Laboratory Press, Cold Spring Harbor, N.Y., 1989; Barnes, W. M. (1994) Proc Natl Acad Sci USA, 91, 2216-2220). The primers and oligonucleotides used in the methods of the present invention are preferably DNA, and can be synthesized using standard techniques.

In some embodiments, the nucleic acid sample of interest is contacted with synthetic oligonucleotides to form DNA-containing duplexes. In certain embodiments, these synthetic oligonucleotides are labeled with labels known in the art as described in detail below, e.g., these synthetic oligonucleotides are labeled with a fluorescent donor and acceptor (or quencher) pair. In some embodiments, these synthetic oligonucleotides are probe oligonucleotides used to detect sequence or sequence variant in nucleic acid(s) in a sample. In this case, each probe oligonucleotide can form a perfectly matched duplex with a sequence or sequence variant to be detected.

As indicated above, in practicing the subject methods, the sample to be treated is contacted with a sufficient amount of an appropriate nuclease under conditions that provide for the selective DNA cleavage in a DNA containing duplex nucleic acid, i.e., "DSN conditions." A variety of different nucleases may exhibit the specific properties described above under specific cleavage conditions and thus may be employed at least in some of the subject methods.

Representative nucleases of interest include but are not limited to: cation-dependent endonucleases from different sources including DNAase K from Kamchatka crab (Menzorova, et al., Biochemistry (Moscow), vol. 58 (1993) (in Russian) pp. 681 to 691; Menzorova, et al., Biochemistry (Moscow), vol. 59 (1994) pp 321 to 325), Ca,Mg dependent endonuclease from sea-urchin (Menzorova, N. I., Rasskazov, V. A. Biokhimiia (Rus) 1981; vol 46 pp 872 to 880), and members of the family of DNA/RNA non-specific nucleases like shrimp nuclease (Chou & Liao; Biochemica et Biophysica Acta, vol. 1036 (1990) pp 95 to 100; Lin et al., Biochemica et Biophysica Acta, vol. 1209 (1994) pp 209 to 214; Wang et al., Biochem. J., Vol 346 (2000) pp 799 to 804) and the like. Of particular interest in many embodiments are the duplex-specific nucleases, including the novel nucleases, described below.

In practicing the subject methods, the sample is contacted with a sufficient amount of the nuclease being employed under DSN conditions and is maintained for an amount of time sufficient to provide for the desired amount of selective cleavage of DNA in duplex nucleic acids. The amount of nuclease employed will vary depending on the specific nuclease that is employed. However, in many embodiments, the amount of nuclease that is employed is one that is from about 5 Kunitz-units/ml to about 80 Kunitz-units/ml, usually from about 20 Kunitz-units/ml to about 75 Kunitz-units/ml and more usually from about 25 Kunitz-units/ml to about 70 Kunitz-units/ml.

In these embodiments, the amount of nuclease employed will vary proportionally as the reaction volume varies. For example, where the actual reaction mixture is double the exemplary reaction mixture provided above, the amount of nuclease that is employed is, in certain embodiments, double the exemplary amounts provided above, or is some other proportional amount thereof.

In practicing the subject methods, the temperature of the reaction mixture is typically one that ranges from about 10° C. to about 0.70° C., usually from about 15° C. to about 65° C., more usually from about 20° C. to about 60° C. In some embodiments the temperature is a temperature in which DNA, to be cleaved, forms duplexes. In some embodiments the temperature is changed during cleavage reaction. For example, at the first stage of the cleavage reaction, the temperature is optimal for fragmentation of a sample nucleic acids to short oligonucleotides by subject nuclease (temperature of fragmentation) and at the second stage, the temperature is optimal for hybridization of sample nucleic acids with probe oligonucleotides and sufficient for cleavage of all perfectly matched duplexes generated by target sample nucleic acids and probe oligonucleotides (annealing temperature).

The subject nucleases are employed under conditions (noted as DSN conditions) where these conditions ensure specific cleavage of nucleic acid substrates, as described above. In certain embodiments, "DSN conditions" are conditions in which $Mg^{2+}$ is present. In these embodiments of DSN conditions, the $Mg^{2+}$ concentration can range from about 2 to about 15, where the optimal $Mg^{2+}$ conditions range from about 3 to about 12, usually from about 4 to about 10 and more usually from about 5 to about 8 mM.

Under certain DSN conditions, the pH typically ranges from about 5 to about 10, usually from about 7 to about 8.5. In practicing the subject methods, the reaction mixture containing the sample of nucleic acids and the nuclease is typically maintained under DSN conditions for a period of time ranging from about 1 min to about 48 h, usually from about 10 min to about 24 h and more usually from about 20 min to about 2 h.

In practicing the subject methods, the manner in which the various reagents are contacted with the sample may vary. As such, in certain embodiments, the nuclease may be introduced into the sample after than the introduction of any other reagents, e.g., $Mg^{2+}$. In alternative embodiments, all of the reagents are combined at the same time. In some embodiments, the nuclease may be introduced into the sample before than the introduction of some other reagents, e.g., probe oligonucleotides. The manner in which contact or combination is achieved may vary, e.g., by introducing nuclease into the sample, by introducing an amount of sample in a nuclease containing medium, etc.

The subject methods are useful in a number of applications in the field of genetic analysis. More specifically, the subject methods are useful in methods for detection and characterization of nucleic acid sequences. In particular, the subject methods find use in applications where one wishes to selectively manipulate, e.g., process, detect, eliminate etc., DNA containing duplexes in the presence of one or more other types of nucleic acids, i.e., in a complex nucleic acid mixture. As such, the subject methods find use in a variety of different applications.

In one type of application, DNA containing perfectly matched duplex nucleic acids is distinguished from other types of nucleic acids that are present in a complex nucleic acid mixture. In these applications, perfectly matched duplex nucleic acids that include at least one deoxyribonucleic acid molecule are distinguished from non-perfectly matched duplex nucleic acids of the same length and from single stranded nucleic acids. Specific representative applications of this first category of applications include methods of detecting nucleic acid sequences of interest in a sample and methods of detecting nucleic acid sequence changes in a sample. In another type of application, the subject methods are employed to selectively remove DNA containing duplex nucleic acids from a sample, e.g., by digestion of such duplex nucleic acids, so as to enrich the sample for nucleic acids that are other than DNA containing duplex nucleic acids, e.g., to enrich for single stranded nucleic acids, e.g., single stranded DNA, single stranded RNA, etc. Specific representative applications of this second category include methods for construction of subtractive and/or normalized (also denoted as equalized) nucleic acids libraries.

Representative applications of interest include, but are not limited to: methods of detection a nucleic acid analyte(s) of interest in a sample (e.g., methods of identifying bacterial and viral strain nucleic acid analytes and specie specific nucleic acid analytes in a sample; methods of expression analysis, methods of the detection of the specific PCR product(s), etc.); methods of detection of nucleic acid variants including single nucleotide polymorphisms (SNPs); methods of nucleic acid sequencing; and methods of equalization and subtractive hybridization of nucleic acid samples. Each of these specific applications employing the subject methods are now described in greater detail below.

Methods of Detection of the Sequence(s) and Sequence Variants

The subject methods find use in applications of detection of sequences or sequence variants in nucleic acid samples. These methods include, but are not limited to: methods of identifying a nucleic acid analyte in a sample (e.g., methods of identifying bacterial and viral strain nucleic acid analytes and species specific nucleic acid analytes in a sample; methods of expression analysis, methods of the detection of the specific PCR product(s), etc.); methods of detection of nucleic acid variants including single nucleotide polymorphisms (SNPs); and methods of nucleic acid sequencing.

In the subject methods, the nucleic acid sample to be tested is contacted with a subject nuclease (e.g., DSN) and with a set of the labeled short synthetic probe oligonucleotides, that produce perfectly matched duplexes with different sequences or sequence variants to be detected. During incubation, perfectly matched duplexes between the nucleic acid sample and probe oligonucleotide are cleaved by the DSN to generate a sequence-specific signal.

In using the subject methods, the nucleic acid sample to be tested is first obtained. As such, the first step in the subject methods is to obtain a nucleic-acid sample.

The sample may be obtained from a variety of different sources, as noted above. The sample may be used directly from its naturally occurring source and/or preprocessed in a number of different ways, as is known in the art. Depending on the particular application of interest, nucleic acids in the sample may be RNA, double stranded DNA or single stranded DNA and may be exist in linear as well as circular forms.

In some embodiments, the sample is treated to provide for linear nucleic acids in the sample, where a number of different protocols are known for linearizing nucleic acids, e.g., mechanical shearing, restriction enzyme digest, etc. In some embodiments, the sample may be from a synthetic source. In some-embodiments, if the sample is RNA sample, the prior step is first strand cDNA preparation that is performed by any method known in the art. Depending on the particular interest and the amount of the starting material, the preparation of amplified DNA might is then performed. In other embodiments, nucleic acid sample is RNA that is used directly from its naturally occurring source or synthesized (for example synthesized from T7 promoter-containing PCR amplified DNA by known methods).

In certain embodiments, to decrease the complexity of the nucleic acids in the sample, amplification of the fraction that is enriched of the nucleic acid sequences to be tested is performed, e.g., by PCR or other methods known in the art. In certain embodiments, specific PCR primers are used to amplify nucleic acids of interest. In other embodiments, adapter-specific PCR primers are used to amplify nucleic acid sample. In each case, PCR primers are constructed to amplify nucleic acid fragments that comprise the site for annealing of probe oligonucleotides. In other embodiments, the DNA sample is used without amplification.

Thus, in certain embodiments, nucleic acids to be tested are unpurified PCR products. In other embodiments, nucleic acids to be tested are non-amplified DNA and RNA. In some embodiments, nucleic acids to be tested are exposed to purification using methods known in the art and ethanol precipitation (with following resolution in DSN buffer). In certain embodiments, the nucleic acids to be tested may vary is size, but typically range in size from about 10 to about 4000 bp (nucleotide base pairs) long, and in certain embodiments these nucleic acids range in length from about 50 to about 1000 bp long, such as from about 60 to about 500 bp long. After the sample is obtained, the nucleic acids of the sample are contacted with subject nuclease and with a set of one or more probe oligonucleotides.

The set of probe oligonucleotides may include a separate probe oligonucleotide for each nucleic acid sequence or sequence variant to be detected. As such, where one is assaying a sample for a single nucleic acid sequence variant, the set of probe oligonucleotides employed may include a single probe oligonucleotide. In other embodiments where one is assaying for two (or more) different nucleic acid sequence variants, the set may include a different probe oligonucleotide for each of the nucleic acid sequences to be detected. The probe oligonucleotides are DNA in many embodiments. In addition, they may be single-stranded linear molecules. The probe oligonucleotides may be labeled with a detectable label.

Suitable labels include, but are not limited to: fluorescent labels, isotopic labels, enzymatic labels, particulate labels, etc. For example, suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), cyanine dyes, e.g. Cy5, Cy3, BODIPY dyes, e.g. BODIPY 630/650, Alexa542, etc. Suitable isotopic labels include radioactive labels, e.g. $^{32}P, ^{33}P, ^{35}S, ^{3}H$. Other suitable labels include size particles that possess light scattering, fluorescent properties or contain entrapped multiple fluorophores. The label may be a two stage system, where the target DNA is conjugated to biotin, haptens, etc. having a high affinity binding partner, e.g. avidin, specific antibodies, etc. the binding partner is conjugated to a detectable label, e.g. an enzymatic label capable of converting a substrate to a chromogenic product, a fluorescent label, and isotopic label, etc.

Of particular interest in many embodiments are oligonucleotide probes that are fluorescence labeled with two or more different fluorophores that are placed in different locations on the probe such that a different signal is observed depending on whether the probe is or is not cleave into two or more pieces such that the different positioned fluorophores are separated from each other. Examples of such fluorescent labels include, but are not limited to: non-FRET fluorescence quenching labels, as described in: (1) U.S. Pat. No. 6,150,097 (fluorescer-quencher pairs, where fluorescers of interest include Fluorescein, Lucifer Yellow, BODIPY, Eosine, Erythrosine, Tetramethyl-rhodamine, Texas Red and Coumarin and quenchers of interest include: DABCYL, DABMI and Malachite Green); the disclosure of which is herein incorporated by reference; (2) self-quenching fluorescent probes, as described in U.S. Pat. No. 6,030,787 (reporter-quencher pairs may be selected from xanthene dyes, including fluoresceins, and rhodamine dyes; naphthylamines, e.g., 1-dimethylaminonaphthyl-5-sulfonate, 1-anilino-8-naphthalene sulfonate and 2-p-touidinyl-6-naphthalene sulfonate; 3-phenyl-7-isocyanatocoumarin, acridines, such as 9-isothiocyanatoacridine and acridine orange; N-(p-(2-benzoxazolyl)phenyl)-maleimide; benzoxadiazoles, stilbenes, pyrenes, and the like); and; (3) molecular energy transfer probes, as described in U.S. Pat. No. 6,117,635 (where specific fluorophores of interest listed in the patent include: 4-acetamido-4'-isothiocyanatostilbene-2,2'disulfonic acid; acridine and derivatives, e.g., acridine, acridine isothiocyanate, 5-(2'-aminoethyl)aminonaphthalene-1-sulfonic acid (EDANS), 4-amino-N-[3-vinylsulfonyl)phenyl]naphthalimide-3,5, disulfonate (Lucifer Yellow VS), N-(4-anilino-1-naphthyl)maleimide, anthranilamide, Brilliant Yellow, coumarin and derivatives, e.g., coumarin, 7-amino-4-methylcoumarin (AMC, Coumarin 120), 7-amino-4-trifluoromethylcoumarin (Coumarin 151), cyanosine, 4'-6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylenetriamine pentaacetate, 4-(4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), eosin and derivatives, e.g., eosin, eosin isothiocyanate, erythrosin and derivatives, e.g., erythrosin B, erythrosin isothiocyanate, ethidium, fluorescein and derivatives, e.g., 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate, QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene and derivatives, e.g., pyrene, pyrene butyrate, succinimidyl 1-pyrene butyrate, Reactive Red 4 (Cibacron® Brilliant Red 3B-A), rhodamine and derivatives, e.g., 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives); the disclosure of which is herein incorporated by reference. In these embodiments, the two or more different moieties that make up the detectable label, e.g., the fluorophore moieties, the fluorophore/quencher moieties, etc., are spaced relative to each other to provide for the specific properties desired, as is known in the art, where the spacing required is readily determined by those of skill in the art in view of the above specifically cited patents.

The amount of sample nucleic acids in the reaction mixture may vary but typically ranges from 1 mkg/ml to 40 mkg/ml, usually from 2 mkg/ml to 5 mkg/ml. The amount of probe oligonucleotides that is contacted with the sample may vary, but typically ranges from about 0.1 mkM to about 1 mkM, usually from about 0.2 mkM to about 0.3 mkM for each target nucleic acid to be detected.

If the nucleic acid sample to be tested is a DNA, the probe oligonucleotides that are contacted with the sample typically range in length from about 8 to about 60 nucleotides, usually from about 9 to about 25 nucleotides and more usually from about 10 to about 15 nucleotides.

In some embodiments, nucleic acid in the sample is RNA. If the nucleic acid sample to be tested is RNA, the probe oligonucleotides that are contacted with the sample typically range in length from about 13 to about 60 nucleotides, usually from about 14 to about 45 nucleotides and more usually from about 15 to about 25 nucleotides.

The buffer where reaction with the subject nucleases (in certain embodiments, crab DSN) is performed is sufficient to provide for cleavage of DNA-containing perfectly matched duplexes and will vary depending on the specific nuclease that is employed. In certain embodiments, the buffer contains $Mg^{2+}$ in final concentration from 2 to about 15 mM, more usually from about 6 to about 8 mM. The pH typically ranges from about 6 to about 10, usually from about 7 to about 8.5.

The amount of the nuclease that is contacted with the nucleic acid sample is sufficient to provide for cleavage of ds-DNA containing substrates present or generated in the reaction mixture and will vary depending on the specific nuclease that is employed. In certain embodiments, the amount of enzyme typically ranges 5 Kunitz-units/ml to about 80 Kunitz-units/ml, usually from about 20 Kunitz-units/ml to about 75 Kunitz-units/ml and more usually from about 25 Kunitz-units/ml to about 70 Kunitz-units/ml.

In some embodiments, the nucleic acid sample is first contacted with the subject nuclease and the resultant mixture is then maintained at temperature optimal for DSN cleaving for a period of time sufficient to provide for partial cleavage of ds-DNA and generation of short DNA fragments (on average from about 7 to about 20 nt long). The temperature of this stage (temperature of fragmentation) is usually from about 50 to about 65° C., more usually from about 55 to about 60° C. The incubation period may vary but typically ranges from about 10 to abpit 30 min.

After this step, the probe oligonucleotide(s) is added, and the resultant mixture is maintained at a temperature sufficient to provide the formation of duplexes between probe oligonucleotides and digested target nucleic acids. The digestion of the perfectly matched duplexes generated occurs at the same time. Temperature conditions employed in this step (annealing temperature) depend, at least in part, on the oligonucleotide length and composition, as is known in the art. The temperature typically ranges from about 20 to about 72° C., usually from about 25 to about 68° C., and most usually from about 30 to about 40° C. The probe oligonucleotide(s) is contacted with the reaction mixture either before, during or after temperature change. In certain embodiments, the nucleic acid sample is contacted with the probe oligonucleotides and the subject nuclease at the same time, and resultant mixture is maintained first at temperature of fragmentation and then at the annealing temperature.

In some embodiments, the step of incubation at a temperature of fragmentation is excluded from the protocol. In this case, the nucleic acid sample is contacted with the probe oligonucleotide(s) and the subject nuclease the same time, and the resultant mixture is maintained at the annealing temperature for a period of time sufficient for cleavage of any perfectly matched DNA-containing nucleic acids present (or generated) in the reaction mixture by the subject nuclease.

During incubation, the subject nuclease cleaves the ds DNA containing sample nucleic acids (e.g., PCR products) to generate short DNA fragments that can effectively hybridize with probe oligonucleotides. All perfectly matched duplexes generated by the DNA template and probe oligonucleotides are also cleaved by the subject nuclease. In this case the temperature conditions typically range from about 20 to about 72° C., usually from about 25 to about 68° C., and most usually from 30 to about 40° C. The reaction mixture, including the active enzyme, is typically maintained for a period of time ranging from about 30 min to about 48 hrs, usually from about 2 h to about 24 hrs.

In some embodiments, the cleavage reaction described above is performed in the presence of exonuclease-deficient Klenow fragment (KF(exo-)), which catalyzes strand displacement DNA synthesis by extension of the 3'-ends generated in the PCR fragment upon nicking activity of the subject nuclease. Displaced DNA strands are involved in a reaction with probe oligonucleotides that results in about 5-20 times increase in the specific signals generated during probe oligonucleotide cleaving. In this case the temperature conditions typically range from about 20 to 40° C., usually from about 30 to about 37° C., and most usually from 33 to 35° C. The reaction mixture, including the active enzyme, is typically maintained for a period of time ranging from about 30 min to about 12 hrs, usually from about 1 h to about 2 hrs.

In some embodiments, the nucleic acid sample being treated or assayed is processed, e.g., heated, to destroy the secondary structures that are present among the nucleic acids of the sample. In this case, the sample is contacted with the set of probe oligonucleotides and subjected to dissociation and annealing conditions. The order in which the dissociation and contacting occurs may be varied, so long as the probe oligonucleotides are combined with the dissociated nucleic acids of the sample prior to the annealing step. As such, the probe nucleic acids may be contacted with the sample prior to dissociation in certain embodiments. In other embodiments, the probe nucleic acids may be contacted with the sample after dissociation but before annealing. The manner in which the probe oligonucleotides are contacted with the sample may vary, where representative protocols including pipette introduction, etc. To denature or dissociate the secondary structures present in nucleic acids in the sample, including the duplex target nucleic acids present therein, the sample is heated to an elevated temperature and the heated sample is maintained at the elevated temperature for a period of time sufficient for any double-stranded or hybridized nucleic acids present in the reaction mixture to dissociate. For denaturation, the temperature of the reaction mixture will usually be raised to, and maintained at, a temperature ranging from about 85 to 100° C., usually from about 90 to 98° C. and more usually from about 93 to 96° C. for a period of time ranging from about 1 to 200 sec or more, often from about 3 to 120 sec, usually from about 5 to 60 sec.

Next, the dissociated nucleic acids in the sample are allowed to reanneal in the presence of the probe oligonucleotides, which have been contacted with the sample either before, during or after dissociation. The resultant reaction mixture is then subjected to conditions sufficient for probe annealing to template complementary nucleic acid present in the mixture. The temperature to which the reaction mixture is lowered to achieve these conditions will usually be chosen to provide optimal efficiency and specificity, and will generally range from about 20 to about 72, usually from about 25 to 68° C., where the specific temperature conditions employed depend, at least in part, on the oligonucleotide length, as is known in the art. Annealing conditions may be maintained for a period of time ranging from about 15 sec to overnight or longer.

Following this annealing step (or during the annealing step—in certain embodiments, the steps of annealing and digestion are united), the reaction mixture is contacted with the subject nuclease under DSN conditions (as described above) for a period of time sufficient for the double-stranded DNA containing substrates present in the sample, which substrates include perfectly matched duplexes of target nucleic acids and oligonucleotide probes, to be cleaved by the enzyme.

At the end of the incubation period, the activity of the nuclease enzyme is quenched, e.g., by addition of nuclease inhibitors, in some embodiments, by addition of a metal ion chelator, such as EDTA etc., where the amount of inhibitor added to the mixture is sufficient to effectively quench/inhibit all of the enzyme activity in the mixture. In some embodiments, the activity of the enzyme is quenched by heating at 95-97° C. for 7-10 min. In some embodiments, the activity of the enzyme is not quenched. In this case, the reaction mixture is typically not kept more than two hours before signal detection.

Following the above cleavage step, the presence of cleaved oligonucleotide probes is then detected and related to the corresponding (i.e., the probe's complementary) nucleic acid sequence variant present in the sample. The manner in which the cleaved oligonucleotide probes are detected necessarily depends on the nature of the oligonucleotide probe label. For example, where the detectable label is an isotopic label positioned at one end of the probe, one can assay for detectably labeled fragments that are shorter than the full-length probe size and, in this manner, detect the presence of cleaved probes.

In certain embodiments, fluorescence labeled probes that provide for a distinct signal upon cleavage are employed, where examples of such probes include the FRET and fluorescence quencher probes described above. In these embodiments, the mixture is assayed for the presence of fluorescence signal that occurs only upon probe cleavage, and detection of this unique signal is employed to detect the presence of cleaved probes.

Since the above conditions result in cleavage of substantially only perfectly matched or complementary nucleic acid molecules, cleavage of preferably those probes for which a perfectly complementary nucleic acid sequence or sequence variant is present in the sample occurs. As such, the detection of probe cleavage products in the sample, as described above, provides for a highly accurate and specific determination of whether or not the corresponding nucleic acid sequence or sequence variant is present in the sample.

As mentioned above, the above general methods can be used to detect the presence of a single nucleic acid sequence variant of interest in a sample or a plurality of different nucleic acid sequences in a sample. When a plurality of different nucleic acid sequence variants are to be detected, the only limitation is that a labeling system, i.e., signal producing system of one or more entities, should be employed that provides for ready differentiation of different oligonucleotide probes to different target nucleic acid sequence variants. Alternatively, in the case of the array of the subject invention (described below), the oligonucleotides may contain a same label, because the signals for different sequence variants would be different by their positions.

The oligonucleotide probes that are employed may be in solution or immobilized on a solid support, e.g., presented as an array of oligonucleotide probes. The solid supports useful in the methods of the invention include, but are not limited to, agarose, acrylamide, and polystyrene beads; polystyrene microtiter plates (for use in, e.g., ELISA); and nylon and nitrocellulose membranes (for use in, e.g., dot or slot blot assays). Some methods of the invention employ solid supports containing arrays of oligonucleotide probes. In these cases, solid supports made of materials such as glass (e.g., glass plates), silicon or silicon-glass (e.g., microchips), or gold (e.g., gold plates) can be used. Methods for attaching nucleic acid probes to precise regions on such solid surfaces, e.g., photolithographic methods, are well known in the art, and can be used to make solid supports for use in the invention. (For example, see, Schena et al., Science 270:467-470, 1995; Kozal et al., Nature Medicine 2(7):753-759, 1996; Cheng et al., Nucleic Acids Research 24(2):380-385, 1996; Lipshutz et al., BioTechniques 19(3):442-447, 1995; Pease et al., Proc. Natl. Acad. Sci. USA 91:5022-5026, 1994; Fodor et al., Nature 364:555-556, 1993; Pirrung et al., U.S. Pat. No. 5,143,854; and Fodor et al., WO 92/10092.)

In embodiments where the oligonucleotide probe is immobilized on solid support, e.g., through covalent or non-covalent interactions, the presence of cleaved probe on the support is detected and related to the nucleic acid analyte to which that probe hybridizes, e.g., under-stringent hybridization conditions, such as the annealing conditions described above and in the experimental sections, below. For example, where the probe is labeled with a fluorescent label that provides for a unique signal when the probe is cleaved, the signal on the substrate is detected and related to the presence of the nucleic acid analyte in the sample.

The above methods can be employed to either qualitatively or quantitatively detect the presence of the nucleic acid sequence(s) in the sample. For example, the detection of cleaved oligonucleotide probes provides a qualitative determination of the nucleic acid sequences in the sample. To obtain a quantitative determination of the nucleic acid sequences in the sample, one can include a control in the assay, e.g., a known about of dsDNA labeled substrate, which provides a reference value to which the detected signal can be compared and thus extrapolated to provide a quantitative value.

The above methods find use in a number of different specific applications. Representative specific applications of interest include the detection of nucleic acid analytes (e.g. in diagnostics and biological applications where the presence of one or more nucleic acid analytes is indicative of the presence of a certain condition, organism, etc., in gene expression profiling where multiple nucleic acid analytes expressed in a cell are detected and compared to the same set of nucleic acids in a reference cell), detection of nucleic acid sequence variants (e.g. analysis of known point mutations, or single oligonucleotide polymorphisms in a DNA sample(s), allele discrimination, nucleic acid sequencing, etc.) and the like.

Examples of each of these specific applications are described in greater detail in the Experimental Section, infra.

Production of Normalized and Subtracted Libraries and Probes for Differential Screening The present invention provides several methods for obtaining subtractive and/or equalized DNA libraries and for preparation probes for differential screening. The methods are based on selectively cleavage of DNA in DNA containing nucleic acid duplexes to retain the single stranded DNA of interest. As such, the subject methods can be used for the elimination of the fractions of redundant and/or common molecules of DNA during normalization and\or subtractive hybridization.

In using the subject enzymes for normalization and\or subtractive hybridization, the sample from which equalized and\or subtracted libraries are to be produced is first obtained. The sample may be obtained from a variety of different sources, depending on the particular application being performed, where such sources as described in the previous section.

Depending on the particular interest, nucleic acids in the sample may be a RNA, double stranded DNA (for ex. genomic DNA or cDNA), or single stranded DNA.

If the tester nucleic acids (nucleic acids to be subtracted and/or normalized) is RNA, the prior step is first strand DNA preparation that is performed by any method known in the art. Depending on the particular interest and the amount of the starting material, the preparation of amplified DNA might is then performed. The DNA samples can also be exposed to mechanical shearing, restriction enzyme digest, etc. However, the methods are applicable for lengthy DNA, e.g. full-length cDNA. In some embodiments, the sample may be from a synthetic source.

While the DNA preparation can be performed by different standard methods, the resultant DNA molecules must comprise the terminal sequences of the known structure (adapters) that are used following PCR. Adapters are included in DNA molecules by the method known in the art, for example, during DNA preparation or are ligated to the prepared DNA.

Driver nucleic acids (nucleic acids that can hybridize with the fraction that must be eliminated from tester nucleic acids) may be a RNA, double stranded DNA (for ex. genomic DNA or cDNA), or single stranded DNA. If the driver nucleic acids are DNA, they must not contain the adapter sequences. In some embodiments these nucleic acids are DNA fragments or oligonucleotides that can hybridize with the fraction that must be eliminated from tester nucleic acids.

In certain embodiments nucleic acid samples are purified using appropriate protocols and methods known in the art (e.g. using QIAGEN Purification systems) and precipitated by ethanol with following resolution in the hybridization buffer. After the sample is obtained, the resultant DNA is denatured in the presence (subtractive hybridization or supernormalization)/or absence (normalization) of the driver nucleic acids obtained from the same (supernormalization) or other (driver for subtractive hybridization, probes for differential screening, etc.) sources. Denatured nucleic acids are allowed to anneal (hybridization step). Annealing (sometimes called hybridization) refers to the process by which complementary single-stranded nucleic acids form a double-stranded structure, or duplex, mediated by hydrogen-bonding between complementary bases in the two strands. Annealing conditions are those values of, for example, temperature, ionic strength, pH and solvent which will allow annealing to occur. Many different combinations of the above-mentioned variables will be conducive to annealing.

During annealing most of the abundant DNA molecules will form double-stranded (ds) molecules, and the single-stranded (ss) fraction will be equalized to a considerable extent [Galau G. A., Klein W. H., Britten R. J., Davidson E. H. II Arch. Biochem. Biophys. 1977. V. 179. P. 584-599]. In the presence of driver nucleic acids, annealing leads to duplex formation between the driver and tester nucleic acid strands if a particular sequence is common to both nucleic acid populations. Non-hybridized single-stranded DNA is enriched in sequences present in the experimental cell or tissue which is related to the particular change or event being studied.

After the hybridization step, the DNA containing duplex nucleic acids are digested by a suitable nuclease under DSN conditions (as described above) for a period of time sufficient for the DNA containing double-stranded substrates present in the sample to be cleaved by the enzyme. The amount of enzyme that is contacted with the reaction mixture is sufficient to provide for cleavage of DNA containing duplex nucleic acids present therein, where the amount typically ranges from about 5 min to about 48 h, usually from about 10 min to about 12 h and more usually from about 20 min to about 1 h. The temperature of the reaction mixture during this incubation period typically ranges from about 55 to about 72° C., usually from about 60 to about 65° C. At the end of the incubation period, the activity of the enzyme is quenched, e.g., by heating of the reaction mixture (for example at 97° C. for 7-10 min) or by addition of enzyme inhibitors (for example by addition of a metal ion chelator, such as EDTA etc.), where the amount of inhibitor added to the mixture is sufficient to effectively quench/inhibit all of the enzyme activity in the mixture.

ss-DNA fraction enriched in molecules of interest may be then amplified by PCR with adapter-specific primer.

Duplex Specific Nucleases

As summarized above, the subject invention also provides novel nucleases for use in practicing the above-described methods. The subject nucleases preferentially cleave deoxyribonucleic acids molecules in double-stranded form. The subject enzymes are endonucleases, such that they cut, i.e. cleave; break, etc., deoxyribonucleic acid molecules at a point other than the end of the molecule, if present, and do not require the molecule to have ends, e.g., the molecule may be a closed circular molecule. The subject enzymes cleave deoxyribonucleic acid substrate molecules in a manner that produces 5' phosphooligonulceotides, i.e., they cleave between the phosphate and the 3' hydroxyl to yield 5' phosphomonoester products.

A feature of the subject nucleases is that, under certain conditions (hereinafter referred to as "DSN conditions"), the subject enzymes preferentially cleave deoxyribonucleic acid molecules in double-stranded nucleic acids (duplex-specific nucleases, DSN). Furthermore, under DSN conditions, the subject enzymes cleave deoxyribonucleic acid molecules in perfectly matched short nucleic acid duplexes with substantially greater activity than non-perfectly matched nucleic acid duplexes of the same length.

As the subject enzymes preferentially cleave double-stranded nucleic acids under DSN conditions, they exhibit substantially no cleavage activity with respect to single-stranded nucleic acids. As such, the double-stranded nucleic acid cleavage activity of the subject enzymes far exceeds their single-stranded nucleic acid cleavage activity under DSN conditions, where the ds-nucleic acid cleavage activity exceeds ss-nucleic acid cleavage activity by at least about 5 fold, usually at least about 10 fold and more usually by at least about 50 fold, as measured using the cleavage activity described in above. The ds-nucleic acids that are cleaved by the subject enzymes are nucleic acids that contain at least one deoxyribonucleic acid (DNA) molecule. As such, the subject enzymes cleave DNA duplexes, as well as DNA in DNA/RNA hybrid duplexes. However, the subject enzymes exhibit substantially no cleavage activity with respect to RNA/RNA duplexes, such that the cleavage activity of DNA containing duplexes exceeds the cleavage activity of any other duplex nucleic acids by at least about 10 fold, usually at least about 50 fold and more usually by at least about 100 fold, as measured using the cleavage activity described above.

The subject enzymes preferentially cleave DNA in perfectly matched DNA containing short nucleic acid duplexes (DNA-DNA or DNA-RNA) with essentially greater activity than non-perfectly matched DNA containing nucleic acid duplexes of the same length. As such, under DSN conditions, the subject enzymes cleave completely matched DNA containing complexes at a rate that is at least about 5 fold, usually at least about 10 fold and more usually at least about 50 fold greater than the rate at which non-completely matched DNA containing complexes (that include as few as one bp mismatch) are cleaved, as measured using the cleavage activity described above.

The minimal duplex length of the nucleic acid substrates of the subject nucleases is, in many embodiments, at least 8 bp for DNA-DNA duplexes and 13 bp for DNA-RNA duplexes.

In certain embodiments, the subject nucleases are divalent cation dependent nucleases, such that in the absence of divalent cations, the subject enzymes are inactive, i.e., they do not cleave nucleic acids. In many embodiments, the subject nucleases are divalent metal cation dependent, such that in the absence of divalent metal cations, they do not cleave nucleic acids. As the subject enzymes are divalent cation dependent, their activity in the presence of divalent cations, specific divalent metal cations, can be inhibited or quenched by metal ion chelators, e.g., EDTA, etc. In addition, in some embodiments, the subject nucleases are thermostable. By thermostable is meant that the subject nucleases retain their activity over a wide range of elevated temperatures. As such, the subject nucleases are active at temperatures from about 15° C. to about 70° C., and show optimal activity at temperatures ranging from about 25° C. to about 65° C., usually from about 30° C. to about 65° C. and more usually from about 50° C. to about 60° C.

In some embodiments, the subject nucleases exhibit activity in conditions ranging in pH from about 6 to more than 10, where optimal activity is found at a pH ranging from about 6 to about 10.

In certain embodiments, the subject nucleases exhibit specific features under certain conditions (DSN conditions). In certain embodiments, "DSN conditions" are conditions in which $Mg^{2+}$ is present. In DSN conditions, the $Mg^{2+}$ concentration can range from about 2 to about 15, where the optimal $Mg^{2+}$ conditions range from about 3 to about 12, usually from about 4 to about 10 and more usually from about 6 to about 8 mM. Under DSN conditions, the pH typically ranges from about 6 to about 10, usually from about 7 to about 8.5.

In certain embodiments the subject nucleases are from, or have an amino acid sequence that is substantially the same as or identical to, a nuclease having the above properties and found in, a Metazoan animal, particularly an Arthropodoan animal, including the specific animals provided in the experimental section below. In certain embodiments, the nucleases are from, or have an amino acid sequence that is substantially the same as or identical to nuclease having the above properties and found in, a crustacean, and more specifically *Paralithodes camtschatica* (also known as Kamchatka crab; red king crab), or the other specific animals listed in the experimental section below.

In certain embodiments, the subject enzymes have an amino acid sequence that is substantially the same as or identical to Kamchatka crab nuclease having the following amino acid sequence:

(SEQ ID NO: 01)
MANMESKQGIMVLGFLIVLLFVSVNGQDCVWDKDTDFPEDPPLIFDSNLE

LIRPVLENGKRIVSVPSGSSLTLACSGSELINLGMEAVEAKCAGGVMLAI

EGTEWEIWSLGCSNHVKETIRRNLGTCGEADQGDRHSIGFEYYGGSIYYE

-continued

```
LISVCFGPVSETTLRTEHVLHGANIAAKDIETSRPSFKTSTGFFSVSMST

VYSQASQLQLMTDILGDSDLANNIIDPSQQLYFAKGHMSPDADFVTVAEQ

DATYYFINALPQWQAFNNGNWKYLEYATRDLAESHGSDLRVYSGGWSLLQ

LDDINGNPVDILLGLSEGKEVVPVPSLTWKVVYEESSSKAAAIVGINNPH

ITTAPSPLCSDLCSSLTWTDFNLDDLAHGYTYCCAVDDLRQAIPYIPDLG

NVGLLTN
```

In certain embodiments, the subject enzymes have an amino acid sequence that is substantially the same as or identical to the specific nucleases having the amino acid sequences provided in the experimental section below.

By "substantially the same as" is meant a protein having an amino acid sequence that has at least about 30%, sometimes at least about 40%, sometimes at least about 50%, sometimes at least about 60%, sometimes at least about 75%, and in certain embodiments at least about 80%, at least about 90% and in certain embodiments at least about 95%, 96%, 97%, 98% or 99% sequence identity with the sequence of SED ID NO:01, as measured by the BLAST compare two sequences program available on the NCBI website using default settings using the full length sequence.

In addition to the specific nuclease proteins described above, homologs or proteins (or fragments thereof) from other species, i.e., other animal species, are also provided, where such homologs or proteins may be from a variety of different types of species. By homolog is meant a protein having at least about 35%, usually at least about 40% and more usually at least about 60% amino acid sequence identity to the specific proteins provides above, where sequence identity is determined using the algorithm described supra.

The subject nucleases are present in a non-naturally occurring environment, e.g. are separated from their naturally occurring environment. In certain embodiments, the enzymes are present in a composition that is enriched for subject enzymes as compared to their naturally occurring environment. As such, purified nucleases are provided, where by purified is meant that nucleases are present in a composition that is substantially free of non-nuclease proteins, where by substantially free is meant that less than 90%, usually less than 60% and more usually less than 50% (by dry weight) of the composition is made up of non-nuclease proteins.

In certain embodiments of interest, the subject proteins are present in a composition that is substantially free of the constituents that are present in their naturally occurring environment. For example, a nuclease comprising composition according to the subject invention in this embodiment is substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the constituents or other components of the protein's naturally occurring source will still be present in the composition prepared from the naturally occurring source.

The subject proteins may also be present as isolates, by which is meant that the proteins are substantially free of both non-nuclease proteins and other naturally occurring biologic molecules, such as oligosaccharides, polynucleotides and fragments thereof, and the like, where substantially free in this instance means that less than 70%, usually less than 60% and more usually less than 50% (by dry weight) of the composition containing the isolated protein is a non-deoxyribose naturally occurring biological molecule. In certain embodiments, the subject proteins are present in substantially pure form, where by substantially pure form is meant at least 95%, usually at least 97% and more usually at least 99% pure.

In yet other embodiments, the subject nuclease may be present in a preparation that contains much less of the nuclease, e.g., less than about 50%, usually less than about 25% and often less than about 10 or even 5%, where in these embodiments, the preparation may have been treated, e.g., warmed.

In addition to the naturally occurring proteins described above, polypeptides that vary from the naturally occurring proteins are also provided. Such polypeptides are proteins having an amino acid sequence encoded by an open reading frame (ORF) of a protein according to the subject invention, described above, including the full length protein and fragments thereof, particularly biologically active fragments and/or fragments corresponding to functional domains, and including fusions of the subject polypeptides to other proteins or parts thereof. Fragments of interest will typically be at least about 10 aa in length, usually at least about 50 aa in length, and may be as long as 250 aa in length or longer, but will usually not exceed about the length of the full length protein.

Nucleic Acid Compositions

Also provided are nucleic acid compositions that encode the subject nucleases, fragments thereof, etc., as described above. Specifically, nucleic acid compositions encoding the above described enzymes/proteins, as well as fragments or homologs thereof, are provided. By "nucleic acid composition" is meant a composition comprising a sequence of nucleotide bases that encodes a nuclease polypeptide of the subject invention, as described above, i.e., a region of genomic DNA capable of being transcribed into mRNA that encodes a subject polypeptide, the mRNA that encodes and directs the synthesis of a subject polypeptide, etc. Also encompassed in this term are nucleic acids that are homologous, substantially similar or identical to the nucleic acids specifically disclosed herein. A specific coding sequences of interest is:

```
Kamchatka crab:
                                              (SEQ ID NO: 02)
AAGCAGTGGTATCAACGCAGAGTACGCGGGGGAGATAGGACTGAGTGAGT

GAGTGTGAGAGGGAAAGAAGGAATGGCCAACATGGAGTCCAAGCAAGGAA

TAATGGTTTTGGGATTCTTAATTGTCCTCCTCTTCGTGTCTGTCAATGGC

CAGGACTGTGTGTGGGACAAGGACACGGACTTTCCCGAGGACCCGCCACT

CATTTTCGATTCAAACTTGGAGCTCATCAGACCCGTCTTGGAAAATGGCA

AAAGGATCGTCACTGTCCCCAGTGGCAGCAGCTTAACCTTGGCCTGCTCT

GGGTCTGAACTGATCAACCTGGGCATGGAGGCGGTGGAAGCCAAGTGTGC

TGGGGGAGTCATGCTTGCCATAGAAGGAACGGAGTGGGAGATCTGGAGCC

TGGGGTGCAGCAACCACGTGAAGGAGACCATCCGCCGCAACCTTGGAACA

TGTGGGGAAGCGGACCAGGGGGATAGGCACAGTATTGGCTTCGAGTACTA

CGGTGGCTCCATCTATTATGAACTGATCAGCGTGTGTTTCGGGCCCGTGT

CCGAAACAACCTTGCGCACCGAGCATGTCCTCCACGGCGCCAACATTGCC

GCCAAGGACATCGAGACCTCCCGCCCCTCCTTCAAGACCTCCACCGGGTT

CTTCAGCGTCTCCATGTCCACCGTCTACAGCCAGGCGTCACAGCTGCAGT
```

-continued

```
TAATGACAGACATATTGGGAGATTCGGATCTAGCCAACAACATCATCGAC

CCCTCCCAACAGTTGTACTTCGCCAAAGGTCACATGTCTCCTGACGCAGA

CTTTGTGACGGTGGCAGAACAGGACGCCACCTACTACTTCATCAACGCCC

TACCGCAGTGGCAGGCCTTCAATAATGGCAACTGGAAGTACCTAGAATAC

GCGACCCGAGACCTGGCCGAATCCCACGGTAGCGACCTGCGAGTGTATAG

CGGAGGGTGGAGCCTGCTGCAGCTAGATGATATTAACGGCAACCCCGTGG

ACATCCTGCTGGGACTGTCTGAGGGCAAGGAGGTCGTGCCCGTTCCATCC

CTCACTTGGAAGGTGGTTTACGAAGAGAGCAGCAGCAAAGCGGCCGCGAT

CGTCGGTATCAACAACCCTCACATCACCACCGCCCCTCCCCCTTGTGTT

CCGACCTGTGCTCCTCCTTGACCTGGATAGACTTCAACCTGGACGACCTG

GCTCACGGGTACACCTACTGTTGTGCCGTAGATGACCTCCGGCAGGCCAT

ACCCTATATCCCGGACCTGGGCAATGTCGGACTCCTCACTAACTAATTCT

ATCTATCTATCATATATGCTCAGGCCCAATCCCCATTTTGGGGGTAGCCG

AACTCAAGAACAGAGCCAAGAAACAGGGAAAAAAAAAAAAAAAAAAAAAA

AAAAAAAAAAAAAAAAAA
```

Also provided are nucleic acids that are homologous to the provided nucleic acid of SEQ ID NO:02, at least with respect to the coding region thereof. The source of homologous nucleic acids to those specifically listed above may be any species. In certain embodiments, the homologs have sequence similarity, e.g., at least 30% sequence identity, usually at least 40%, more usually at least 50% sequence identity between nucleotide sequences. Sequence identity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). Unless indicated otherwise, the sequence similarity values reported herein are those determined using the above referenced BLAST program using default settings.

Of particular interest in certain embodiments are nucleic acids including a sequence substantially similar to the specific nucleic acids identified above, where by substantially similar is meant having sequence identity to this sequence of at least about 90%, usually at least about 95% and more usually at least about 99%.

Also provided are nucleic acids that hybridize to the above described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

The subject nucleic acids may be cDNAs or genomic DNAs, as well as fragments thereof. The nucleic acids may also be mRNAs, e.g., transcribed from genomic DNA, that encode (i.e. are translated into) the subject proteins and polypeptides. Genomic DNA typically includes the open reading frame encoding the subject proteins and polypeptides, and introns, as well as adjacent 5' and 3' non-coding nucleotide sequences involved, e.g., untranslated regions, promoter or other regulatory elements, etc., in the regulation of expression, up to about 20 kb beyond the coding region, but possibly further in either direction. The genomic DNA may be introduced into an appropriate vector for extrachromosomal maintenance or for integration into a host genome.

As such, a genomic sequence of interest comprises the nucleic acid present between the initiation codon and the stop codon, as defined in the listed sequences, including all of the introns that are normally present in a native chromosome. It may further include specific transcriptional and translational regulatory sequences, such as promoters, enhancers, etc., including about 1 kb, but possibly more, of flanking genomic DNA at either the 5' and 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The term "cDNA" as used herein is intended to include all nucleic acids that share the arrangement of sequence elements found in native mature mRNA species, where sequence elements at least include exons. Normally mRNA species have contiguous exons, with the intervening introns, when present, being removed by nuclear RNA splicing, to create a continuous open reading frame encoding the subject proteins.

The nucleic acid compositions of the subject invention may encode all or a part of the subject proteins and polypeptides, described in greater detail above. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The nucleic acids of the subject invention are isolated and obtained in substantial purity, generally as other than an intact chromosome. Usually, the DNA will be obtained substantially free of other nucleic acid sequences that do not include a coding sequence or fragment thereof for the subject proteins, generally being at least about 50%, usually at least about 90% pure and are typically "recombinant," i.e. flanked by one or more nucleotides with which it is not normally associated on a naturally occurring chromosome.

In addition to the plurality of uses described in greater detail in following sections, the subject nucleic acid compositions find use in the preparation of all or a portion of the subject proteins/polypeptides, as described below.

Also provided are nucleic acid probes, as well as constructs, e.g., vectors, expression systems, etc., as described more fully below, that include a nucleic acid sequence as described above. Probes of the subject invention are generally fragments of the provided nucleic acid. The probes may be large or small fragments, generally ranging in length from about 10 to 100 or more nt, usually from about 15 to 50 nt. In using the subject probes, nucleic acids having sequence similarity are detected by hybridization under low stringency conditions, for example, at 50° C. and 6×SSC (0.9 M sodium chloride/0.09 M sodium citrate)(or analogous conditions) and remain bound when subjected to washing at higher stringency conditions, e.g., 55° C. in 1×SSC (0.15 M sodium chloride/0.015 M sodium citrate) (or analogous conditions). Sequence identity may be determined by hybridization under stringent conditions, for example, at 50° C. or higher and 0.1×SSC (15 mM sodium chloride/01.5 mM sodium citrate) (or analogous conditions). Nucleic acids having a region of substantial identity to the provided nucleic acid sequences bind to the provided sequences under stringent hybridization conditions. By using probes, particularly labeled probes of DNA sequences, one can isolate homologous or related sequences.

The subject nucleic acids are isolated and obtained in substantial purity, generally as other than an intact chromosome. As such, they are present in other than their naturally occurring environment. Usually, the DNA will be obtained substantially free of other nucleic acid sequences that do not encode the above proteins/polypeptides, generally being at least about 50%, usually at least about 90% pure and are typically "recombinant", i.e. flanked by one or more nucleotides with which it is not normally associated on a naturally occurring chromosome.

The subject nucleic acids may be produced using any convenient protocol, including synthetic protocols, e.g., such as those where the nucleic acid is synthesized by a sequential monomeric approach (e.g., via phosphoramidite chemistry); where subparts of the nucleic acid are so synthesized and then assembled or concatamerized into the final nucleic acid, and the like. Where the nucleic acid of interest has a sequence that occurs in nature, the nucleic acid may be retrieved, isolated, amplified etc., from a natural source using conventional molecular biology protocols.

Also provided are constructs comprising the subject nucleic acid compositions inserted into a vector, where such constructs may be used for a number of different applications, including propagation, polypeptide/protein production, and the like, as described in greater detail below. Constructs made up of viral and non-viral vector sequences may be prepared and used, including plasmids, as desired. The choice of vector depends on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal or person. The choice of appropriate vector is well within the ability of those of ordinary skill in the art. Many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo. Typically, homologous recombination is accomplished by attaching regions of homology to the vector on the flanks of the desired nucleotide sequence. Regions of homology are added by ligation of oligonucleotides, or by polymerase chain reaction using primers that include both the region of homology and a portion of the desired nucleotide sequence, for example.

Also provided are expression cassettes that include coding sequence of the subject nuclease. By expression cassette is meant a nucleic acid that includes a sequence encoding a peptide or protein as described above operably linked to a promoter sequence, where by operably linked is meant that expression of the coding sequence is under the control of the promoter sequence.

Preparation of the Subject Proteins

The subject proteins may be obtained using any convenient protocol. As such, they may be obtained from naturally occurring sources or recombinantly produced. Naturally occurring sources of the subject proteins include tissues and portions/fractions thereof, including cells and fractions thereof, e.g., extracts, homogenates etc., that include cells in which the desired protein is expressed.

The subject proteins may also be obtained from synthetic protocols, e.g. by expressing a recombinant gene encoding the subject protein, such as the polynucleotide compositions described above, in a suitable host under conditions sufficient for post-translational modification to occur in a manner that provides the expressed protein. For expression, an expression cassette may be employed. The expression cassette or vector will provide a transcriptional and translational initiation region, which may be inducible or constitutive, where the coding region is operably linked under the transcriptional control of the transcriptional initiation region, and under the translational control of the translational initiation region, and a transcriptional and translational termination region. These control regions may be native to the protein, or may be derived from exogenous sources.

Expression cassettes may be prepared comprising a transcription initiation region, the nucleic acid coding sequence or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the coding sequence. After introduction of the DNA, the cells containing the construct may be selected by means of a selectable marker, the cells expanded and then used for expression.

The subject proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the coding sequence in eukaryotic cells, where the protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., Nature (1978) 275:615; Goeddel et al., Nature (1979) 281:544; Goeddel et al., Nucleic Acids Res. (1980) 8:4057; EP 0 036,776; U.S. Pat. No. 4,551,433; DeBoer et al., Proc. Natl. Acad. Sci. (USA) (1983) 80:21-25; and Siebenlist et al., Cell (1980) 20:269.

Yeast. Expression systems in yeast include those described in Hinnen et al., Proc. Natl. Acad. Sci. (USA) (1978) 75:1929; Ito et al., J. Bacteriol. (1983) 153:163; Kurtz et al., Mol. Cell. Biol. (1986) 6:142; Kunze et al., J. Basic Microbiol. (1985) 25:141; Gleeson et al., J. Gen. Microbiol. (1986) 132:3459;

Roggenkamp et al., Mol. Gen. Genet. (1986) 202:302; Das et al., J. Bacteriol. (1984) 158:1165; De Louvencourt et al., J. Bacteriol. (1983) 154:737; Van den Berg et al., Bio/Technology (1990) 8:135; Kunze et al., J. Basic Microbiol. (1985) 25:141; Cregg et al., Mol. Cell. Biol. (1985) 5:3376; U.S. Pat. Nos. 4,837,148 and 4,929,555; Beach and Nurse, Nature (1981) 300:706; Davidow et al., Curr. Genet. (1985) 10:380; Gaillardin et al., Curr. Genet. (1985) 10:49; Ballance et al., Biochem. Biophys. Res. Commun. (1983) 112:284-289; Tilburn et al., Gene (1983) 26:205-221; Yelton et al., Proc. Natl. Acad. Sci. (USA) (1984) 81:1470-1474; Kelly and Hynes, EMBO J. (1985) 4:475-479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: The Molecular *Biology* Of Baculoviruses (1986) (W. Doerfler, ed.); EP 0 127,839; EP 0 155,476; and Vlak et al., J. Gen. Virol. (1988) 69:765-776; Miller et al., Ann. Rev. Microbiol. (1988) 42:177; Carbonell et al., Gene (1988) 73:409; Maeda et al., Nature (1985) 315:592-594; Lebacq-Verheyden et al., Mol. Cell. Biol. (1988) 8:3129; Smith et al., Proc. Natl. Acad. Sci. (USA) (1985) 82:8844; Miyajima et al., Gene (1987) 58:273; and Martin et al., DNA (1988) 7:99. Numerous baculoviral strains and variants and corresponding permissive insect host cells from hosts are described in Luckow et al., Bio/Technology (1988) 6:47-55, Miller et al., Generic Engineering (1986) 8:277-279, and Maeda et al., Nature (1985) 315:592-594.

Mammalian Cells. Mammalian expression is accomplished as described in Dijkema et al., EMBO J. (1985) 4:761, Gorman et al., Proc. Natl. Acad. Sci. (USA) (1982) 79:6777, Boshart et al., Cell (1985) 41:521 and U.S. Pat. No. 4,399, 216. Other features of mammalian expression are facilitated as described in Ham and Wallace, Meth. Enz. (1979) 58:44, Barnes and Sato, Anal. Biochem. (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism.

Once the source of the protein is identified and/or prepared, e.g. a transfected host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the protein or the expression host expressing the protein, and purified using HPLC, exclusion chromatography, gel electrophoresis, affinity chromatography, and the like.

Also of interest is the use of modified versions of the wild type sequences which are modified to provide for optimized expression in a particularly type of expression host. For example, humanized versions of the subject nucleic acids can be used for expression in human cell lines, where changes are made to the wild type nucleic acid sequence to optimize the codons for expression of the protein in human cells (Yang et al., *Nucleic Acids Research* 24 (1996), 4592-4593). See also U.S. Pat. No. 5,795,737 which describes humanization of proteins, the disclosure of which is herein incorporated by reference.

In certain embodiments, the subject proteins are produced as fusion proteins. In these embodiments, nucleic acids that encode fusion proteins of the subject proteins, or fragments thereof, which are fused to a second protein, a tagging sequence, etc. Fusion proteins may comprise a subject polypeptide, or fragment thereof, and a DNase polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject nuclease portion of the fusion protein, and is typically not an nuclease protein or derivative/fragment thereof. Of particular interest in many protein production application is the use of fusion partners encoding metal ion peptide affinity tags, e.g., the 6×His tag and other metal ion affinity tags, where the tags provide for ready purification on appropriate metal ion affinity resins. Metal ion affinity tagged peptide technology is well known to those of skill in the art, and is described in U.S. Pat. Nos. 5,284,933; 5,310,663; 4,569,794; 5,594,115 and 6,242,581; the disclosures of which are herein incorporated in their entirety.

The subject polypeptides, peptides, variants and or fragments thereof may also be prepared through chemical synthesis. The polypeptides may be monomers or multimers; glycosylated or non-glycosylated; pegylated or non-pegylated; amidated or non-amidated; sulfated or non-sulfated; and may or may not include an initial methionine amino acid residue. For example, the polypeptides can also be synthesized by exclusive solid phase synthesis, partial solid phase methods, fragment condensation or classical solution synthesis. The polypeptides are in many embodiments prepared by solid phase peptide synthesis, for example as described by Merrifield, J. Am. Chem. Soc. 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: A Practical Approach, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300-320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluoro-phosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al., Anal. Biochem. 34:595, 1970. After the entire assembly of the desired peptide, the peptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1-2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III)trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

Antibodies

Also provided are antibodies that bind to the subject proteins and/or homologs thereof. Suitable antibodies are obtained by immunizing a host animal with peptides comprising all or a portion of the subject protein. Suitable host animals include rat, sheep, goat, hamster, rabbit, etc. The host animal will generally be a different species than the immunogen, e.g. human used to immunize rabbit, etc.

The immunogen may comprise the complete protein, or fragments and derivatives thereof. Preferred immunogens comprise all or a part of the subject protein, where these residues contain the post-translation modifications, such as glycosylation, found on the native target protein (immunogens may also comprise all or a part of the subject protein, where these residues does not contain the post-translation modifications).

Immunogens comprising the extracellular domain are produced in a variety of ways known in the art, e.g. expression of cloned genes using conventional recombinant methods, isolation from naturally occurring sources, etc.

For preparation of polyclonal antibodies, the first step is immunization of the host animal with the target protein, where the target protein will preferably be in substantially pure form, comprising less than about 1% contaminant. The immunogen may include the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies of the subject invention may be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using MPTS bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

The antibodies or fragments thereof may also be produced using phage display technology. Phage display technology is well known to those of skill in the art, where representative patents describing various representative embodiments of this technology include U.S. Pat. Nos. 5,427,908; 5,580,717; 5,658,727; 5,723,287; 5,750,373; 5,780,279; 5,821,047; 5,846,765; 5,885,793; 5,955,341; 6,040,136; 6,057,098; and 6,172,197; the disclosures of which are herein incorporated by reference.

Kits

Also provided are kits for use in practicing the subject methods. The methods of the invention can be facilitated by the use of kits that contain the reagents required for carrying out the assays. The kits can contain reagents for carrying out the analysis of a one single nucleotide polymorphism (SNP) site (for use in, e.g., diagnostic methods) or multiple SNP sites (for use in, e.g., genomic mapping). When multiple samples are analyzed, multiple sets of the appropriate primers and oligonucleotides are provided in the kit. In addition to the primers and oligonucleotides required for carrying out the various methods, the kits contain the nuclease enzyme, such as the novel nucleases described above, and DSN buffer (e.g., buffer where these nucleases work correctly). Also the kits may contain the reagents for detecting the labels and for nucleic acids amplification. The kits can also contain solid substrates for use in carrying out the method of the invention. For example, the kits can contain solid substrates, such as glass plates or silicon or glass microchips, containing arrays of nucleic acid probes.

In addition to the above components, the subject kits will further include instructions for practicing the subject methods. These instructions may be present in the subject kits in a variety of forms, one or more: of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Isolation and Characterization of Kamchatka Crab Nuclease

A. Purification of Crab Nuclease Protein

A specific nuclease activity was found in crab hepatopancreas. The activity was purified by standard methods of protein chemistry. Because the specific activity of this enzyme is thermostable, both purified and partially purified samples (after warming) of crab nuclease display the specific activity.

The purification scheme may be different and may include different stages. A representative scheme is provided below:

Crab DSN nuclease was purified at 4° C. Fractions were subjected to testing for DNase activity and Western blotting (Harlow and Lane, 1988) with rabbit polyclonal antibodies against recombinant protein.

Fresh crab hepatopancreas was homogenized in two volumes of 100 mM Tris-HCl (pH 8.0) with 100 mM EDTA and centrifuged at 10 000 g for 30 min. The supernatant was diluted with 1.5 volumes of acetone, incubated for 12 h and centrifuged at 10 000 g for 1 h. The sediment was dried and 5 g of the resultant acetone powder was diluted in 250 ml buffer A (0.05 M Tris-HCl, pH 7.1) and mixed for 2 h. The insoluble fraction was separated out by centrifugation at 10 000×g for 30 min, and the supernatant was applied to a DEAE-Macro-Prep column (Bio-Rad) equilibrated with buffer A. After loading, the column was washed with the same buffer. Protein was eluted with a 0-0.5 M NaCl gradient in buffer A. After adding NaCl to a final concentration of 5 M, DSN-containing fractions were loaded onto a Phenyl-Agarose column (Amersham-Pharmacia-Biotech) equilibrated with buffer A containing 5 M NaCl. After washing the column with the same high-salt buffer, DSN was eluted with a 5-3 M NaCl gradient in buffer A. DSN-containing fractions were pooled, diluted two-fold with 0.035 M Tris-HCl (pH 8.1) and applied to a Hydroxyapatite column (Bio-Rad) equilibrated with 0.045 M Tris-HCl (pH 7.5). The fractions were directly eluted with 0.025 M sodium phosphate buffer, pH 7.5, combined and dialyzed overnight against 0.01 M Tris-HCl (pH 7.1) containing 0.001 M $MgCl_2$. Dialyzed fractions were loaded onto a Heparin-Sepharose column (Amersham-Pharmacia-Biotech), equilibrated with the 0.01 M Tris-HCl (pH 7.1) buffer containing 0.001 M $MgCl_2$, and eluted with a 0-0.3 M NaCl gradient after washing. DSN-containing fractions were concentrated to 1 ml on a Biomax-5K membrane (Millipore), transferred to buffer A and subjected to gel filtration on a Sephadex G-75 (Sigma) column. Purified DSN was concentrated on Biomax-5K membrane, diluted with one volume of glycerol, heated at 70° C. for 10 min under mineral oil and incubated at +4° C. overnight. About 0.15 mg DSN protein (2700 Kunitz units) was purified from 5 g acetone powder. DSN was stored at −20° C. for long-term use.

B. Isolation of the Crab Nuclease Coding Sequence.

To isolate coding sequence of crab nuclease and its homologues from other species, a set of oligonucleotide primers were designed to the conserved amino acids of the various nucleases: *Serratia marcescens* nuclease (1583130), *Glossina morsitans* nuclease (AAF82097), *Homo sapiens* nuclease (XP_002889), *Syncephalastrum racemosum* nuclease (P81204), *Cunninghamella echinulata* nuclease (P81203), *Drosophila melanogaster* nuclease (AAF49206) and *Penaeus japonicus* nuclease (CAB55635).

| NN | Primer name | Primer Sequence |
|---|---|---|
| 1. | PQW1 | 5'-TAC ATT AAT GCC GTC CCT CAG TGG-3' (SEQ ID NO: 03) |
| 2. | GNW1 | 5'-CAG GCC TTT AAT AAT GGT AAT TGG-3' (SEQ ID NO: 04) |
| 3. | GNW2 | 5'-AG GCC TTT AAT AA(T/C) GGT AAC TGG-3' (SEQ ID NO: 05) |
| 4. | AFN1 | 5'-CCT CAG TGG CA(G/A) GCT TT(C/T) AAT-3' (SEQ ID NO: 06) |
| 5. | AFN2 | 5'-CCT CAG TGG CA(G/A) GCT TT(C/T) AAC-3' (SEQ ID NO: 07) |

All primers were purified through polyacrylamide gel before use.

For crab nuclease cDNA isolation, the modified method for amplifying cDNA ends based on SMART-RACE technology (Clontech Laboratories Inc., Palo Alto, Calif.) was used. SMART-RACE technology also noted as step-out RACE has been described in (Matz, M., Shagin, D., Bogdanova, E., Britanova, O., Lukyanov, S., Diatchenko, L., Chenchik, A. (1999) *Nucleic Acids Res.* 27, 1558-1560). Total RNA from King crab hepatopancreas was isolated as described in (Chomczynski, P., Sacchi, N. (1987) *Anal. Biochem.* 162, 156-159). The cDNA was amplified by a SMART PCR cDNA Synthesis Kit (CLONTECH) using the provided protocol and then used for 3'-step-out RACE (Matz et al., 1999). PCR reaction was performed in a 25 mkl reaction mixture containing 1 mkl of 20-fold amplified cDNA, 1× Advantage 2 Polymerize mix (CLONTECH), the manufacturer's 1× reaction buffer, 200 mkM dNTPs, 0.3 mkM of AFN1 degenerative primer, and step-out primer system (0.02 mkM of "heel-carrier" oligo and 0.15 mkM of "heel-specific" oligo). 30 PCR cycles were performed in PTC-200 MJ Recearch Termal Cycler in calculated control mode (each cycle included 95° C.—10 s; 60° C.—10 s; 72° C.—2 min). 1/1000 of resulted amplified cDNA was used for nested PCR with GNW1 primer. PCR reaction was performed in a 25 mkl reaction mixture containing 1× Advantage 2 Polymerize mix (CLONTECH), the manufacturer's 1× reaction buffer, 200 mkM dNTPs, 0.3 mkM of GNW1 primer, and step-out primer system (0.02 mkM of "heel-carrier" oligo and 0.15 mkM of "heel-specific" oligo). 21 PCR cycles were performed in PTC-200 MJ Recearch Termal Cycler in calculated control mode (each cycle included 95° C.—10 s; 64° C.—10 s; 72° C.—2 min).

PCR products were cloned in pTAdv-cloning vector (CLONTECH) and sequenced using M13 direct and reverse universal primer by using a Beckman SEQ-2000 automated sequencer and the FS dye terminator chemistry.

cDNA containing the full coding sequence of crab DSN was then isolated using SMART-RACE technology (Clontech Laboratories Inc., Palo Alto, Calif.). For additional RACE procedures the crab nuclease specific primers were used as following: 5'-GGC CAG GTC TCG GGT CGC-3'; 5'-GGG TCG CGT ATT CTA GGT A-3' (SEQ ID NO:08); 5'-CC ATT ATT GAA GGC CTG CCA-3' (SEQ ID NO:09).

The nt sequence of the isolated cDNA is provided in SEQ ID NO:01 and the amino acid sequence of the protein encoded thereby is provided in SEQ ID NO:02, which sequences are provided above.

C. Generation of Antibodies

Polyclonal antibodies were prepared to His-tagged mature DSN protein produced in *Escherchia coli*. Recombinant products were purified by immobilized metal affinity chromatography using Talon Resin (Clontech Laboratories, Inc.) under denaturing conditions. Rabbits were immunized and boosted four times at monthly intervals with recombinant DSN polypeptide emulsified in complete Freund's adjuvant. Ten or 11 days after each boost the animals were bled. Polyclonal antiserum was tested on recombinant protein by ELISA and by Western immunoblotting. Polyclonal antiserum was then used for Western immunoblotting with total protein extract from crab hepatopancreas and partially purified DSN samples. The samples enriched in specific activity had greater staining than unpurified samples.

D. Testing of DSN Activity.

The above cloned crab Double stranded nuclease (DSN) is a $Mg^{2+}$-dependent nuclease with following properties:

DNAse activity of the subject nuclease is at least 18 000 Kunitz-units per 1 mg of the protein as determined by modified DNase activity assay (Kunitz M, 1950, *J. Gen. Physiol.* 33, pages 349-362; Liao, T.-H. 1974 *J. Biol. Chem.* 249: pages 2354-2356). Activity was determined in reaction mixture containing 5 mM Tris-HCl, pH 7.5, 10 mM $MgCl_2$, 10 mM $CaCl_2$, 400 mkg calf thymus DNA and crab nuclease in different concentration. Nuclease concentration was determined using Bradford method (Bradford M., Anal. Biochem., 1976, v. 72, p. 248-254).

In the absence of $Mg^{2+}$ ions crab DSN is inactive.

In the presence of $Mg^{2+}$-ions and in the absence of $Ca^{2+}$-ions, only of about 50% of nuclease activity keeps as was measured by modified Kunitz assay.

crab DSN exhibited strong cleavage preference for ds DNA substrates (DNA-DNA and DNA in DNA-RNA hybrids) and little activity against ss DNA. No significant cleavage activity on RNA substrates was observed (RNase activity was measured essentially as described by Ho H C., Shiau P. F., Liu F. C., Chung J. G., Chen L. Y. Eur J. Biochem. 1998, 256: 112-118).

Figure 2:
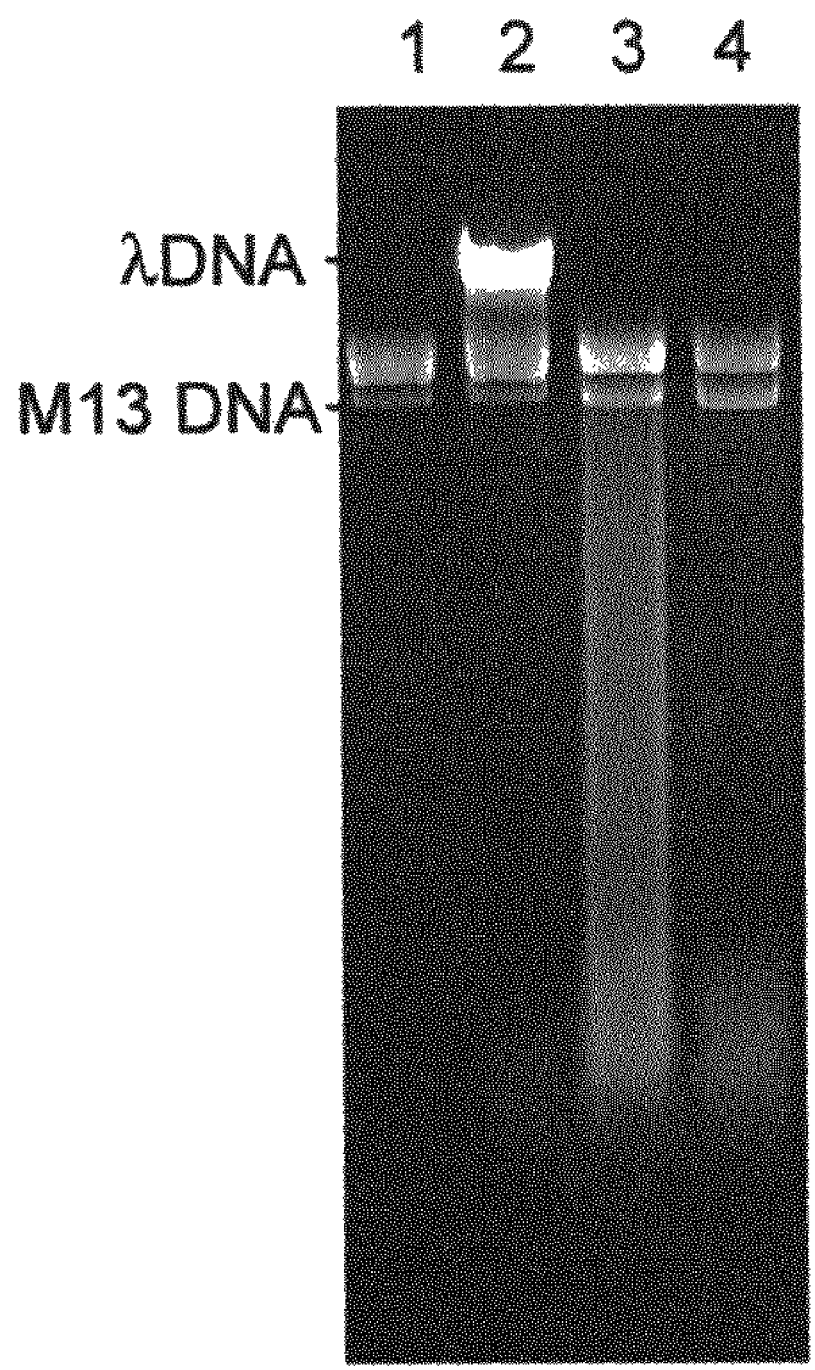
FIG. 2 provides the results of crab DSN action on ss phage M13 DNA and ds λ DNA. Lanes 1, 2—negative controls, incubation without nuclease. 1—phage M13 DNA alone, 2—mixture containing phage M13 DNA and λ DNA. Lanes 3, 4—digestion of phage M13 and λ DNA mixture by crab nuclease at 70° C. for 1.5 min (lane 3) and 5 min (lane 4).

Following examples demonstrate structure-specificity of crab DSN described above:

1. DSN activity on λ ds DNA and phage M13 ss-DNA was compared by agarose gel electrophoresis. The reaction was performed in a total volume of 10 µl comprising 1×DSN buffer (7 mM $MgCl_2$, 50 mM Tris-HCl, pH 8.0), 0.06 Kunitz/units DSN, 150 ng λ DNA and 50 ng M13 DNA. To prevent ds structure formation in phage M13 DNA, the reaction mixture was incubated at 70° C. for 1, 5 or 5 min. The digestion products were visualized on a 0.9% agarose gel, following ethidium bromide staining (FIG. 2)

2. For analysis of crab DSN activity on synthetic oligonucleotide substrates, oligonucleotides labeled with a fluorescent donor at the 5' end and a fluorescent quencher at the 3' end were used as ss DNA. To generate ds substrates, labeled oligonucleotides were mixed with equimolar amounts of complementary non-labeled oligonucleotides.

Figure 3:
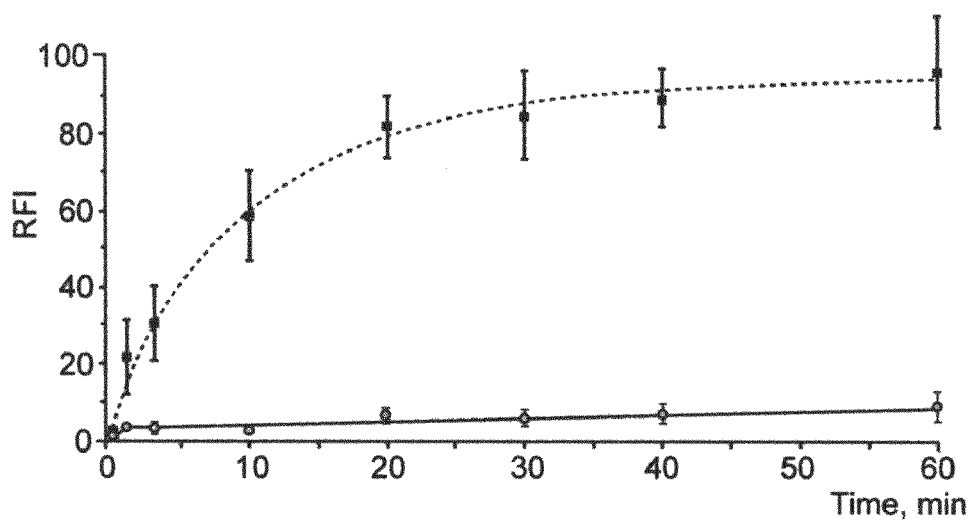
FIG. 3 provides the results of a crab DSN DNAse activity assay performed on ds- and ss-DNA 20-mer DNA substrates labeled by TAMRA at 5'-end and DABCYL at 3'-end. Fluorescence intensity was measured at 570 nm (with excitation at 550 nm). The relative fluorescence increase in the oligonucleotide substrate, RFI, was defined as RFI=(Fi−Fo/Fmax−Fo)× 100%, where Fi is the fluorescence intensity of a substrate after incubation with nuclease, Fo is the substrate fluorescence in the absence of enzyme, and Fmax represents the fluorescence of 100% cleaved substrate. For kinetic graph construction, three identical experiments were performed and the average values and standard deviations were plotted (first and second sequences shown: SEQ ID NO 55; third sequence shown: SEQ ID NO 56).

2.1. Action of crab nuclease on synthetic ss and ds 20-mer DNA substrates was performed in a total volume of 20 µl comprising 1×DSN buffer 50 mM Tris-HCl, pH 8.0 and 7 mM $MgCl_2$), 0.6 Kunitz units DSN, and 0.3 µM oligonucleotide substrate. Incubation was carried out at 35° C. for different periods. DNase activity was evaluated by estimating the change in fluorescence intensity of the reaction mixture during incubation with DSN. Fluorescence intensity was measured on a spectrofluorimeter Cary Eclypse (Varian) in 2 ml dishes (FIG. 3).

2.2. Action of crab nuclease on synthetic ds DNA substrates of different length was performed in a total volume of 20 µl comprising 1×DSN buffer, 1.5 Kunitz units DSN, and 0.3 µM oligonucleotide substrate. Incubation was carried out at 35° C. for different periods. DNase activity was evaluated by estimating the change in fluorescence intensity of the reaction mixture during incubation with DSN. Fluorescence intensity was measured on a spectrofluorimeter Cary Eclypse (Varian) in 2 ml dishes (FIG. 4). Cleavage curves were plotted to obtain half-time for substrate cleavage (T1/2).

Figure 5:
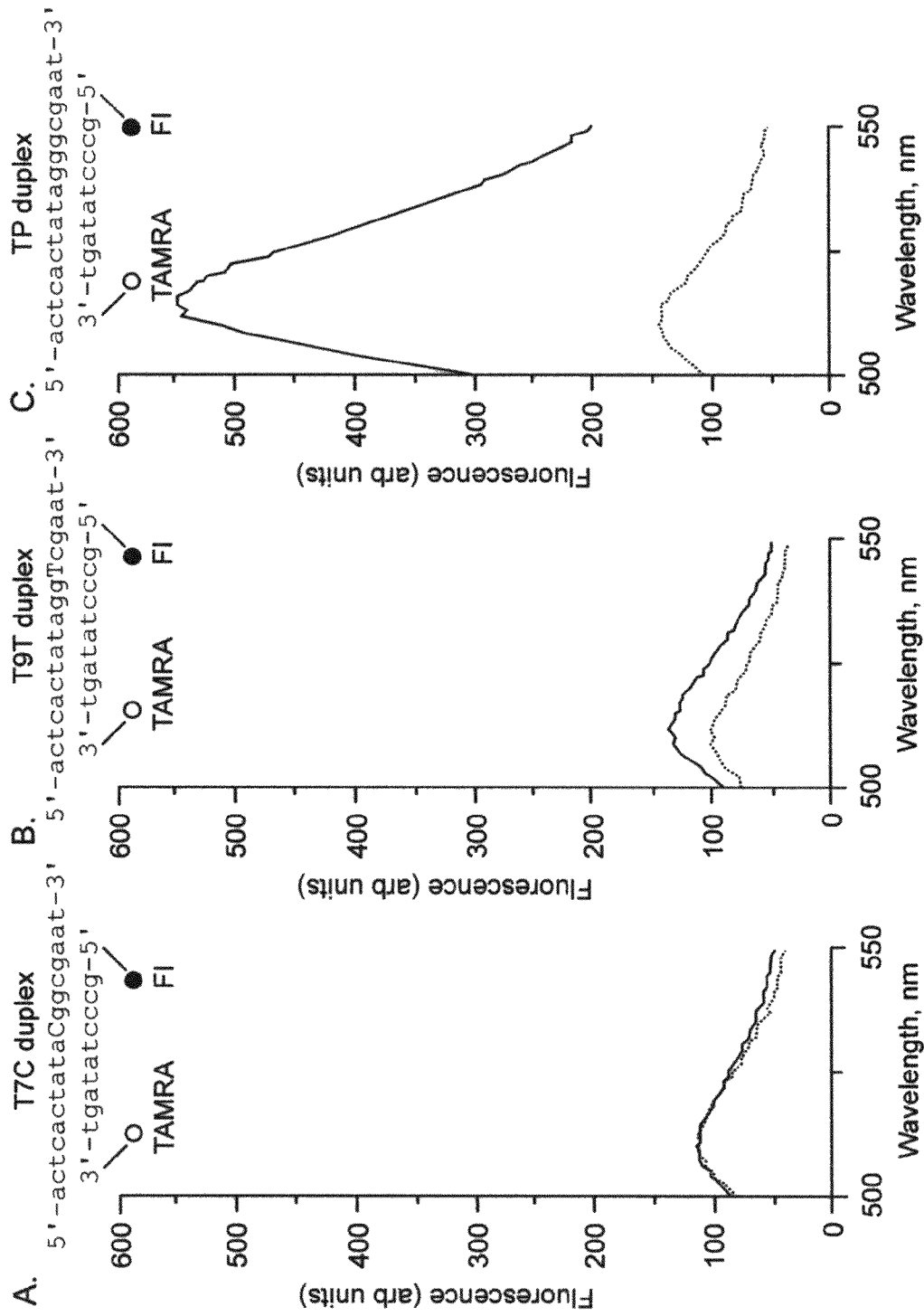
FIGS. 5 A to C provide results of crab DSN action on one mismatch-containing (A, B) and perfectly matched (C) DNA duplexes formed by 5-carboxyfluorescein (Fl)-5'-gccctatagt-3'-TAMRA probe oligonucleotide and complementary strand. Dotted line—substrate fluorescence in the absence of enzyme; firm line—substrate fluorescence after incubation with DSN (labeled probe oligonucleotide in A, B and C, bottom: SEQ ID NO 64; target sequence in A: SEQ ID NO 63; target sequence in B: SEQ ID NO 65; target sequence in C: SEQ ID NO 66).

DSN is significantly more effective in cutting perfect DNA-DNA and DNA-RNA duplexes than it is in cutting non-perfect duplexes of the same length. The following example demonstrates the structure-specificity of crab DSN described above: To determine the generality of mismatch discrimination, we constructed a set of closely related 18 nt synthetic targets with single nucleotide variations along the 10 nt sequence and FRET-labeled 10 nt probe oligonucleotide capable of hybridizing with these targets to form perfect and one mismatch-containing duplexes. Two types of signal probes were used, specifically, probes labeled with 5-carboxyfluorescein (Fl) (at the 5' end) and TAMRA (at the 3' end) and those labeled with Fl and DABCYL. Duplexes formed by probe oligonucleotides and complementary targets were incubated with DSN at 35° C. for 15 min. Reactions were performed in a total volume of 20 µl comprising 1×DSN buffer, 0.6 Kunitz units DSN, and 0.3 µM oligonucleotide substrate. Emission spectra were obtained on the spectrofluorimeter, with excitation at 480 nm (see FIG. 5 for example). All possible combinations between targets and probe oligonucleotides were examined for cleavage by DSN. The observed fluorescence change for all mismatched duplexes was at least 10 times lower than that for perfectly matched duplexes in the experiments with Fl-TAMRA-labeled probe. No preference of DSN for specific mismatch positions was noted. In the case of the Fl-DABCYL labeled probe, clear discrimination between perfect and non-perfect duplexes was observed if the variable nucleotide position was either at the 5' end or the center of a signal probe. Duplexes comprising mismatches near the 3' end of the signal probe (T1-4) were cleaved by DSN with only 1.5-5 times less efficiency than perfect duplexes.

Examples that demonstrate the specific activity of crab DSN on perfectly and non-perfectly matched DNA containing duplexes are also shown in "Examples of DSNP ASSAY Methods" section (below).

Figure 6:
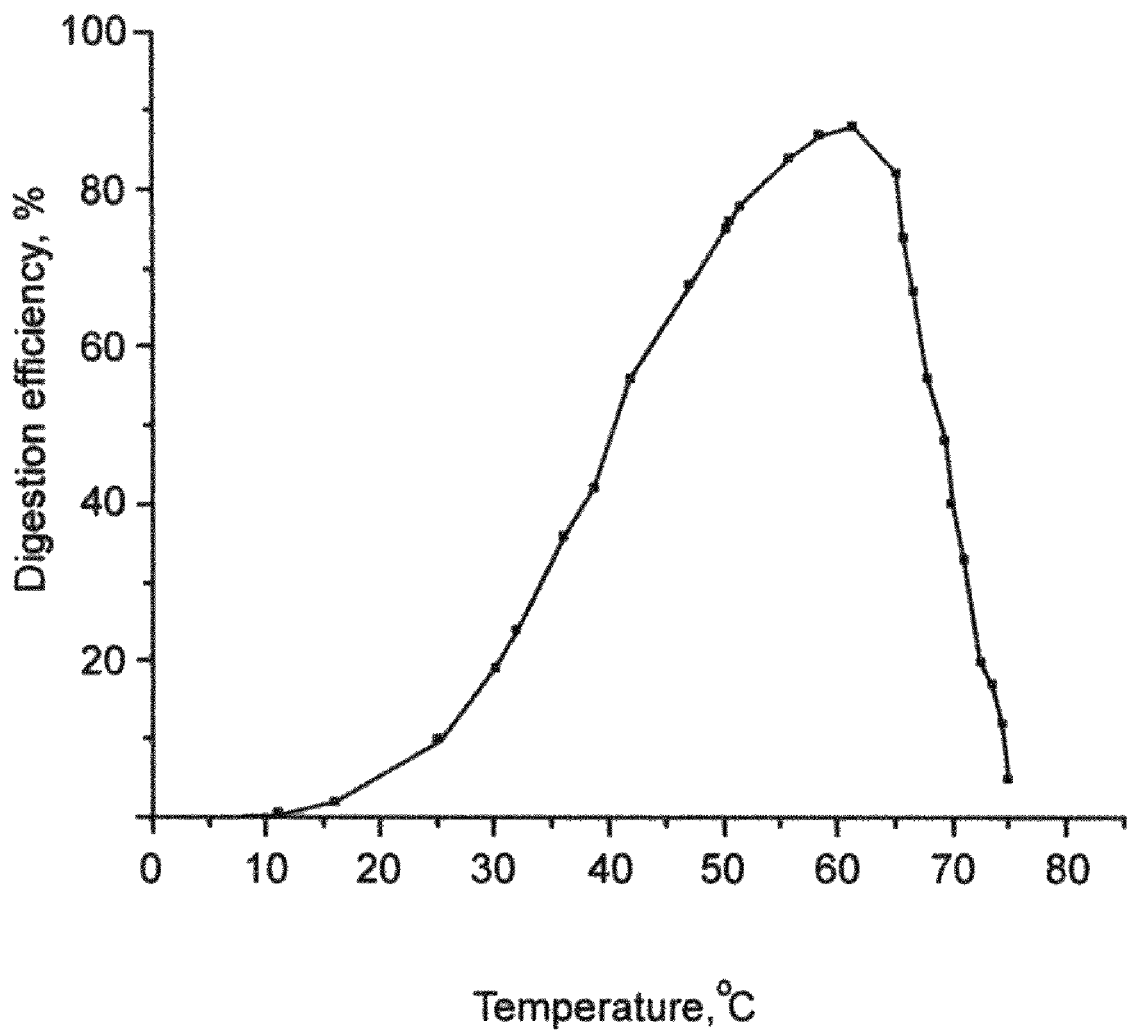
FIG. 6 provides a graphic chart of the crab DSN activity from temperature. Activity of DNAse was measured using Kunitz assay.
Figure 7:
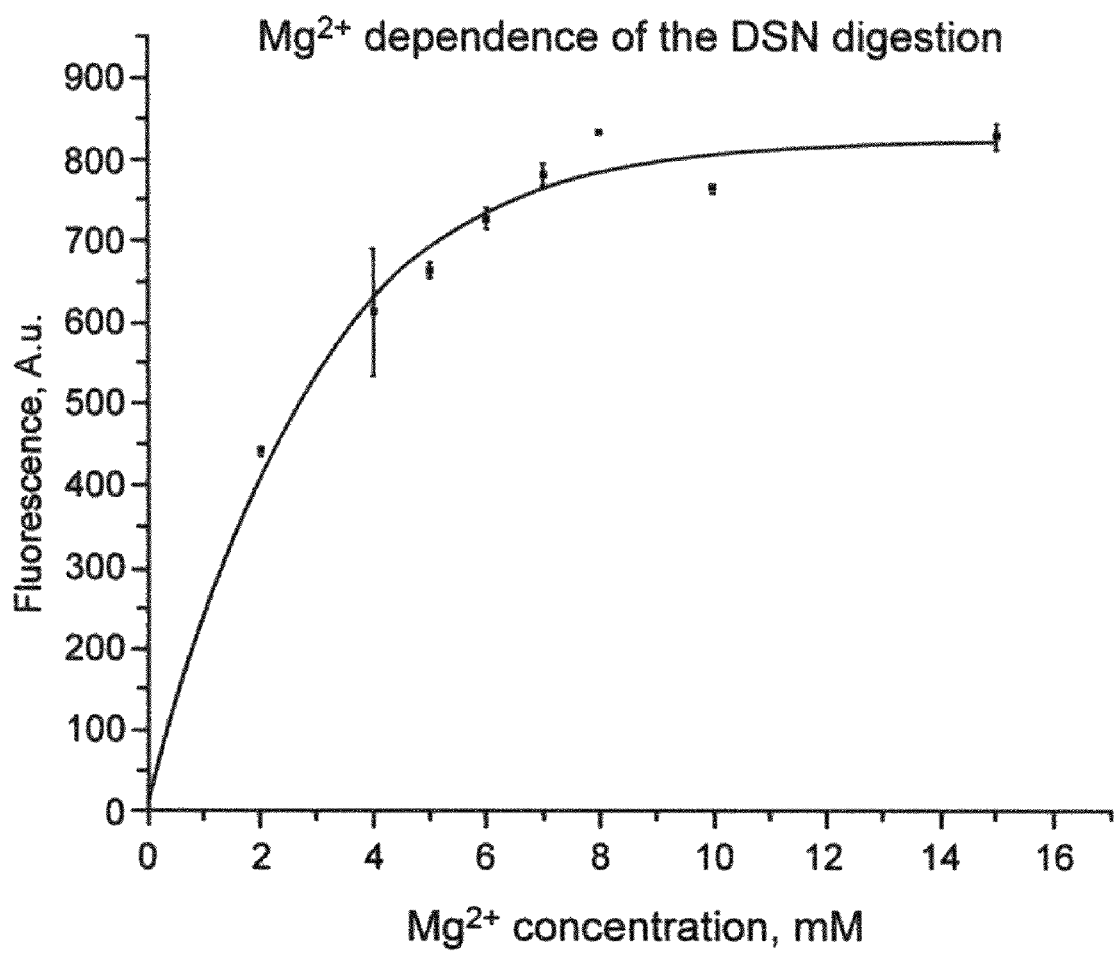
FIG. 7 provides graphic chart of the crab DSN activity from $Mg^{2+}$ concentration. To analyze the $Mg^{2+}$-ion dependence of crab DSN, 10 nt long oligonucleotide labeled with a fluorescent donor (5-carboxyfluorescein) at the 5' end and a quencher (DABCYL) at the 3' end, was mixed with non-labeled 18 nt long oligonucleotide that contains a region perfectly complemented to 10 nt oligonucleotide to form ds-DNA substrate. Probes were prepared on ice. The DNA endonuclease activity was assayed in 20 µl reactions containing 50 mM Tris-HCl, pH8.0; 0.5 mkM of substrate oligonucleotides, 1-Kunitz-units crab DSN and different concentrations of $MgCl_2$. The reactions were carried out 10 min at 35° C. and then stopped by the addition of EDTA solution. Fluorescence was measured on spectrofluorimeter Cary Eclypse (Varian, Australia) in 2 ml dishes.

The pH and temperature optima for crab DSN activity are 7-8 and 55-65° C., respectively. The nuclease is stable at a pH of greater than 6, and temperatures below 75° C. The dependence of DSN activity on pH was analyzed using the Kunitz assay with 50 mM sodium formiate (pH 3.0-3.5), 50 mM sodium acetate (pH 3:5-6.0), 50 mM Mes-NaOH (pH 6.0-7.0), 50 mM Tris-HCl (pH 7.0-9.5) and 50 mM glycine-NaOH (pH 9.0-10.0) in the presence of 7 mM $MgCl_2$. The dependence of DSN activity on temperature was analyzed at different reaction temperatures, ranging between 20 and 90° C. The activity of crab DSN in different temperatures is demonstrated graphically in FIG. 6. The activity of crab DSN in different $Mg^{2+}$ concentration is demonstrated graphically in FIG. 7.

Crab DSN is inactive in the absence of divalent cations. EDTA inhibits the Crab DSN. Crab DSN is also fully inactivated by heating at temperature 97° C. (or higher) for 7-10 min.

E. Cloning of Putative Nucleases of DSN Family from Other *Arthropoda* Species

Using a modified method for amplifying cDNA ends based on SMART-RACE technology and primers described above, several cDNAs that encode proteins homologues to crab DSN have been cloned. Amplification reactions contained 1× Advantage 2 Polymerize mix (CLONTECH), the manufacturer's 1× reaction buffer, 200 mkM dNTPs, 0.3 mkM of primer, and step-out primer system (0.02 mkM of "heel-carrier" oligo and 0.15 mkM of "heel-specific" oligo) in a volume of 25 µl. PCR was carried out in 200 MJ Recearch Termal Cycler in calculated control mode.

For isolation of the *gammarus* (*Gammarus* sp.) putative nuclease 34 cycles PCR were performed with AFN2 primer by the following program: 95° C.—10 s; 62° C.—10 s; 72° C.—2 min.

For isolation of the glass shrimp (*Palaemonidae* sp) and Mangrove Fiddler Crab (*Uca crassipes*) putative nucleases two consistent PCRs were carried out. The AFN2 primer was used for the first PCR that included 32 cycles by the following program: 95° C.—10 s; 60° C.—10 s; 72° C.—2 min and the GNW1 primer was used for the second (nested) PCR that included 25 cycles (each cycle included 95° C.—10 s; 64° C.—10 s; 72° C.—2 min).

cDNAs containing the full coding sequences of these nucleases were then isolated using SMART-RACE technology (Clontech Laboratories Inc., Palo Alto, Calif.) with following gene-specific primers:

Fiddler Crab nuclease-specific primers: 5'-GG ATT GCC ATT AAT GTC GTC-3' (SEQ ID NO:10); 5'-CC ACT GTA CAC CCG AAG GTC-3' (SEQ ID NO:11); 5'-AAC CAA GGC TCG CCA AGT CC-3' (SEQ ID NO:12); *gammarus* nuclease-specific primers: 5'-C AAT GGT CCG AAT TCT GTT CTC-3' (SEQ ID NO:13); 5'-GTG ACT ACG CGC AGA GTG GC-3' (SEQ ID NO:14); and glass shrimp nuclease-specific primers: 5'-CCA GCA CTC CCC AAC CTC C-3' (SEQ ID NO:15); 5'-GTC AGG TCA GTG CCG TGG GC-3' (SEQ ID NO:16).

The nt sequences of the isolated cDNA are provided in SEQ ID NO:17; SEQ ID NO:19; and SEQ ID NO:21 and the amino acid sequences of the protein encoded thereby are provided in SEQ ID NO:18; SEQ ID NO:20; and SEQ ID NO:22, which sequences are provided below:

*Gammarus* Putative Nuclease:

Source: *Eukaryota; Metazoa; Arthropoda; Crustacea; Malacostraca; Eumalacostraca; Peracarida; Amphipoda; Gammaridea; Gammaroidea; Gammaridae; Gammarus; Gammarus* sp.

```
Nucleic acid composition
                                       (SEQ ID NO: 17)
TGTAGCGTGAAGACGACAGAAGTAATACGACTCACTATAGGGCAAGCAGT
GGTACCAACGCAGAGTACTCGTCTTCCTTTTTTTTTTGGTGTTGCTGCC
CCACTGTGCAAACTTGAGGCGCTGCTCTTGGCAACTGAGAAATTCTACGA
ATCAGACGATACACGCTTCATAGTTCAGACCACTTTTTGTTGTACAACTA
TTTTTTTTTATTATTATTTTAGTTGTATTTTATTATTTGAAGAGAAGAAA
GTTTGTGCTACAATTTCAACACTGCTTCACAATATTGTCTTATACAGGCA
ATTGGGAAATACATCACTAGAGCGAGACTCCGAATATCTGTCACTTCAAA
AGCCGGTCGAGAACTTCGAATGCGAGAGCTCCATCCAGTACAATGTTTTG
CCCTTGGGAGGAGGAAACGAAGAGGACGAGGAGGATAGTATTGGAGGGGT
GAGCGCTTTTGGCTATGACCTCAAGGAAACTTTCTACACCATCTACAAGT
TTGAGTTTGATAAGACGAAGATGATGAGCAGCCGAGTGGACCACATCCTC
CACGGCAGGGAGTTATTGAAGGCCGAGCCTCACAGGGATTACAAGTTCAG
AAGTGATGCAGTCCTCCCTTGGGGAAGCCTCACCAAGATCAAGAAATGCT
ACTCGAATCAGAATCAAGATGCGGTGCTGCAGCACTTCCAAGATCAGGGA
AGTAATGAGAAAGAAAATACTTTGCGCGAGGTCACCTGGCAGCAAATGC
AGACTTCGTGTCACAAGACGAGCAGAAAGCTTCCTACAGCTTCGCCAACG
TAGCGCCTCAGTGGCAGGCTTTCAACAATGGCAACTGGAAGAAACTTGAG
AACAGAATTCGGACCATTGCCATGAAAAAGGAAGCCACTCTGCGCGTAGT
CACTGGCACCTCCACGGGTCTTCTGAAGCTCAATAGTAGTTCTGGACAAC
TGGAGAACGTGTGCCTGTGTGACGGTGAGCCGCCGTGTGTTCCTCTCTTC
TTTTGGAAGGTGACGCCCGCGTTAAGACAAGCGTTCCTGATGCCTAATCA
TCCTGCCGCGGGAATATCAGCCAGAATTGAAGAACTGGCACATCCTTGTC
CGAATTGGGCAGGTTTCTCTGGAGCCAAGAGAAGACTCGAGGAGCCCTG
TATTGCCTCACCCCAGGCGACCTCTGTGGAGTTGAGCCGAAGGCTTGTGG
ATACAAAGATTTAATGTGAACTCTATATTTGCATTTGAATAACCTTCGTA
CGTCATTTGGTCAAATTTTGCTCTGTGTTTGTATATACAAAATGTCCAGG
AATGGCCAAAGTGCAGAGGTTGGTAAATTCTTAGAGTTCAACCTCGAAG
TTGATACTAATAGTTTTGAAAATTGAAATATATGTTTAACGCAGTTAAAA
AAAAAAAAAAAAAAAAAAAAAAAA
Amino acid composition
                                       (SEQ ID NO: 18)
GKQWYQRRVLVFLFFFGVAAPLCKLEALLLATEKFYESDDTRFIVQTTFC
CTTIFFYYYFSCILLFEEKKVCATISTLLHNIVLYRQLGNTSLERDSEYL
SLQKPVENFECESSIQYNVLPLGGGNEEDEEDSIGGVSAFGYDLKETFYT
IYKFEFDKTKMMSSRVDHILHGRELLKAEPHRDYKFRSDAVLPWGSLTKI
KKCYSNQNQDAVLQHFQDQGSNEKRKYFARGHLAANADFVSQDEQKASYS
FANVAPQWQAFNNGNWKKLENRIRTIAMKKEATLRVVTGTSTGLLKLNSS
SGQLENVCLCDGEPPCVPLFFWKVTPALRQAFLMPNHPAAGISARIEELA
HPCPNWAGFSGAEEKTRGALYCLTPGDLCGVEPKACGYKDLM
```

Glass Shrimp Putative Nuclease:

Source: *Eukaryota; Metazoa; Arthropoda; Crustacea; Malacostraca; Eumalacostraca; Eucarida; Decapoda; Pleocyemata; Caridea; Palaemonoidea; Palaemonidae; Palaemonidae* sp.

```
Nucleic acid composition
                                       (SEQ ID NO: 19)
TGTAGCGTGAAGACGACAGAAGTAATACGACTCACTATAGGGCAAGCAGT
GGTATCAACGCAGAGTACGCGGGCTCCTTGTTCAGAGCTTTAAAGTCATG
GCTGGCAGGAGACAATTCTTCGTCTTATCTTTATATTTCGTGGCCTTTTG
GAACCTTTCCAAAGGTCAAGATTGCGCCTGGGATAAGGATGCAGACTTCC
CACTTACTCCTCCCCTTCTCTTGGATTCTTCCCTCAAGATGATATATCCA
GTGTTAGAGGGATCCCTCAGGATGGTACGAGTAGCAGCTGGCAGCACTAT
CACCGTCGCATGTTCAGGGACGACAATTAGCTGCTCTAGGTCTCGAGGCT
GTTGGAGGGAACCTGTGCTGGCGGCCCAACTGATCACTGGTGATGGCACT
GATAATGCCCTAAATGAGTTGGGATGTGTGACGCCGCATCTGAGAGCTTG
CAGAAGAACCTGGGTGCCTGTGAGATGCAGATCTTGGTACCTCCACGCAG
TAGGATTTAATATTGCCACTACAGGTTCATTCCATGAATTCGAAAGTATA
TGTTTCGATCACGCTGCAGAGACTACTCTATACACAAAGCATACTCTCCA
TGGAGCCAACATCATAGCCAAAGACGTGGATCCTAGCAGACCACCCTTCA
AGCCCGATACTGGATTCTTCACGGTCGAAGTCAATACCGTTTATACTCAG
GCTTCACAGCTGGCCTTGATGGAACAGCTGCTTGGTGATTCTGCACTGGC
CAACCAGATCATTAATCCAGATCAAGAGCTGTTCATGTCTAGAGGTCACC
TCTCTCCAGATGCTGACCATGTACTGATAGCTGAACAAGACGCAACTTAT
TACTTCATTAACGTTATGCCTCAGTGGCAGGCATTTAATAATGGAAACTG
GAAGTACTTGGAATTTGCTGGCAGAGATCTTGCTGTAGCCCACGGCACTG
ACCTGACCGTCTACGATGGAGGTTGGGGAGTGCTGGAACTGGATGACATT
AATGGAAATCCAGTACAGATTTACCTGGGACTCAGTGAAGGCAAAGAAGT
TGTTCCAGCGCCTGCTCTCATGTATAAGATTCTGCACGAAGAAAGCACTA
ACCGAGCTGCAGCTGTTATAGGCATCAACAACCCCCACATTACAGTGGCT
CCAACTCCTATTTGCACTGATATCTGCTCCAGTCTTACATGGATTGACTT
CGACATTACTGACCTCTTCCGTGGTTTTACATACTGCTGCACCGTTGATG
ATCTCAGAGCAGCCATTCCTCACGTTCCTGATCTTGGAAATGTTGGTCTT
TTGGACAGTTAAACATCCGTGACACTCTGTGAAAGAGGATCAGTTGTCGT
GGGAATTGTTATAAATGAATAAATAATGACTACAGTAAAAAAAGAAAAAA
```

-continued

```
AAAAAAAAAAAAAA
```

Amino acid composition (SEQ ID NO: 20)

```
MAGRRQFFVLSLYFVAFWNLSKGQDCAWDKDADFPLTPPLLLDSSLKMIY

PVLEGSLRMVRVAAGSTITVACSGTTISCSRSRGCWREPVLAAQLITGDG

TDNALNELGCVTPHLRACRRTWVPVRCRSWYLHAVGFNIATTGSFHEFES

ICFDHAAETTLYTKHTLHGANIIAKDVDPSRPPFKPDTGFFTVEVNTVYT

QASQLALMEQLLGDSALANQIINPDQELFMSRGHLSPDADHVLIAEQDAT

YYFINVMPQWQAFNNGNWKYLEFAGRDLAVAHGTDLTVYDGGWGVLELDD

INGNPVQIYLGLSEGKEVVPAPALMYKILHEESTNRAAAVIGINNPHITV

APTPICTDICSSLTWIDFDITDLFRGFTYCCTVDDLRAAIPHVPDLGNVG

LLDS
```

Mangrove Fiddler Crab Putative Nuclease:

Source: *Eukaryota; Metazoa; Arthropoda; Crustacea; Malacostraca; Eumalacostraca; Eucarida; Decapoda; Pleocyemata; Brachyura; Eubrachyura; Ocypodoidea; Ocypodidae; Ocypodinae; Uca complex; Uca; Uca crassipes*

Nucleic acid composition (SEQ ID NO: 21)

```
AAGCAGTGGTATCAACGCAGAGTACGCGGGGGGGAGAAGCACTGCGCTGA

GAGAAGCAGAGAGGAAATGGATCTCCGACGAAGATTCTCCCGGACCTTAC

AACTGGTAGTCCTTCTCTTCGCCTGTGCAAGCAATTGCTTTGGATGCGAG

TGGGACAAAGACTTGGACTTCCCTGAACACCCGCCGCTCATCATTAACAA

CCAGCTAGATTTCGTGCTGCCGGTGTTGGAGGGAGTCAACAGGGTGGTGA

GGGTGGCAGAGGGAGAAACCGTGACTCTGGCGTGCTCTGGTAGCGAGTTG

GTAAATCTTGGGGAAGCAGAGGTGCAGGCTCGGTGCCTCAGCAGTGGCCT

CCTAACGATCGGTGATGCAGAGTGGGACTTGGcGAGCCTtGGTTGCagCA

GTGATGTAAAAGAGACCATTTTCCGCGACCTGGGGACCTGCGGCGCCGGT

GGTGTCGGGATCCTAAATGGCATTGGCTTCCAGATTTTCAGTCTCAACTA

CGACAAAGTGATCATTAACGTTTGCTTCGAAGCAGCTTCCGAGACGACCC

TCTTCACTGATCACATCCTCCACGGCGCCGACATCGCCGCTAAGGACGTA

GAGGCGTCCAGGCCGTCCTTTAAGACTTCCACAGGGTTCTTCAGTGTCTC

TATGAACACCGTGTATTCGCAGAACTCGCAACTCCAACTCATGACTAGTA

TTCTCGGAGACGAGGACCCCGCCAATACAATTATTGACCCTTCCAAACAA

CTATACTTCGCAAAGGGTCACATGTCTCCTGACGCCGGTTTCGTGACTAT

AGCAAGCCAGGATGCCACCTATTACTTCATCAATGCCTTGCCACAGTGGC

AGGCCTTCAACAATGGCAACTGGAAGTATCTGGAGACTAACACGCGAAAT

CTGGCAATGAAGAAGGGACGCGACCTTCGGGTGTACAGTGGTGGGTGGGA

TGTCCTGGAGCTGGACGACATTAATGGCAATCCCGTGAAGGTCTTCCTGG

GACTGACAGAAGGCAAGGAGGTAGTGCCCGCGCCTGCCATCACCTGGAAG

GTGGTACACGATGAGTCCACTAACTGCGCCGTGGCCGTAGTGGGCGTCAA

CAACCCGCATCTCACCGCCGCCCCCGCCACGCTTTGTGAAGACCTGTGTT

CCTCGCTCTCCTGGATCACCTTCGACGTTAGCAGTCTCGCAAGCGGGTAC

ACCTACCGCTGTTCCGTGGCGGAACTGCGCGCCTCGGTGCCCCACGTTCC

TGACTTAGGCAATGTCTGTCTTCTCACCGACTAAAGACGAAACACATGTT

GGAGTCACCCAGTAAATGGACAGTGGTGACATCAGGTTGACCTAATCATA

ATAGTGTCATCATGCTAAAAAAAAAAA
```

Amino acid composition (SEQ ID NO: 22)

```
MDLRRRFSRTLQLVVLLFACASNCFGCEWDKDLDFPEHPPLIINNQLDFV

LPVLEGVNRVVRVAEGETVTLACSGSELVNLGEAEVQARCLSSGLLTIGD

AEWDLASLGCSSDVKETIFRDLGTCGAGGVGILNGIGFQIFSLNYDKVII

NVCFEAASETTLFTDHILHGADIAAKDVEASRPSFKTSTGFFSVSMNTVY

SQNSQLQLMTSILGDEDPANTIIDPSKQLYFAKGHMSPDAGFVTIASQDA

TYYFINALPQWQAFNNGNWKYLETNTRNLAMKKGRDLRVYSGGWDVLELD

DINGNPVKVFLGLTEGKEVVPAPAITWKVVHDESTNCAVAVVGVNNPHLT

AAPATLCEDLCSSLSWITFDVSSLASGYTYRCSVAELRASVPHVPDLGNV

CLLTD
```

II. DSN Preference (DSNP) Assay

Methods of Detection of the Sequence(s) and Sequence Variants in Nucleic Acid Samples A. General Description Under certain conditions, the subject nucleases specifically recognize and cut perfect short DNA/DNA (and/or DNA/RNA) duplexes with higher activity then non-perfect duplexes of the same length. Thus, subject nucleases are capable of discriminating between a single nucleotide mismatch in the short duplex (which is not cut by the enzyme) and a perfect duplex (which is cut by the enzyme) (FIG. 1). This ability of subject nucleases in the employed in the methods for detection of nucleic acid sequence(s) and sequence changes including single base is described below.

Figure 8:
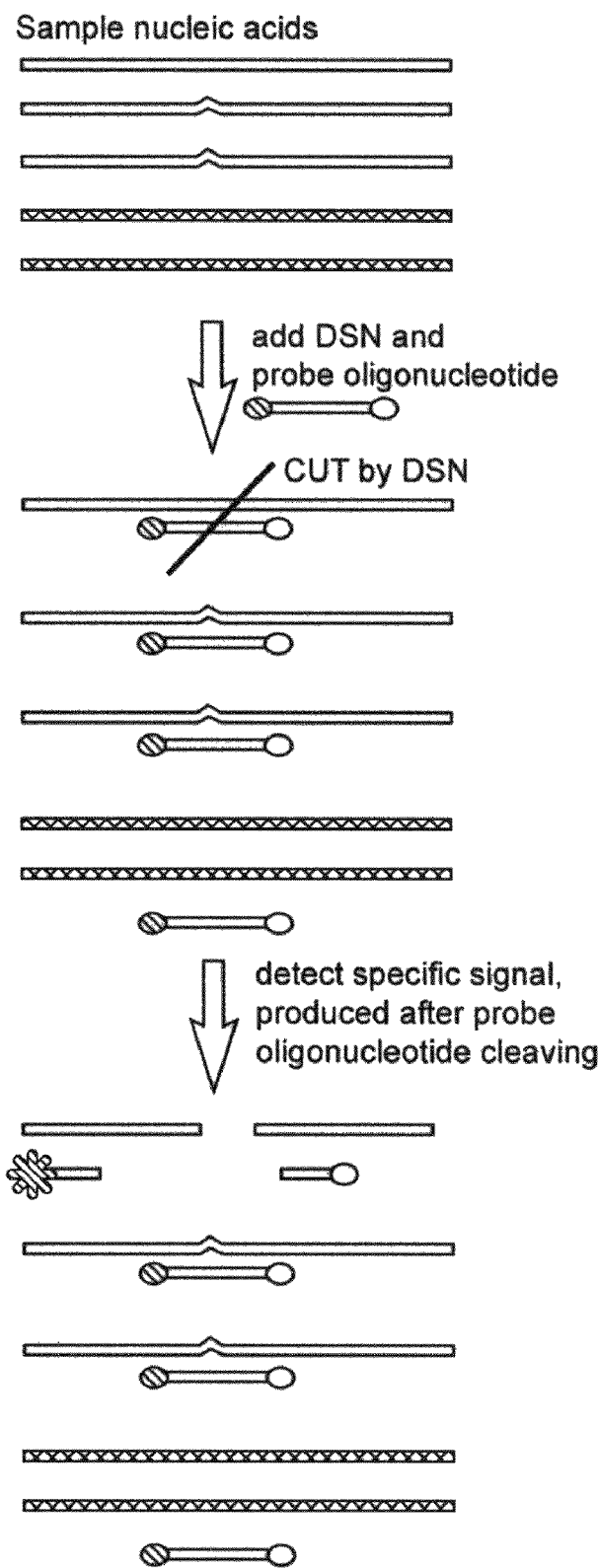
FIG. 8 provides a schematic diagram of detection of a nucleic acid sequence of interest (gray line) in a complex nucleic acid sample that also includes nucleic acids comprising a sequence of interest with one nucleotide change (gray broken line) and nucleic acids without a sequence of interest (black line).

A schematic diagram of the DSNP assay is provided in FIG. 8. In these methods, the sample of nucleic acids to be tested is mixed with subject nuclease and labeled probe oligonucleotide. Probe oligonucleotide can form perfectly matched duplexes with sequence (or sequence variant) of interest. In certain embodiments, probe oligonucleotide is labeled by fluorescent donor and fluorescent quencher (or acceptor) pair and can generate specific signal after cleaving. In other embodiments, probe oligonucleotide is labeled by another label known in the art as described previously.

The resultant mixture is incubated under conditions sufficient for generation of the duplexes between target sample nucleic acids and probe oligonucleotide. The perfectly matched duplexes generated are cleaved by the subject nuclease. Examples of the appropriate conditions are described in details in Examples section below.

After incubation, the cleaving of the probe oligonucleotide is examined. The manner in which the cleaved oligonucleotide probes are detected necessarily depends on the nature of the oligonucleotide probe label. For example, where the detectable label is an isotopic label positioned at one end of the probe, one can assay for detectably labeled fragments that are shorter than the full-length probe size and, in this manner, detect the presence of cleaved probes. In certain embodiments, the change of the fluorescence intensity of the testing sample is measured and compared with the change of the fluorescence intensity of the positive and negative control samples that are known to comprise or not comprise sequence of interest. The fluorescence intensity change in the testing sample that exceed the fluorescence intensity change in the negative control and comparable with fluorescence intensity change in the positive control sample support is an indication of the presence of the sequence of interest in the testing sample.

Figure 9:
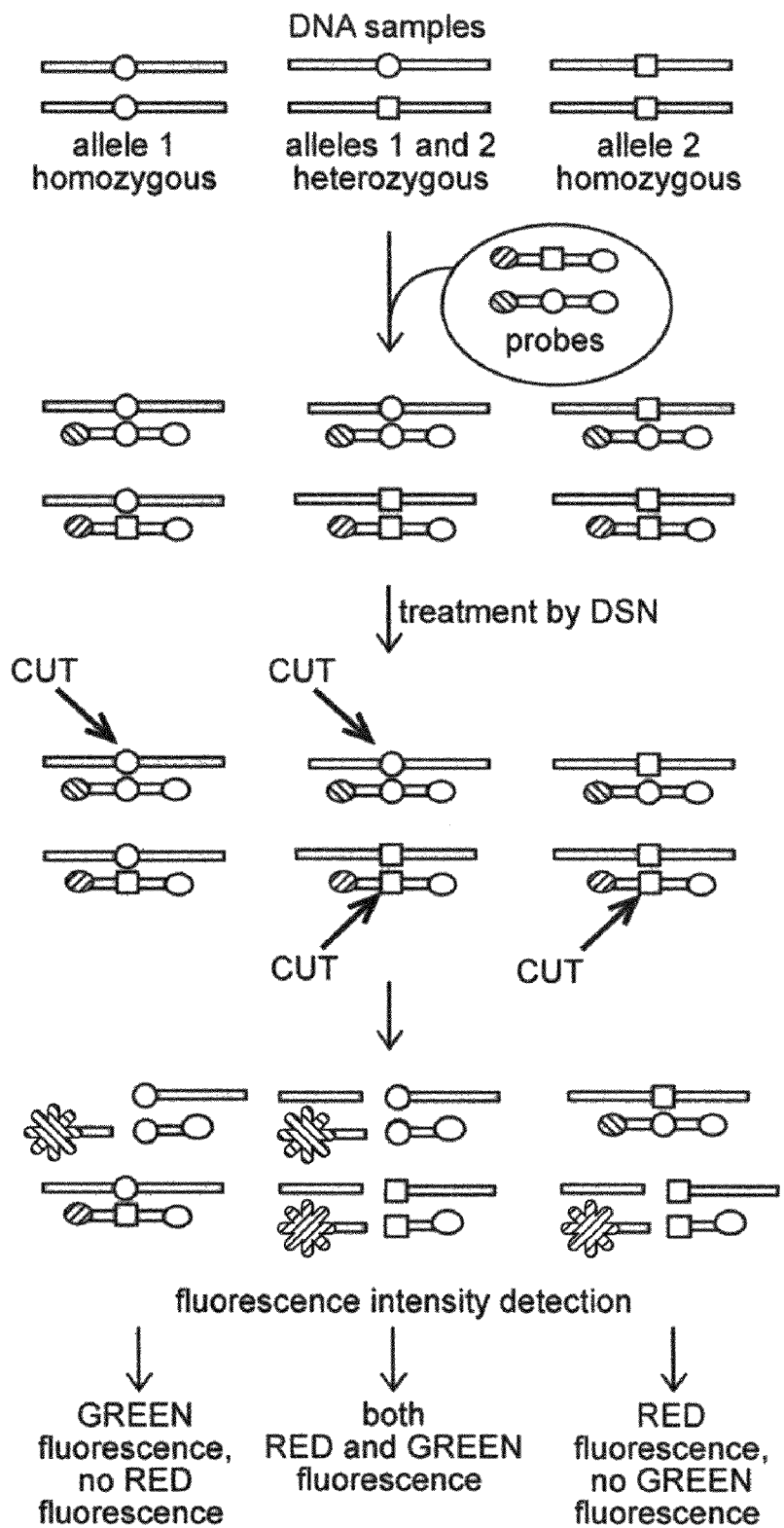
FIG. 9 provides a schematic diagram of an DSNP assay with two fluorescence labeled probe oligonucleotides for detection of two sequence variants in nucleic acid samples. Gray circles indicate quenching agent, red and green circles indicate fluorescence donors. Red and green asterisks indicate fluorescence signal that is generated after fluorescence oligonucleotide cleavage using a nuclease according the subject invention. Blue circle and square indicate the variable nucleotide position.

As mentioned above, the above general methods can be used to detect the presence of a single nucleic acid sequence variant of interest in a sample or a plurality of different nucleic acid sequences in a sample (e.g. for testing both allelic variants at one or for testing several microbial strains, etc.). When a plurality of different nucleic acid sequence variants are to be detected in one tube, a specific probe oligonucleotide for each sequence (sequence variant) to be detected is used. In this case, the only limitation is that a labeling system, i.e., signal producing system of one or more entities, should be employed that provides for ready differentiation of different oligonucleotide probes to different target nucleic acid sequence variants (FIG. 9). Alternatively, in the case of the array of the subject invention (described below), the oligonucleotides may contain a same label, because the signals for different sequence variants would be different by their positions.

For these DSNP assay methods, the following starting materials may be used:

1—Nucleic Acid Sample Containing Sequence(s) of Interest.

The nucleic acid sample being analyzed can be obtained from any source and can be obtained from these sources using standard methods. The sample might include single-stranded DNA or double-stranded DNA (e.g. genomic DNA) in linear or circular form. Depending on the particular interest, the sample may be treated by different methods known in the art, e.g. mechanical shearing, restriction enzyme digest, etc. In some embodiments, the sample may be from a synthetic source. In some embodiments, nucleic acids in the sample may be amplified by PCR or other methods known in the art. In some embodiments, nucleic acids to be tested are RNA, natural or synthesized (for example synthesized from T7 promoter-containing PCR amplified DNA by known methods). In some embodiments, in this case the prior step is preparation of the first strand cDNA that may be performed using any method known in the art. In other embodiments. In other embodiments, nucleic acid sample is RNA that is used directly from its naturally occurring source or synthesized. In certain embodiments, region comprising sequence(s) of interest is amplified by PCR using specific PCR primers. The length of the PCR product may vary, but usually range from 10 to 1000 bp, more usually from 60 to 500 bp.

2—Subject Nuclease.

A variety of different nucleases may exhibit the specific properties described above under specific cleavage conditions and thus may be employed in the subject methods. Representative nucleases of interest include but are not limited: cation-dependent endonucleases from different sources including DNAase K from Kamchatka crab (Menzorova, et al., Biochemistry (Moscow), vol. 58 (1993) (in Russian) pp. 681 to 691; Menzorova, et al., Biochemistry (Moscow), vol. 59 (1994) pp 321 to 325), Dnase I family members (like well known bovine DNAase I) (Liao T H. Mol Cell Biochem 1981 Jan. 20; 34(1):15-22), non-specific nucleases like shrimp nuclease (Chou & Liao; Biochemica et Biophysica Acta, vol. 1036 (1990) pp 95 to 100; Lin et al., Biochemica et Biophysica Acta, vol. 1209 (1994) pp 209 to 214; Wang et al., Biochem. J., vol 346 (2000) pp 799 to 804), and $Ca^{2+}$, $Mg^{2+}$-dependent endonuclease from sea-urchin (Menzorova, N. I., Rasskazov, V. A. Biokhimiia (Rus) 1981; vol 46 pp 872 to 880), and the like. Of particular interest in many embodiments are the novel specific nucleases described herein, including the crab duplex-specific nuclease (crab DSN).

3—Buffer for the subject nuclease (DSN Buffer).

4—Probe oligonucleotides.

The specific complementary short oligonucleotide is designed for each sequence or sequence variant to be tested. The length of the probe oligonucleotide typically range from 9 to 30 nt, usually 10-15 nt if nucleic acid samples are DNA and 15-20 nt if nucleic acid samples are RNA. Each probe oligonucleotide is labeled by detectable label as known in the art. Preferably labeling is performed using fluorescence donor and quenching agent (or fluorescence acceptor). Preferably the oligonucleotide probes are labeled using fluorescence donors with different color to generate sequence-specific fluorescence after cleaving. In other words, each probe oligonucleotide is labeled to generate fluorescence at specific wavelengths after cleaving.

The primers and oligonucleotides used in the methods of the present invention are DNA, and can be synthesized using standard techniques.

B. Examples of DSNP Assay.

1. Detection of Point Mutations (SNPs) on DNA Samples (e.g. cDNA or Genomic DNA) in Solution with Fluorescence—Labeled Oligonucleotide Probes.

1.1. Initially, the DNA fragments containing the SNP site of interest are amplified by PCR. Following amplification, an aliquot of the PCR reaction is mixed with DSN and with two probe oligonucleotides labeled with the fluorescence donor (at the 5' end) and quencher (at the 3' end). Each signal probe generates fluorescence at specific wavelengths after cleaving. The first oligonucleotide is complementary to the wild-type sequence, while the second is complementary to the mutant sequence. The mixture is incubated with DSN during which the nuclease cleaves the PCR product to generate short DNA fragments that can effectively hybridize with signal probes. All perfectly matched duplexes generated by the DNA template and signal probes are cleaved by DSN to generate sequence-specific fluorescence. Incubation conditions are dependent at least in part on probe oligonucleotide length and compositions. In certain embodiments (when 10 nt probe oligonucleotides is used), the incubation is performed at temperature range from 29 to 37° C. (e.g. at 35° C.) for a period 2-6 h (or longer).

1.2. To improve signal intensity, the DSN cleavage reaction in the method described in section 1.1 is performed in the presence of exonuclease-deficient Klenow fragment (KF(exo-)), which catalyzes strand displacement DNA synthesis by extension of the 3'-ends generated in the PCR fragment upon DSN nicking activity. Displaced DNA strands are involved in a genotyping reaction that results in a 5-20 times increase in the specific fluorescent signal. In certain, the incubation is performed at temperature range from 29 to 37° C. (e.g. at 35° C.) for a period 30 min-2 h.

1.3. Initially, the DNA fragment containing the SNP site of interest is amplified by PCR. Following amplification, an aliquot of the PCR reaction is mixed with DSN and with two fluorescence-labeled oligonucleotide probes as in section 1.1.

The resulted mixture is incubated at temperature of fragmentation that is optimal for DSN cleaving (usually from 50 to 65° C.) for period sufficient for cleaving of the PCR product to generate short DNA fragments (usually from 7 to 20 nt). The incubation time may vary, but usually ranges from 10 min to 1 h, more usually 20-30 min. After, the resultant mixture is incubated at annealing temperature (usually 35° C. for 10-mer oligonucleotide probes) for a period sufficient for hybridization of probe oligonucleotides and target nucleic acid fragments and for cleaving of all perfectly matched duplexes generated. The incubation time may vary, but usually ranges from 5 min to 2 hrs, more usually from 10 to 30 min.

This method can be employed to either qualitatively or quantitatively detect the ratio of the mutant and wild-type sequence variants in the sample. The ratio of two labels reflects the ratio of mutant nucleic acids and wild type nucleic acids in the sample.

1.4. The PCR products (obtained as described in previous examples) are first incubated with DSN at temperature of fragmentation without probe oligonucleotides. Probe oligonucleotides are added to the reaction during or after this step and the resultant mixture is incubated at annealing temperature.

This method can be employed to either qualitatively or quantitatively detect the ratio of the mutant and wild-type sequence variants in the sample. The ratio of two labels reflects the ratio of mutant nucleic acids and wild type nucleic acids in the sample.

1.5. In the methods described above (sections 1.1 to 1.4), two fluorescent dyes are employed to distinguish between wild-type and mutant sequences in one tube. However, the assays may be also performed when both probe oligonucleotides generate one type of fluorescence. In this case, wild-type and mutant sequence-specific probe oligonucleotides are mixed with DNA substrates in two separate tubes.

1.6. In some cases (e.g. DNA samples with low complexity), the initial PCR amplification step may be excluded from the methods described above (sections 1.1 to 1.5). For example, plasmid DNA comprising sequence of interest may be tested in DSNP assay directly without PCR amplification. Purified PCR products may also be used in the assay.

The SNP detection using DSNP assay was examined on several models, using homozygous and heterozygous DNA samples. All the results obtained with the DSNP assay were confirmed by DNA sequencing.

The DSNP assay variant described in the section 1.1 was performed on two PCR fragments of 144 bp that are different in one nucleotide position were prepared: First sequence—FTnormD—agtacgctcaagacgacagaagtacgc-ccgggcgtactctgcgttgttaccactgctggagctccaattcgc ctatagt-gagtcgtattattctgtcgtcttcacgctaca (SEQ ID NO:23) and Second sequence—TT79cD—agtacgctcaagacgacagaag-tacgcccgggcgtactctgcgttgttaccactgctttggagctccaattcgcc ctg-tagtgagtcgtaftattctgtcgtcttcacgctaca (SEQ ID NO:24). Each fragment was amplified to concentration of about 10 ng/mkl and then mixed with pair of fluorescently labeled oligonucleotides: TT79cD sequence specific 5'-TAMRA-GCCCTG-TAGT-DABCYL-3' (SEQ ID NO:25) and FT7normD sequence specific 5'-Fluorescein-GCCCTATAGT-DAB-CYL-3' (SEQ ID NO:26). Reaction mixture (20 mkl) containing 15 mkl PCR reaction (in Advantage KlenTaq Polymerase buffer, Clontech), 5 mM MgCl$_2$, 0.25 mkM each labeled oligonucleotide, 0.4 Kunitz-units crab DSN was incubated at 30° C. for 3 h. Analysis of resulted fluorescence showed strong FT7normD specific signal in FT7normD sequence-containing sample and TT79cD-specific signal in TT79cD sequence-containing sample (FIG. 10).

To demonstrate the DSNP assay on PCR products with different size, PCR products of 952, 534 and 69 bp comprising C- or T-variants of the 7028 C-T mitochondrial polymorphous site (in COX1 gene) were generated and used with a T-variant specific probe oligonucleotide in the DSNP assay as described in the section 1.2. PCR reactions were performed with the Advantage 2 PCR Kit (Clontech). Each PCR reaction (25 µl) contained 1×Advantage 2 Polymerize mix (Clontech), 1×reaction buffer, 200 µM dNTPs, 0.3 µM each gene-specific primer and 10 ng human total DNA. Fragments (69, 534, and 952 bp) comprising the 7028 C-T site of the COX1 gene were amplified using three pairs of primers at the following positions: Dir1-(6540-6559) and Rev1 (7492-7473); Dir2 (6792-6811) and Rev2 (7345-7326); Dir3 (6991-7010) and Rev3 (7060-7041) (primer positions are specified according to GenBank Accession Number NC_001807). In each case, 26 PCR cycles were performed at 95° C. for 7 s, 63° C. for 20 s and 72° C. for 30 s.

Figure 11:
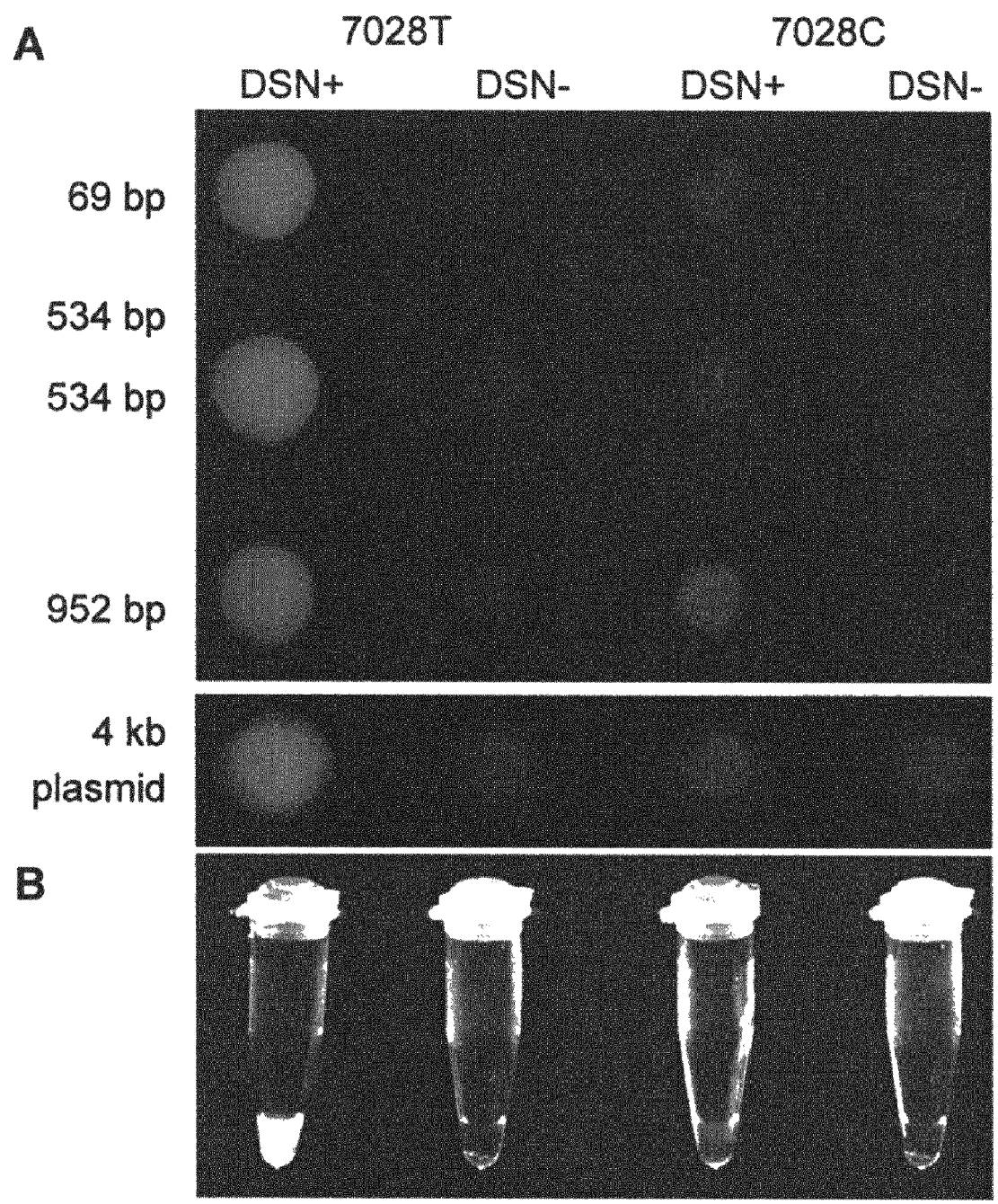

For genotyping reaction, in each case, a 5 µl aliquot of PCR products containing about 75 ng DNA was mixed with 1.5 µl 10×KF(exo-) buffer (Fermentas MBI), probe oligonucleotide 5'-Fl-gtgAgctaca-DABCYL-3' (SEQ ID NO:27) (to a final concentration of 0.3 µM), 0.5 Kunitz unit crab DSN, 2 U KF(exo-) (Fermentas MBI) and milliQ water (to a final volume of 15 µl), and incubated for 1 h at 35° C. Clear results were obtained with all PCR products as shown at photographs (FIG. 11). Photographs were obtained using an Olympus SZX12 fluorescent stereomicroscope (FIG. 11A) and using a Multi Image Light Cabinet (Alpha Innotech Corporation) under UV light (FIG. 11B).

The DSNP assay scheme without PCR stage (as described in the section 1.6) was demonstrated with plasmid DNA (about 4 kb) comprising a 69 bp COX1 fragment (FIG. 11A). For genotyping reaction, 5 mkl containing about 500 ng plasmid DNA in 1×DSN buffer was mixed with 1.5 µl 10×KF (exo-) buffer (Fermentas MBI), probe oligonucleotide 5'-Fl-gtgAgctaca-DABCYL-3' (SEQ ID NO:28) (to a final concentration of 0.3 µM), 0.5 Kunitz unit crab DSN, 2 U KF(exo-) (Fermentas MBI) and milliQ water (to a final volume of 15 µl), and incubated for 1 h at 35° C. Photographs were obtained using an Olympus SZX12 fluorescent stereomicroscope.

Figure 12:
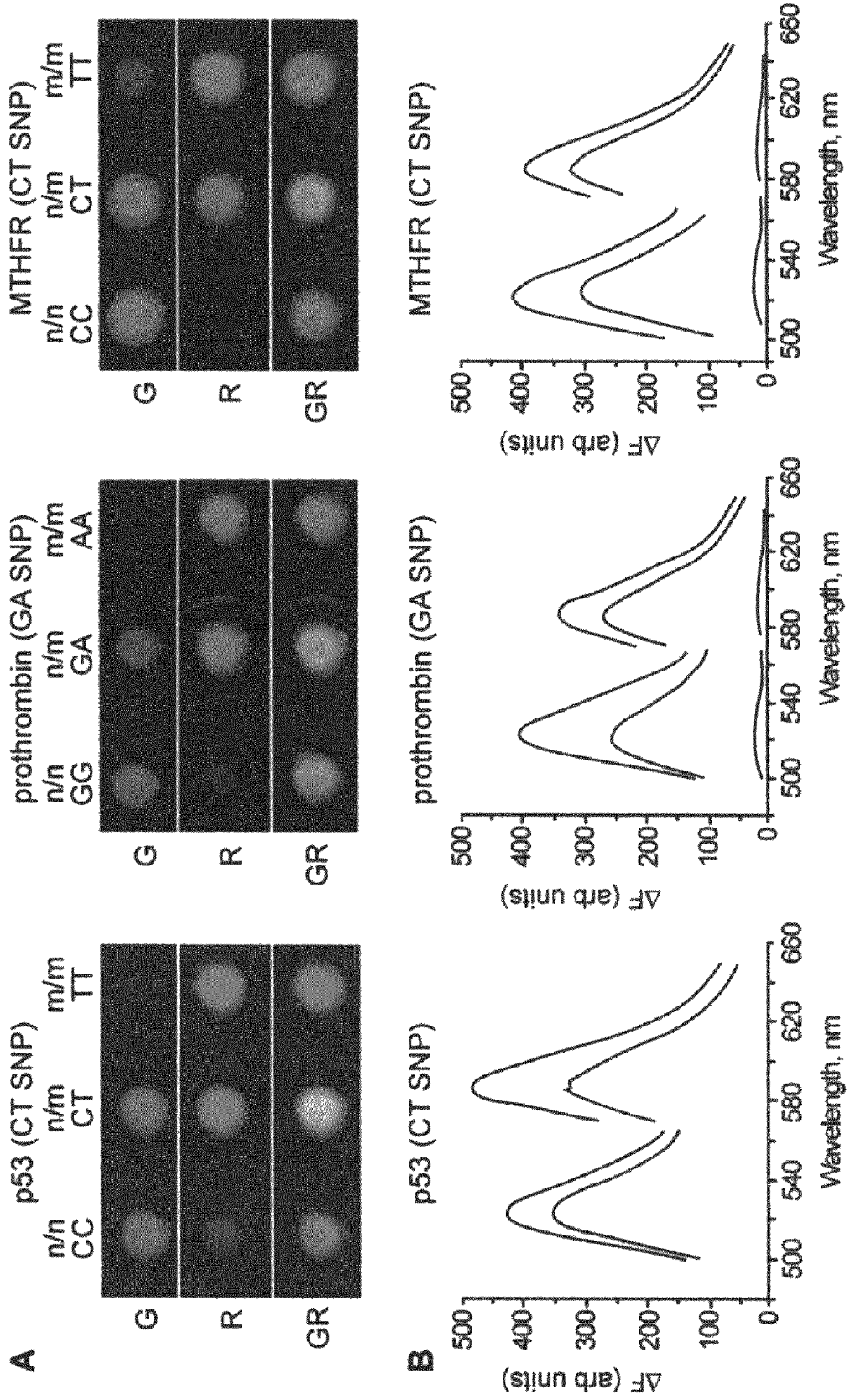

We further employed the DSNP assay (described in the section 1.2) with two fluorescent dyes to detect specific polymorphisms in genetic loci contributing to susceptibility to some diseases. We analyzed prothrombin 20210 G-to-A polymorphism associated with an increased risk of venous thrombosis and myocardial infarction (Poort, S. R., Rosendaal, F. R., Reitsma, P. H., Bertina, R. M. Blood 1996, 88: 3698-3703), C677T polymorphism of the MTHFR gene associated with increased levels of total plasma homocysteine, a risk factor for coronary artery disease (Frosst, P., Blom, H. J., Milos, R., Goyette, P., Sheppard, C. A., Matthews, R. G., Boers, G. J., den Heijer, M., Kluijtmans, L. A., van den Heuvel, L. P., et al. Nat. Genet. 1995, 10: 111-113), and p53 C309T polymorphism associated with carcinomas (Abarzua, P., LoSardo, J. E., Gubler, M. L., Neri, A. Cancer Res. 1995, 55: 3490-3494) in homozygous and heterozygous DNA samples (FIG. 12). DSNP assay was performed as described in example 1. The following PCR conditions and gene-specific primers were employed: p53 (C309T polymorphism): 30 PCR cycles (95° C. for 7 s; 65° C. for 20 s; 72° C. for 20 s) were performed with primers 5'-aaggggagcctcaccacg-3' (SEQ ID NO:29) and 5'-ccacggatctgaagggtgaa-3' (SEQ ID NO:30); prothrombin (20210 G-to-A polymorphism): 30 cycles (95° C. for 7 s; 63° C. for 20 s; 72° C. for 20 s), primers 5'-atggttcccaataaaagtgac-3' (SEQ ID NO:31) and 5'-aatagcactgggagcattga-3 (SEQ ID NO:32); MTHFR (C677T polymorphism): 30 PCR cycles (95° C. for 7 s; 63° C. for 20 s; 72° C. for 20 s), primers 5'-cttgaaggagaaggtgtctg-3' (SEQ ID NO:33) and 5'-aagaaaagctgcgtgatgatg-3' (SEQ ID NO:34). The following signal probes were used: p53 (C309T polymorphism): p53WT (wild-type-specific)-5'-Fl-tggGcagtgc-DABCYL-3' (SEQ ID NO:35) and p53M (mutant-specific)-5'-TAMRA-tggAcagtgc-DABCYL-3' (SEQ ID NO:36); prothrombin (20210 G-to-A polymorphism): F2WT-5'-Fl-gctCgctgag-DABCYL-3' (SEQ ID NO:37) and F2M-5'-TAMRA-gctTgctgag-DABCYL-3' (SEQ ID NO:38); MTHFR (C677T polymorphism): MTHFRWT-5'-Fl-tcgGctcccg-DABCYL-3' (SEQ ID NO:39) and MTHFRM-5'-TAMRA-tcgActcccg-DABCYL-3' (SEQ ID NO:40).

Figure 13:
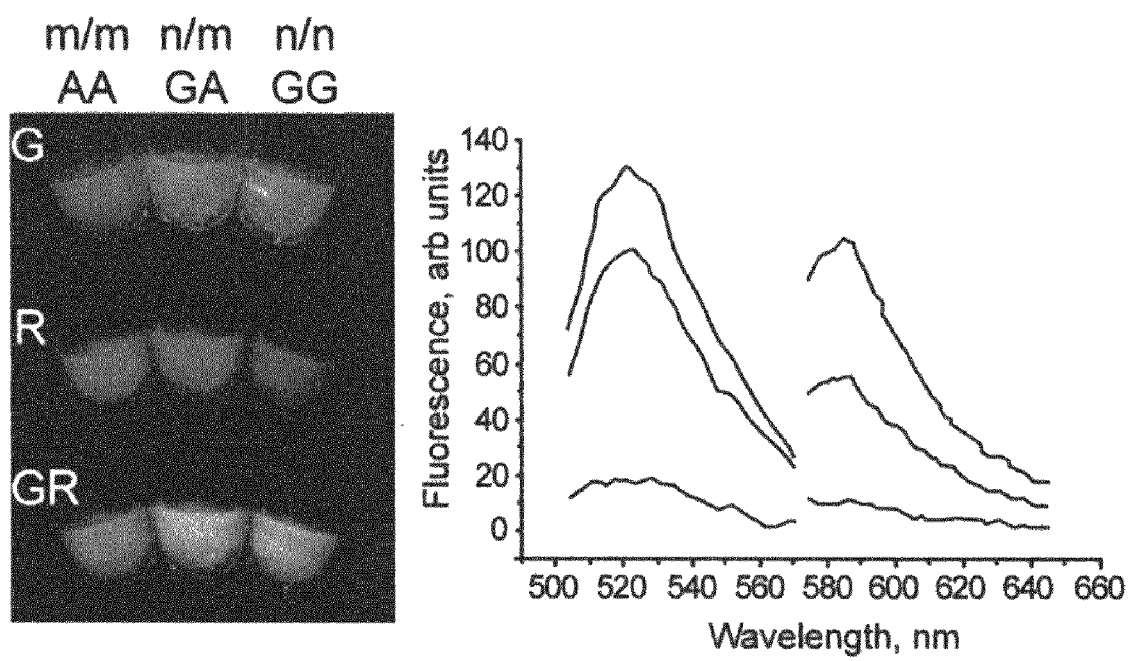

DSNP assay described in the section 1.3 was used for testing of the Factor V Leiden polymorphism G1691A in homozygous and heterozygous DNA samples (FIG. 13). Leiden mutation in factor V gene (Bertina et al., Nature 1994; 369: 64-7) is the most common genetic abnormality associated with hereditary thrombophilia. DNA samples were used for PCR with factor V specific primers (5'-tactaatctgtaagag-cagatc-3' (SEQ ID NO:41) and 5'-gttacftcaaggacaaaatacc-3' (SEQ ID NO:42)) as described in example 1. A 5 µl aliquot of PCR products containing about 75 ng DNA was mixed with 1.5 µl 10×DSNP buffer (1× buffer contains 50 mM Tris-HCl, 8.0 and 5 mM $MgCl_2$), probe oligonucleotides (to a final concentration of 0.3 µM), 1 Kunitz unit DSN and milliQ water (to a final volume of 15 µl), and incubated for 15 min at 60° C. and 10 min at 35° C. Fluorescence intensity was measured on a spectrofluorimeter Cary Eclypse (Varian). Plates were photographed using an Olympus SZX12 fluorescent stereomicroscope. The following probe oligonucleotides were used: FV-WT 5'-Fl-aggcgaggaa-DABCYL-3' (SEQ ID NO:43) and FV-M 5'-TAMRA-aggcaaggaa-DABCYL-3' (SEQ ID NO:44).

Figure 14:
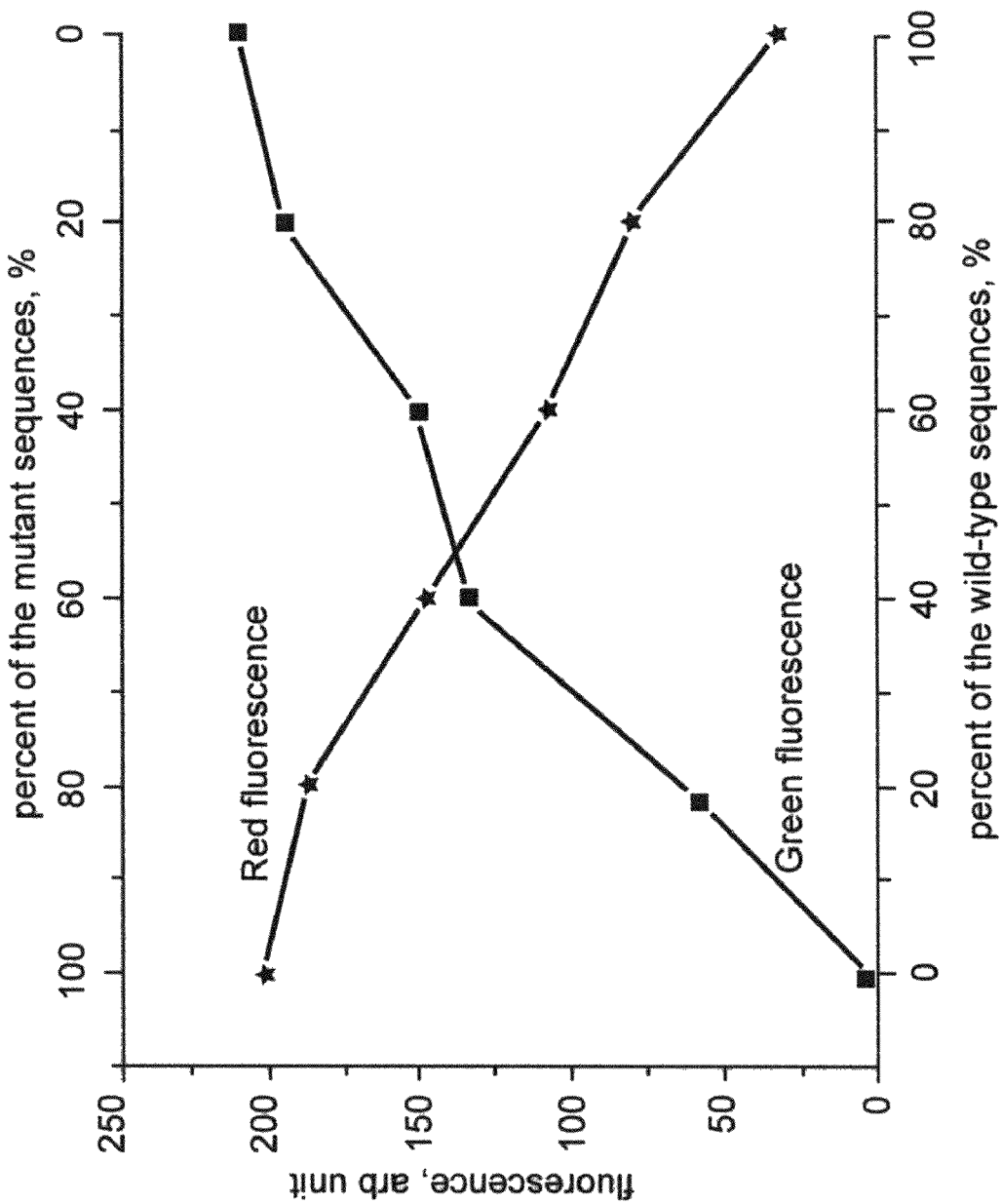

Quantitative testing using DSNP assay as described in the section 1.3 was also demonstrated (FIG. 14).

DNA samples containing normal and mutant sequence of the ApoE gene (position 388) were used for PCR with ApoE specific primers (5'-gcggacatggaggacgt-3' (SEQ ID NO:45) and 5'-ggcctgcacctcgccgcggta-3' (SEQ ID NO:46)). Resulted PCR amplified fragments were mixed in different proportions as follow:

| Sample number | Normal sequence, % | Mutant sequence, % |
|---|---|---|
| 1 | 100 | 0 |
| 2 | 80 | 20 |
| 3 | 60 | 40 |
| 4 | 40 | 60 |
| 5 | 20 | 80 |
| 6 | 0 | 100 |
| 7 (negative control) | 0 | 0 |

A 5 µl aliquot of PCR products containing about 50 ng DNA was mixed with 2 µl 10×DSNP buffer, probe oligonucleotides (to a final concentration of 0.25 µM), 1 Kunitz unit DSN and milliQ water (to a final volume of 20 µl), and incubated for 15 min at 60° C. and 10 min at 35° C. The following probe oligonucleotides were used: ApoEWT 5'-Fl-cgtgcgcggc-DABCYL-3' (SEQ ID NO:47) and ApoEM 5'-TAMRA-cgt-gtgcggc-DABCYL-3' (SEQ ID NO:48). Fluorescence intensity was measured on a spectrofluorimeter Cary Eclypse (Varian).

2. Detection of Nucleic Acid Analytes in DNA Samples (e.g. cDNA or Genomic DNA) in Solution with Fluorescence—Labeled Oligonucleotide Probes.

DSNP assay is applicable for the nucleic acid analyte detection (for expression profiling, detection of the bacterial or viral species and strains in complex DNA samples, e.g. for diagnostic purpose, detection of a specific PCR products in the PCR mixture without electrophoresis, etc.) For analysis of each nucleic acid analyte a short oligonucleotide, that is capable to hybridize nucleic acid analyte, is used. The oligonucleotide is labeled at each end by a fluorescence donor and quenching agent pair. The DSNP assay for nucleic acid analyte detection is carried out using any protocol described in the previous section (section 1 of the Examples). In certain embodiments, the prior amplification of the fraction enriched in the sequence(s) of interest is performed, e.g. using PCR with gene-specific primers. The detection of a signal level that exceeds the signal level in sample incubated without nuclease is an indication of the presence of the nucleic acid analyte in sample.

To quantitative assessment of the nucleic acid sequence in the sample, there are two variants: (1) introduction in the nucleic acid sample the endogenous nucleic acid (control nucleic acid) in known concentration; (2) using the nucleic acid of known concentration that is present in a sample as control nucleic acid. For quantitative analysis the oligonucleotide specific to the control nucleic acid, which is preferably labeled by another label then label for nucleic acid analyte, is added to reaction mixture. Comparison in cleavage rate of these oligonucleotides allow to define quantity of nucleic acid analyte in the sample. If both oligonucleotides are labeled by the same label, analysis may be performed at separate reactions.

3. DSNP Assay on RNA Samples in Solution with Fluorescence—Labeled Oligonucleotide Probes.

The DSNP assay is also applicable for detection of sequences or sequence variants directly in RNA nucleic acids. As example, RNA to be analyzed is a synthetic RNA prepared using transcription from T7 promoter. In this method, 50-150 nt RNA containing the sequence(s) of interest is mixed with fluorescence labeled sequence-specific probe oligonucleotide(s) of 15-25 nt long. Cleavage reaction is performed in 15-20 mkl containing 50 mM Tris-HCl (pH range from 7.5 to 8), at least 100 ng RNA, 5-7 mM $Mg^{2+}$, 0.3 mkM of each labeled probe oligonucleotide, 0.4-1 Kunitz-units of DSN. SNP detection is performed as described in the section 1.1 of the Examples.

Figure 16:
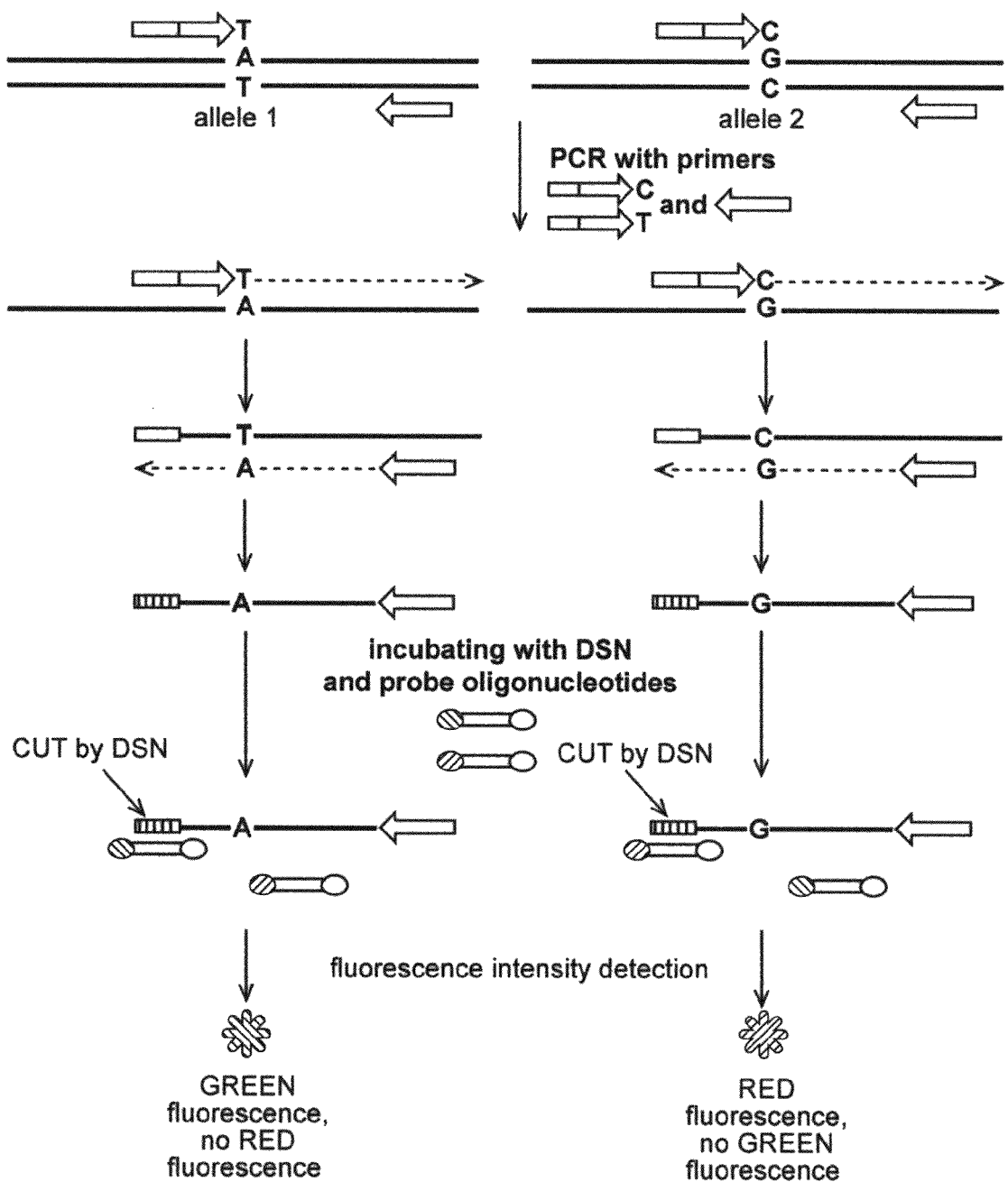
FIG. 16 provides a schematic diagram of a DSN using in the allele-specific amplification methods. Grey circles indicate the quenching agent, green and red circles—fluorescence donors. The green and red asterisks indicate the fluorescence label generated after probe oligonucleotide cutting by a nuclease according to the subject invention. Blue and black squares indicate the universal sequences in the allele-specific primers and probe oligonucleotides.

The method was tested in a model experiment (FIG. 15). Fragment of p53 cDNA was amplified by PCR with gene-specific primers: 309dir—5'-AGGGGAGCCTCACCACG-3' (SEQ ID NO:49) and 309rev—5'-CCACGGATCT-GAAGGGTGAA-3' (SEQ ID NO:50) and then is ligated with T7 promoter containing oligonucleotide. Following PCR reactions were performed to prepare two PCR fragments the first from 309dir and T7 primers and the second—from 309rev and T7 primers. These fragments were used for RNA synthesis from T7 promoter. One of the resulted synthetic RNA corresponds to sence and another—to antisence RNA of p53 gene. These RNAs were mixed with fluorescently labeled (TAMRA at 5' end and quencher DABCYL at 3' end) oligonucleotide (15 nt) that is complemented to sense RNA and incubated with crab DSN. Reaction was performed in 20 mkl containing 50 ng synthetic RNA; 25 mM Tris-HCl, pH7.8, 5 mM MgCl$_2$, 0.25 mM fluorescent oligonucleotide. Reaction was carry out for 3 h at 35° C. and then was stopped by EDTA. Fluorescence intensity change in the reaction containing sense RNA was significant higher than fluorescence intensity change in the reaction with antisense RNA (FIG. 16).

4. DSNP Assay for Analysis of Allele-Specific PCR Results.

Allele-specific amplification (ASA), also known as amplification of specific alleles (PASA) and amplification refractory mutation system (ARMS), is a generally applicable technique for the detection of known point mutations, small deletions and insertions, polymorphisms and other sequence variations. Several methods based on the ASA principle have been described in the art (Sommer, S. S., J. D. Cassady, J. L. Sobell, and C. D. K. Bottema. Mayo Clin. Proc. 1989, 64: 1361-1372; Newton C R, Graham A, Heptinstall L E, Powell S J, et al., Nucleic Acids Research, 1989, Vol 17, Issue 7, pages 2503-2516; Bottema C D, Sommer S S. Mutat Res 1993, 288(1):93-102; Hodgson D R, Foy C A, Partridge M, Pateromichelakis S, Gibson N J. Mol Med 2002, 8(5):227-237; Dutton C, Sommer S S. Biotechniques 1991, 11(6):700-2; Rust S, Funke H, Assmann G. Nucleic Acids Res 1993, 21(16):3623-3629; Ye S. Dhillon S, Ke X, Collins A R, Day I N. Nucleic Acids Res. 2001, 29(17):E88-8; Liu Q, Thorland E C, Heit J A, Sommer S S. Genome Res. 1997, 7(4):389-398; Myakishev M V, Khripin Y., Hu S, Hamer D. Genome Res. 2001, 11: 163-169). DSNP assay is applicable for monitoring of the formation of allele-specific PCR products during the ASA (FIG. 16). This method utilizes allele-specific PCR primers, each of that contains a universal 5'-tail short unique sequence (e.g. 10-15 nt) that becomes part of the PCR product on amplification.

PCR products may be obtained using any ASA modification. After amplification, PCR products are mixed with DSN and two probe oligonucleotides labeled with the fluorescence donor and quencher as described above. Each probe generates fluorescence at specific wavelengths after cleaving. The first probe coincides with the unique universal sequence of the one allele-specific primer and the second coincides with the unique sequence of the other allele-specific primer. The mixture is incubated with DSN, during which the nuclease cleaves the PCR product to generate short DNA fragments that can effectively hybridize with probe oligonucleotides. Probe oligonucleotides anneal to the 5'-tail universal sequences in the PCR products. All perfectly matched duplexes generated by the DNA template and probe oligonucleotides are cleaved by DSN to generate allele-specific fluorescence.

Cleavage reaction with DSN for analysis of ASA results may be performed using any protocol described above in the section 1 of the Examples. Probe oligonucleotides of the present example may vary but typically range from 9 to 25 nt (usually 10-15 nt).

The method was tested in a model experiment for the analysis of the 7028 C-T SNP in the COX1 gene. The allele specific primers (MtL-C 5'-gccctgtagtacacgtactacgttgttgcc-3' (SEQ ID NO:51) and MtL-T 5'-gctcgctgagacacgtactacgttgft-gct-3') were used for PCR with common primer Mit70Rev 5'-acagctcctattgataggac-3' (SEQ ID NO:52). PCR was performed using the Advantage 2 PCR Kit (Clontech) as described above. 25 PCR cycles were performed at 95° C. for 7 s, 62° C. for 20 s and 72° C. for 15 s. An 10 mkl of the PCR products containing about 75 ng DNA was mixed with 1.5 μk 10×DSNP buffer, universal probe oligonucleotides FL-gccct-gtagt-Dab (SEQ ID NO:53) (C-variant specific) and Tam-gctcgctgag-Dab (SEQ ID NO:54) (T-variant specific) to a final concentration of 0.25 μM, 1 Kunitz unit crab DSN, milliQ water (to a final volume of 15 μl) and incubated at 60° C. for 10 min and then at 35° C. for 10 min. Detection of fluorescence signals was performed under UV light. A clear result was obtained for both mutant and wild-type sequence comprising samples.

5. DSNP Assay on a Solid Phase.

Figure 17:
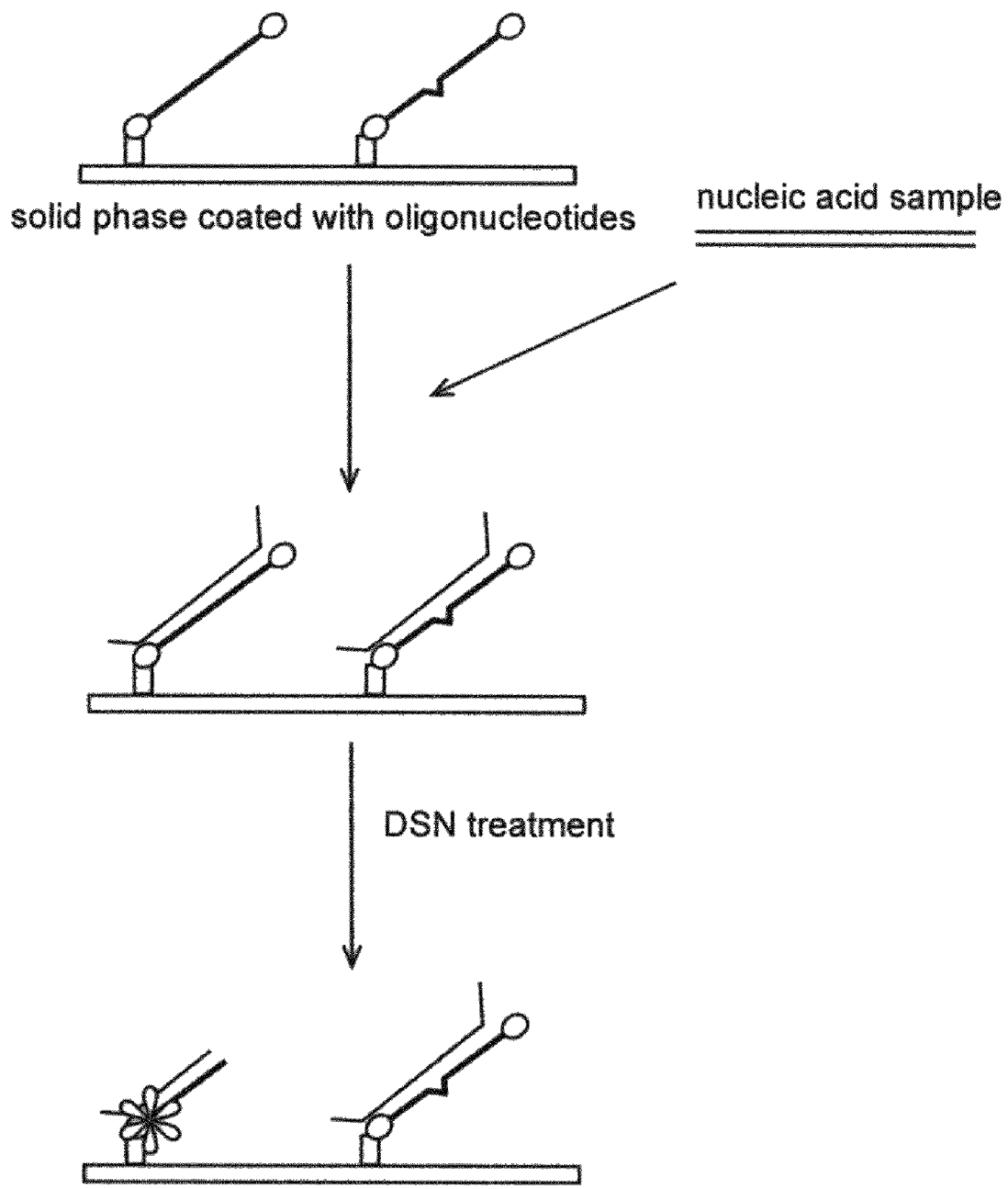
FIG. 17 provides a schematic diagram of DSNP assay performed on a solid phase. Shadow rectangles indicate the common part of oligonucleotides that cannot be cleaved by a nuclease according to the subject invention. Grey circles indicate the quenching agent, green circles—fluorescence donors. The green asterisks indicate the fluorescence label generated after oligonucleotide cutting by a nuclease according to the subject invention.

The DSNP assay is suitable for a microarray format without the need for considerable modification. In this case, for each sequence (or sequence variant) to be detected, a sequence-specific labeled probe oligonucleotide is designed. Probe oligonucleotides are immobilized on the solid phase (microarray) through a spacer followed by a 10-25 nt specific sequence, able to form perfectly matched duplexes with sequencers) of interest (e.g. in the case of SNP detection, for each SNP two probes are used, which differ in the positions corresponding to allelic distinction). Each probe is labeled with a fluorescent donor and a quencher at the ends of the specific sequence, so that a fluorescence signal is generated on a microarray after cleavage by DSN. All probe oligonucleotides may be labeled by one type of the label (e.g. one type of fluorescent donor), because the signals for different sequence variants would be different by their positions. A schematic diagram of the DSNP assay on a microarray is provided in FIG. 17.

6. DNA Sequencing

The DSNP assay is also useful for nucleic acid sequencing. To determine the sequence of the nucleic acid of interest, the nucleic acid is contacted under hybridizing conditions with a full set of every possible oligonucleotide of the same length (for instance, 10 nucleotides long) placed on solid phase. Following treatment with an appropriate DNase, as described in the section 1 of the Examples, above, cleaved oligonucleotides are detected as a means for determining which oligonucleotides hybridized to the nucleic acid to be sequence. The sequence of the test oligonucleotide is then compiled using known protocols of sequencing by hybridization, known to those of skill in the art and described in U.S. Pat. Nos. 5,525, 464; 5,700,637 and 5,800,992, the disclosures of which are herein incorporated by reference.

III. Production of Normalized and Subtracted Libraries and Probes for Differential Screening A. General Description and Advantages Provided The methods are based on selectively cleavage of DNA in DNA containing nucleic acid duplexes to retain the single stranded DNA of interest. As such, the subject methods can be used for the elimination of the fractions of redundant and/or common molecules of DNA during normalization and\or subtractive hybridization. The methods proposed are simple and are applicable for full-length subtraction/normalization as well as for subtraction/normalization on fragmented nucleic acids. These methods are applicable for cDNA subtraction/normalization as well for genome subtraction without any modifications. Also, during subtractive hybridization the enrichment in target molecules is accompanied by the equalization of target molecule concentration that prevents the rare transcript loss. Specific nucleases that may be used in the subject methods are duplex specific DNA nucleases. In certain embodiments, subject nucleases are heat stable nucleases like crab DSN.

B. Normalization

The following method based on the selective amplification of normalized DNA ss-fraction formed by the partial reassociation of the denatured ds-cDNA may be employed to obtain equalized cDNA libraries. The following method does not include the physical separation of the ss- and ds-fractions. ds-DNA fractions are degraded by DSN (double-stranded specific DNAse) whereas ss fractions are not degraded. After DSN treatment, the molecules of the ss-fractions are amplified by PCR.

Figure 18:
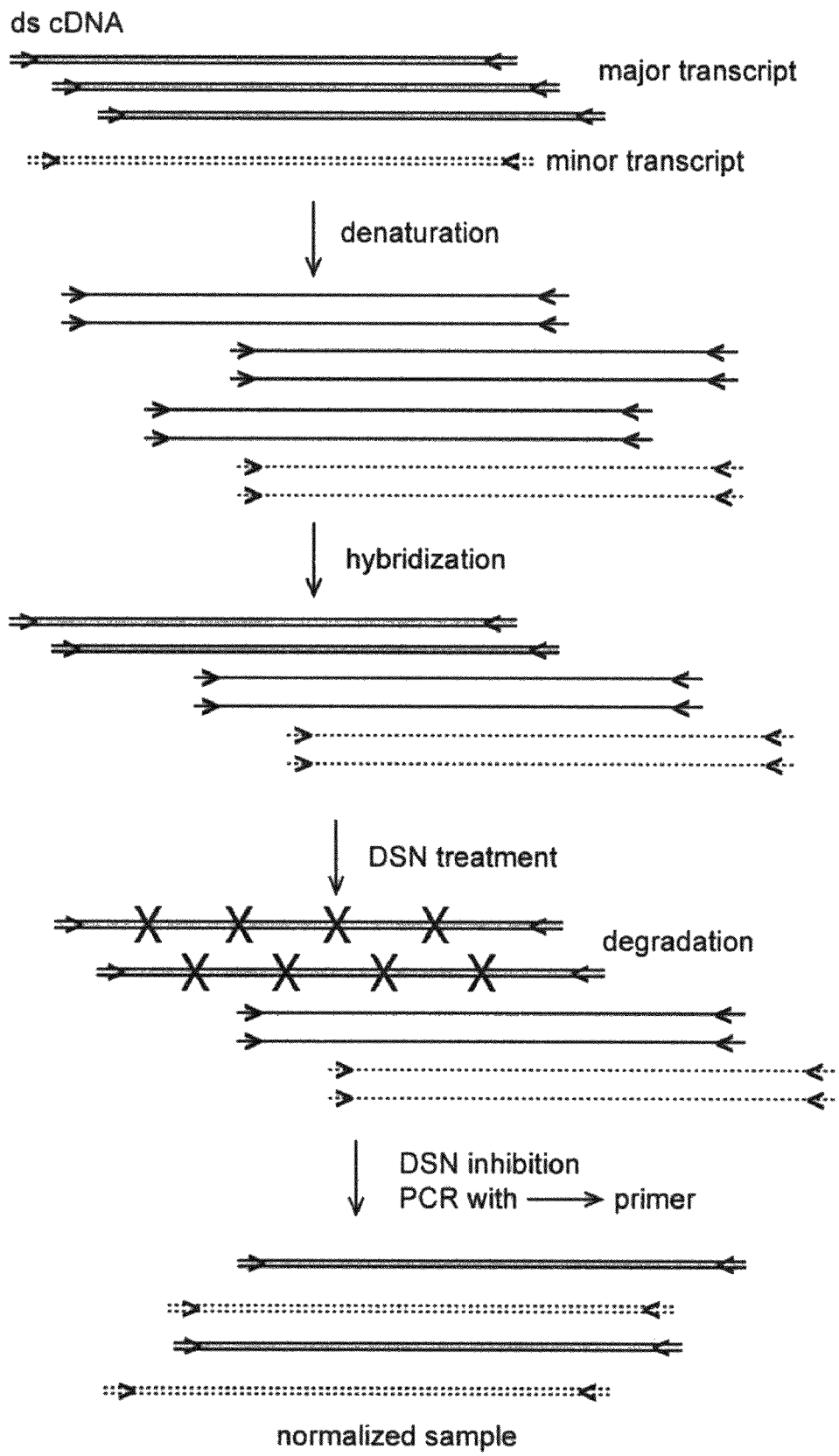
FIG. 18 provides a schematic diagram of a cDNA equalization procedure according to the subject invention. Arrows represent the adapter and complementary primer. Dashed lines indicate rare transcripts, black color—abundant transcripts. The scheme shown in FIG. 18 does not show the ds-cDNA synthesis that might be performed by different ways.

The equalized cDNA library was obtained as outlined in the scheme (FIG. 18). The scheme does not show the ds-cDNA synthesis that might be performed by different ways. The method is applicable for both full-length and fragment (or digested) DNA. The normalization of genomic DNA samples might also be performed. The DNA must contain the known terminal sequences (adaptors) that are ligated or are attached during cDNA synthesis to DNA. Before normalization, DNA samples is purified using methods known in the art, precipitated by ethanol and dissolved in hybridization buffer.

For the normalization, DNA is denatured and then is allowed to renature (hybridization step). Since the renaturation of an individual sequence is the reaction of the second order in respect to the sequence concentration, the renaturation of abundant sequences are higher than those of rare sequences, which results in the equalization of the ss-DNA fraction.

After hybridization, the DNA sample is incubated with specific nuclease to degrade ds-DNA fractions. Then inhibition of the nuclease activity (e.g. by heating) is then performed. After, residuary ss-DNA fraction may be amplified by PCR with adaptor-specific primers. As a result, selectively amplified equalized cDNA is obtained.

The example of the appropriate protocol using crab DSN is follow:

ds cDNA (as noted above any other DNA samples may also be used) is purified, precipitated by ethanol and dissolved in milliQ water to final concentration at least 25 ng/mkl. Of about 100-150 ng of purified DNA is mixed with hybridization buffer (50 mM HEPEC-HCl, pH8.3; 0.5 M NaCl), denatured (e.g. at 97° C. for 3 min) and allowed to renature (e.g. at 70° C. for 5-6 h). After, 1 mkl 10×DSN buffer, 0.5-1 Kunitz-units DSN and milliQ water to final volume 10 mkl are added to the renatured DNA sample. Resulted mixture is incubated at 65° C. for 20-30 min. After incubation, DSN is inactivated by heating at 97° C. for 7-10 min. Reaction is diluted by milliQ water to 40 mkl, 1 mkl of the diluted reaction is used for PCR to amplify normalized DNA.

Figure 19:
FIG. 19 shows the results of agarose electrophoresis following ethidium-bromide staining of non-normalized amplified cDNA (line 1) and normalized amplified cDNA (line 2). M-marker, 1 kb ladder (Gibco BRL).

This method was tested on cDNA sample prepared using Smart PCR cDNA Synthesis Kit (CLONTECH) and amplified in PCR using Advantage™ 2 PCR Kit with SMART II oligonucleotide primer. After 17 cycles of PCR, cDNA were purified from unincorporated triphosphates and the excess of primers using QJ Aquich PCR Purification Kit (Qiagen), precipitated by ethanol and diluted in water to final concentration 25 ng/mkl. 4 mkl DNA solution was mixed with 1 mkl 4× hybridization buffer and denatured at 98° C. for 3 min. Afterwards, cDNA was allowed for renature at 70° C. for 6 h and then mixed with 1 mkl 1×DSN buffer, 1 Kunitz-units crab DSN and milliQ water to final volume 10 mkl. Cleavage reaction was performed at 65° C. for 20 min. After incubation, DSN was inactivated by heating at 97° C. for 7 min. Reaction was diluted by milliQ water to 40 mkl, 1 mkl of the diluted reaction was used in PCR using Advantage™ 2 PCR Kit with SMART II oligonucleotide primer (FIG. 19). To analyze the efficiency of normalization, the sequencing of the 400 independent clones from normalized and non-normalized libraries was performed. A percent of the redundant clones in non-normalized library was 19%, whereas only 1% in normalized library.

C. Supernormalization

The method described in this section is a modification of the above normalization scheme. In this variant, DNA to be normalized (that may be first strand cDNA, amplified cDNA, etc.) is mixed with driver nucleic acids (RNA or cDNA), derived from the same tissues. If the driver nucleic acids are DNA, the DNA preparation is performed so as DNA does not comprise adapter sequences. During hybridization, additional hybrids, those are driver RNA-target DNA or driver DNA-target DNA hybrids, are generated that allow effective removal of abundant molecules from ss-fraction. As was shown, DSN effectively cleave DNA in both DNA-DNA and DNA-RNA duplexes. Thus, addition of driver nucleic acids leads to most efficient removal of abundant molecules (as compared to example I) from ss-DNA fraction.

Figure 20:
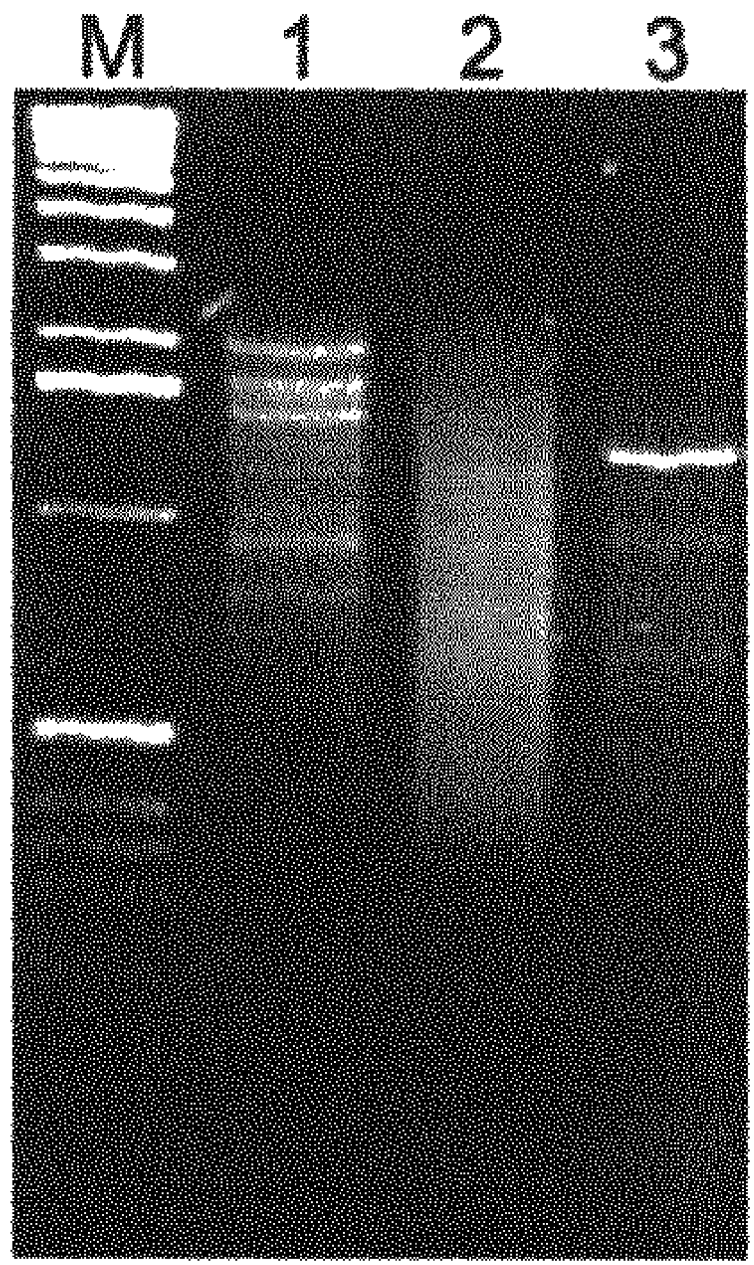
FIG. 20 provides the results of agarose electrophoresis following ethidium-bromide staining of non-normalized amplified liver cDNA (line 1), obtained by PCR with SMART II oligonucleotide primer, supernormalized liver cDNA (line 2), 28 cycles; and subtracted liver cDNA (line 3), 30 cycles. M-marker, 1 kb ladder (Gibco BRL).

As an example, normalized cDNA from human liver RNA was prepared: polyA RNA from human liver (CLONTECH) was used for full length first strand cDNA preparation by Smart PCR cDNA Synthesis Kit (CLONTECH). Reverse transcriptase was heat inactivated. First strand cDNA was purified and mixed with excess of liver polyA RNA, denatured and hybridized overnight at 69° C. in buffer for hybridization (CLONTECH). After hybridization, hybridizing DNA was diluted in DSN buffer and incubated with DSN at 65° C. for 30 min. The cleavage reaction was stopped by heating. Then mixture was diluted to 40 mkl and 1 mkl was used in PCR with SMART II oligonucleotide primer. 28 cycles of PCR were performed (FIG. 20, line 2).

D. Subtractive Hybridization

Figure 21:
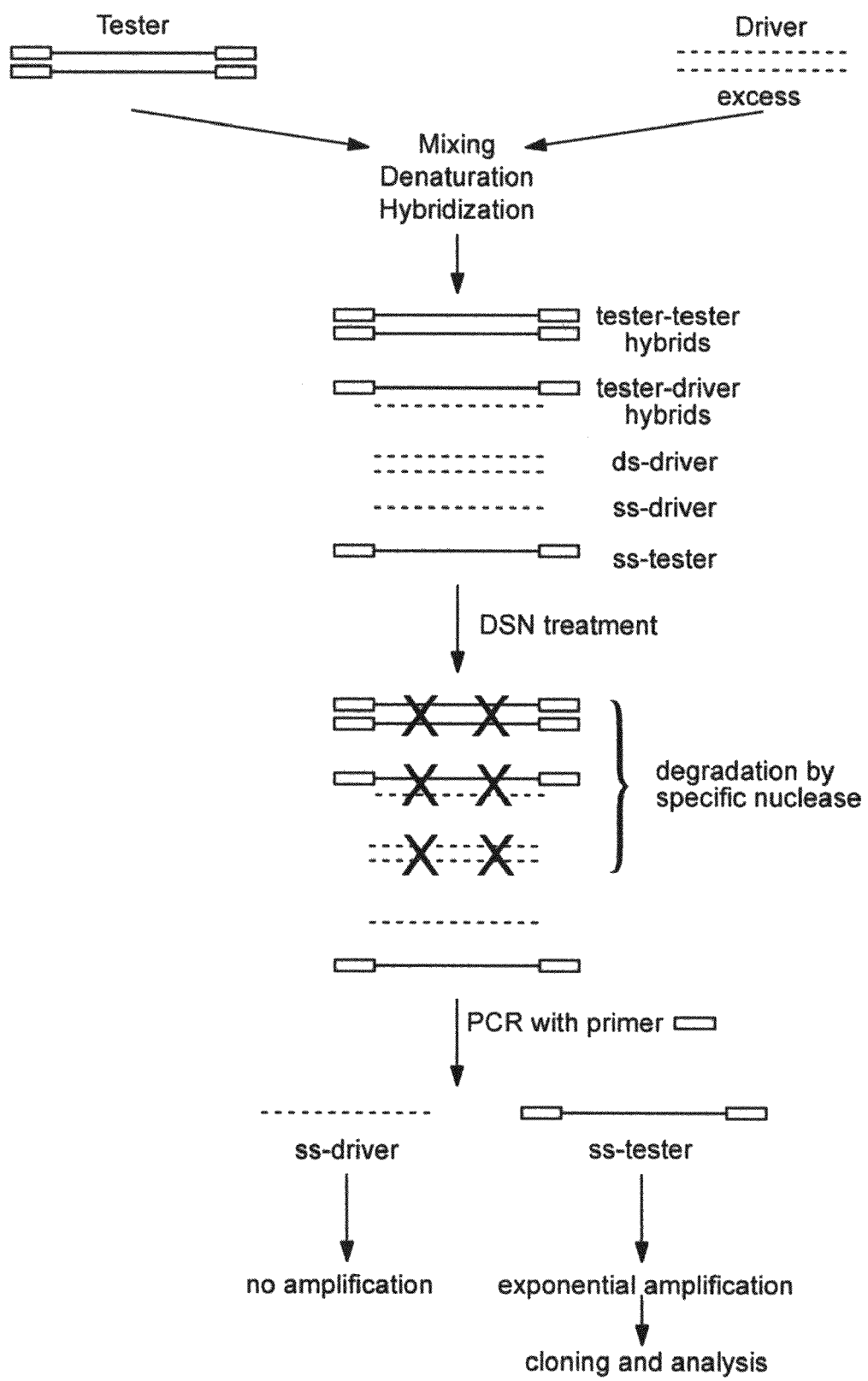
FIG. 21 provides a schematic diagram of an equalizing cDNA subtraction procedure according to the subject invention. Open boxes represent the adapter and complementary primer.

A similar scheme was performed for subtractive hybridization (FIG. 21), only that driver nucleic acids is derived from other than tester DNA source. The tester is genomic DNA or cDNA flanked by adapters. Driver is DNA (genome or cDNA) with no adapters or RNA (preferably mRNA).

1. At the first stage of the procedure the excess driver is added to tester, the samples are melted and left to anneal. In the course of hybridization, tester molecules that have their pair in driver for the most part form hybrids driver-tester and thus become removed from the ss-fraction. Meanwhile, target molecules are not affected by the "driver pressing" and therefore ss-tester becomes enriched with the molecules of this kind. Target molecules are also able to form homohybrids with each other (reassociate). Reassociation progresses much more rapidly for high abundant target molecules than for low abundant ones. As a result, the concentrations of target molecules in ss-tester become equalized. Driver abundant molecules also form driver-driver hybrids and ss-driver molecules also remain.

After hybridization the sample is treated by DSN. DSN cleaves DNA in DNA-DNA and DNA-RNA hybrids. Thus, only ss-fractions remain. It was shown that DSN has low activity to RNA both in ss-fraction and in RNA-RNA or RNA-DNA hybrids. Thus, in the scheme where driver is RNA, driver molecules are released from RNA-DNA hybrids after DNA degradation. Moreover, DSN is thermostable and DSN treating is performed at the temperature where hybridization is effective. Thus, an additional "driver pressing" to tester occurs during DSN treating that leads to most effective subtraction. After DSN treatment, target molecules (ss-tester fraction) might be amplified by PCR with adaptor-specific primers. Driver molecules (if driver is DNA) are not amplified because they do not have these adapters.

2. In the course of hybridization, driver-tester hybrids are generated most effectively by more abundant molecules. To increase the power of subtraction additional freshly denatured driver is added during hybridization. Excess of driver for redundant molecules then appears much higher than at the beginning, because the majority of them have been already removed from ss-fraction of tester. In particular, the excess appears extremely high for molecules of high-abundance class. This leads to the inversion of the original disproportion in concentrations of redundant molecules: originally high- and medium-abundant transcripts become almost entirely removed from ss-tester.

As an example, the subtractive hybridization "liver-lung" was performed: full length first strand cDNA was prepared by Smart PCR cDNA Synthesis Kit (CLONTECH) from human liver polyA RNA (CLONTECH). This first strand cDNA (tester) was mixed with 50× excess of lung polyA RNA, denatured at 99° C. for 2 min and hybridized overnight at 69° C. in buffer for hybridization (CLONTECH). Hybridizing DNA was diluted in DSN buffer and incubated with DSN at 65° C. for 1 h. To stop the reaction, EDTA was added. Then mixture was diluted by ten folds and 1 µl was used in PCR with SMART II oligonucleotide primer. 30 cycles of PCR were performed (FIG. 20, line 3).

It is evident that the above results and discussion that the subject invention provides an important new nuclease with novel activities that finds use in a variety of different applications. Therefore, the present invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated nucleic acid encoding a nuclease having at least 95% amino acid sequence identity to the amino acid sequence of a nuclease encoded by the nucleic acid comprising SEQ ID NO:02.

2. The isolated nucleic acid of claim 1, said nucleic acid comprising the nucleotide sequence of SEQ ID NO:02.

3. An expression cassette comprising:
a transcriptional initiation region functional in an expression host;
a nucleic acid having a nucleotide sequence found in a nucleic acid according to claim 1 under the transcriptional regulation of said transcriptional initiation region; and
a transcriptional termination region functional in said expression host.

4. A cell comprising an expression cassette according to claim 3 as part of an extrachromosomal element or integrated into its genome as a result of introduction of said expression cassette into said cell.

5. A method of producing a nuclease, said method comprising:
growing a cell according to claim 4 to express said nuclease; and
isolating said nuclease substantially free of other proteins.

* * * * *

UNITED STATES PATENT AND TRADEMARK OFFICE
CERTIFICATE OF CORRECTION

PATENT NO. : 7,803,922 B2  Page 1 of 1
APPLICATION NO. : 12/012156
DATED : September 28, 2010
INVENTOR(S) : Lukyanov et al.

It is certified that error appears in the above-identified patent and that said Letters Patent is hereby corrected as shown below:

Col. 45 line 27, replace the following sequence of letters: 5gttacftcaaggacaaaatacc-3'" with "5'gttacttcaaggacaaaatacc-3'"

Signed and Sealed this
Thirty-first Day of July, 2012

David J. Kappos
*Director of the United States Patent and Trademark Office*

SEQUENCE LISTING

<160> NUMBER OF SEQ ID NOS: 66

<210> SEQ ID NO 1
<211> LENGTH: 407
<212> TYPE: PRT
<213> ORGANISM: Kamchatka crab

<400> SEQUENCE: 1

```
Met Ala Asn Met Glu Ser Lys Gln Gly Ile Met Val Leu Gly Phe Leu
 1               5                   10                  15

Ile Val Leu Leu Phe Val Ser Val Asn Gly Gln Asp Cys Val Trp Asp
            20                  25                  30

Lys Asp Thr Asp Phe Pro Glu Asp Pro Pro Leu Ile Phe Asp Ser Asn
        35                  40                  45

Leu Glu Leu Ile Arg Pro Val Leu Glu Asn Gly Lys Arg Ile Val Ser
    50                  55                  60

Val Pro Ser Gly Ser Ser Leu Thr Leu Ala Cys Ser Gly Ser Glu Leu
65                  70                  75                  80

Ile Asn Leu Gly Met Glu Ala Val Glu Ala Lys Cys Ala Gly Gly Val
                85                  90                  95

Met Leu Ala Ile Glu Gly Thr Glu Trp Glu Ile Trp Ser Leu Gly Cys
            100                 105                 110

Ser Asn His Val Lys Glu Thr Ile Arg Arg Asn Leu Gly Thr Cys Gly
        115                 120                 125

Glu Ala Asp Gln Gly Asp Arg His Ser Ile Gly Phe Glu Tyr Tyr Gly
    130                 135                 140

Gly Ser Ile Tyr Tyr Glu Leu Ile Ser Val Cys Phe Gly Pro Val Ser
145                 150                 155                 160

Glu Thr Thr Leu Arg Thr Glu His Val Leu His Gly Ala Asn Ile Ala
                165                 170                 175

Ala Lys Asp Ile Glu Thr Ser Arg Pro Ser Phe Lys Thr Ser Thr Gly
            180                 185                 190

Phe Phe Ser Val Ser Met Ser Thr Val Tyr Ser Gln Ala Ser Gln Leu
        195                 200                 205
```

```
Gln Leu Met Thr Asp Ile Leu Gly Asp Ser Asp Leu Ala Asn Asn Ile
        210                 215                 220
Ile Asp Pro Ser Gln Gln Leu Tyr Phe Ala Lys Gly His Met Ser Pro
225                 230                 235                 240
Asp Ala Asp Phe Val Thr Val Ala Glu Gln Asp Ala Thr Tyr Tyr Phe
                245                 250                 255
Ile Asn Ala Leu Pro Gln Trp Gln Ala Phe Asn Gly Asn Trp Lys
            260                 265                 270
Tyr Leu Glu Tyr Ala Thr Arg Asp Leu Ala Glu Ser His Gly Ser Asp
        275                 280                 285
Leu Arg Val Tyr Ser Gly Gly Trp Ser Leu Leu Gln Leu Asp Asp Ile
        290                 295                 300
Asn Gly Asn Pro Val Asp Ile Leu Leu Gly Leu Ser Glu Gly Lys Glu
305                 310                 315                 320
Val Val Pro Val Pro Ser Leu Thr Trp Lys Val Val Tyr Glu Glu Ser
                325                 330                 335
Ser Ser Lys Ala Ala Ala Ile Val Gly Ile Asn Asn Pro His Ile Thr
            340                 345                 350
Thr Ala Pro Ser Pro Leu Cys Ser Asp Leu Cys Ser Ser Leu Thr Trp
        355                 360                 365
Ile Asp Phe Asn Leu Asp Asp Leu Ala His Gly Tyr Thr Tyr Cys Cys
        370                 375                 380
Ala Val Asp Asp Leu Arg Gln Ala Ile Pro Tyr Ile Pro Asp Leu Gly
385                 390                 395                 400
Asn Val Gly Leu Leu Thr Asn
                405

<210> SEQ ID NO 2
<211> LENGTH: 1419
<212> TYPE: DNA
<213> ORGANISM: Paralithodes camtschaticus

<400> SEQUENCE: 2
aagcagtggt atcaacgcag agtacgcggg ggagatagga ctgagtgagt gagtgtgaga      60
gggaaagaag gaatggccaa catggagtcc aagcaaggaa taatggtttt gggattctta     120
attgtcctcc tcttcgtgtc tgtcaatggc caggactgtg tgtgggacaa ggacacggac     180
tttcccgagg acccgccact cattttcgat tcaaacttgg agctcatcag acccgtcttg     240
gaaaatggca aaaggatcgt cagtgtcccc agtggcagca gcttaacctt ggcctgctct     300
gggtctgaac tgatcaacct gggcatggag gcggtggaag ccaagtgtgc tgggggagtc     360
atgcttgcca tagaaggaac ggagtgggag atctggagcc tggggtgcag caaccacgtg     420
aaggagacca tccgccgcaa ccttggaaca tgtggggaag cggaccaggg ggataggcac     480
agtattggct tcgagtacta cggtggctcc atctattatg aactgatcag cgtgtgtttc     540
gggcccgtgt ccgaaacaac cttgcgcacc gagcatgtcc tccacggcgc aacattgcc      600 gccaaggaca tcgagacctc ccgcccctcc ttcaagacct ccaccgggtt cttcagcgtc     660
tccatgtcca ccgtctacag ccaggcgtca cagctgcagt taatgacaga catattggga     720
gattcggatc tagccaacaa catcatcgac ccctcccaac agttgtactt cgccaaaggt     780
cacatgtctc ctgacgcaga ctttgtgacg gtggcagaac aggacgccac ctactacttc     840
atcaacgccc taccgcagtg gcaggccttc aataatggca actggaagta cctagaatac     900
gcgacccgag acctggccga atcccacggt agcgacctgc gagtgtatag cggagggtgg     960
```

```
agcctgctgc agctagatga tattaacggc aaccccgtgg acatcctgct gggactgtct    1020
gagggcaagg aggtcgtgcc cgttccatcc ctcacttgga aggtggttta cgaagagagc    1080
agcagcaaag cggccgcgat cgtcggtatc aacaaccctc acatcaccac cgcccctcc     1140 cccttgtgtt ccgacctgtg ctcctccttg acctggatag acttcaacct ggacgacctg    1200
gctcacgggt acacctactg ttgtgccgta gatgacctcc ggcaggccat accctatatc    1260
ccggacctgg gcaatgtcgg actcctcact aactaattct atctatctat catatatgct    1320
caggcccaat ccccattttg ggggtagccg aactcaagaa cagagccaag aaacagggaa    1380
aaaaaaaaaa aaaaaaaaaa aaaaaaaaaa aaaaaaaa                            1419

<210> SEQ ID NO 3
<211> LENGTH: 24
<212> TYPE: DNA
<213> ORGANISM: Paralithodes camtschaticus

<400> SEQUENCE: 3
tacattaatg ccgtccctca gtgg                                             24

<210> SEQ ID NO 4
<211> LENGTH: 24
<212> TYPE: DNA
<213> ORGANISM: Paralithodes camtschaticus

<400> SEQUENCE: 4
caggccttta ataatggtaa ttgg                                             24

<210> SEQ ID NO 5
<211> LENGTH: 23
<212> TYPE: DNA
<213> ORGANISM: Paralithodes camtschaticus

<400> SEQUENCE: 5
aggcctttaa taatggtaac tgg                                              23

<210> SEQ ID NO 6
<211> LENGTH: 21
<212> TYPE: DNA
<213> ORGANISM: Paralithodes camtschaticus

<400> SEQUENCE: 6
cctcagtggc aggctttcaa t                                                21

<210> SEQ ID NO 7
<211> LENGTH: 21
<212> TYPE: DNA
<213> ORGANISM: Paralithodes camtschaticus

<400> SEQUENCE: 7
cctcagtggc aggctttcaa c                                                21

<210> SEQ ID NO 8
<211> LENGTH: 19
<212> TYPE: DNA
<213> ORGANISM: Paralithodes camtschaticus

<400> SEQUENCE: 8
gggtcgcgta ttctaggta                                                   19

<210> SEQ ID NO 9
```

```
<211> LENGTH: 20
<212> TYPE: DNA
<213> ORGANISM: Paralithodes camtschaticus

<400> SEQUENCE: 9
ccattattga aggcctgcca                                                      20

<210> SEQ ID NO 10
<211> LENGTH: 20
<212> TYPE: DNA
<213> ORGANISM: Uca crassipes

<400> SEQUENCE: 10
ggattgccat taatgtcgtc                                                      20

<210> SEQ ID NO 11
<211> LENGTH: 20
<212> TYPE: DNA
<213> ORGANISM: Uca crassipes

<400> SEQUENCE: 11
ccactgtaca cccgaaggtc                                                      20

<210> SEQ ID NO 12
<211> LENGTH: 20
<212> TYPE: DNA
<213> ORGANISM: Uca crassipes

<400> SEQUENCE: 12
aaccaaggct cgccaagtcc                                                      20

<210> SEQ ID NO 13
<211> LENGTH: 22
<212> TYPE: DNA
<213> ORGANISM: grammarus

<400> SEQUENCE: 13
caatggtccg aattctgttc tc                                                   22

<210> SEQ ID NO 14
<211> LENGTH: 20
<212> TYPE: DNA
<213> ORGANISM: grammarus

<400> SEQUENCE: 14
gtgactacgc gcagagtggc                                                      20

<210> SEQ ID NO 15
<211> LENGTH: 19
<212> TYPE: DNA
<213> ORGANISM: Palaemonidae sp

<400> SEQUENCE: 15
ccagcactcc ccaacctcc                                                       19

<210> SEQ ID NO 16
<211> LENGTH: 20
<212> TYPE: DNA
<213> ORGANISM: Palaemonidae sp

<400> SEQUENCE: 16
gtcaggtcag tgccgtgggc                                                      20
```

<210> SEQ ID NO 17
<211> LENGTH: 1424
<212> TYPE: DNA
<213> ORGANISM: grammarus

<400> SEQUENCE: 17

```
tgtagcgtga agacgacaga agtaatacga ctcactatag ggcaagcagt ggtaccaacg      60
cagagtactc gtcttccttt tttttttttgg tgttgctgcc ccactgtgca aacttgaggc     120
gctgctcttg gcaactgaga aattctacga atcagacgat acacgcttca tagttcagac     180
cacttttgt tgtacaacta ttttttttta ttattatttt agttgtattt tattatttga      240
agagaagaaa gtttgtgcta caatttcaac actgcttcac aatattgtct tatacaggca     300
attgggaaat acatcactag agcgagactc cgaatatctg tcacttcaaa agccggtcga     360
gaacttcgaa tgcgagagct ccatccagta caatgttttg cccttgggag gaggaaacga     420
agaggacgag gaggatagta ttggaggggt gagcgctttt ggctatgacc tcaaggaaac     480
tttctacacc atctacaagt tgagtttga taagacgaag atgatgagca gccgagtgga      540
ccacatcctc cacggcaggg agttattgaa ggccgagcct cacagggatt acaagttcag     600
aagtgatgca gtcctcccctt ggggaagcct caccaagatc aagaaatgct actcgaatca     660
gaatcaagat gcggtgctgc agcacttcca agatcaggga agtaatgaga aagaaaata      720
ctttgcgcga ggtcacctgg cagcaaatgc agacttcgtg tcacaagacg agcagaaagc     780
ttcctacagc ttcgccaacg tagcgcctca gtggcaggct ttcaacaatg gcaactggaa     840
gaaacttgag aacagaattc ggaccattgc catgaaaaag gaagccactc tgcgcgtagt     900
cactggcacc tccacgggtc ttctgaagct caatagtagt tctggacaac tggagaacgt     960
gtgcctgtgt gacggtgagc cgccgtgtgt tcctctcttc ttttggaagg tgacgcccgc    1020
gttaagacaa gcgttcctga tgcctaatca tcctgccgcg ggaatatcag ccagaattga    1080
agaactggca catccttgtc cgaattgggc aggtttctct ggagccgaag agaagactcg    1140
aggagccctg tattgcctca ccccaggcga cctctgtgga gttgagccga aggcttgtgg    1200
atacaaagat ttaatgtgaa ctctatattt gcatttgaat aaccttcgta cgtcatttgg    1260
tcaaattttg ctctgtgttt gtatatacaa aatgtccagg aatggccaaa agtgcagagg    1320
ttggtaaatt cttagagttc aacctcgaag ttgatactaa tagttttgaa aattgaaata    1380
tatgtttaac gcagttaaaa aaaaaaaaaa aaaaaaaaa aaaa                      1424
```

<210> SEQ ID NO 18
<211> LENGTH: 392
<212> TYPE: PRT
<213> ORGANISM: grammarus

<400> SEQUENCE: 18

```
Gly Lys Gln Trp Tyr Gln Arg Arg Val Leu Val Phe Leu Phe Phe
 1               5                  10                  15

Gly Val Ala Ala Pro Leu Cys Lys Leu Glu Ala Leu Leu Leu Ala Thr
                20                  25                  30

Glu Lys Phe Tyr Glu Ser Asp Asp Thr Arg Phe Ile Val Gln Thr Thr
            35                  40                  45

Phe Cys Cys Thr Thr Ile Phe Phe Tyr Tyr Phe Ser Cys Ile Leu
        50                  55                  60

Leu Phe Glu Glu Lys Lys Val Cys Ala Thr Ile Ser Thr Leu Leu His
65                  70                  75                  80

Asn Ile Val Leu Tyr Arg Gln Leu Gly Asn Thr Ser Leu Glu Arg Asp
```

```
            85                  90                  95
Ser Glu Tyr Leu Ser Leu Gln Lys Pro Val Glu Asn Phe Glu Cys Glu
            100                 105                 110

Ser Ser Ile Gln Tyr Asn Val Leu Pro Leu Gly Gly Gly Asn Glu Glu
            115                 120                 125

Asp Glu Glu Asp Ser Ile Gly Gly Val Ser Ala Phe Gly Tyr Asp Leu
            130                 135                 140

Lys Glu Thr Phe Tyr Thr Ile Tyr Lys Phe Glu Phe Asp Lys Thr Lys
145                 150                 155                 160

Met Met Ser Ser Arg Val Asp His Ile Leu His Gly Arg Glu Leu Leu
                165                 170                 175

Lys Ala Glu Pro His Arg Asp Tyr Lys Phe Arg Ser Asp Ala Val Leu
                180                 185                 190

Pro Trp Gly Ser Leu Thr Lys Ile Lys Lys Cys Tyr Ser Asn Gln Asn
                195                 200                 205

Gln Asp Ala Val Leu Gln His Phe Gln Asp Gln Gly Ser Asn Glu Lys
            210                 215                 220

Arg Lys Tyr Phe Ala Arg Gly His Leu Ala Ala Asn Ala Asp Phe Val
225                 230                 235                 240

Ser Gln Asp Glu Gln Lys Ala Ser Tyr Ser Phe Ala Asn Val Ala Pro
                245                 250                 255

Gln Trp Gln Ala Phe Asn Asn Gly Asn Trp Lys Lys Leu Glu Asn Arg
                260                 265                 270

Ile Arg Thr Ile Ala Met Lys Lys Glu Ala Thr Leu Arg Val Val Thr
                275                 280                 285

Gly Thr Ser Thr Gly Leu Leu Lys Leu Asn Ser Ser Ser Gly Gln Leu
            290                 295                 300

Glu Asn Val Cys Leu Cys Asp Gly Glu Pro Pro Cys Val Pro Leu Phe
305                 310                 315                 320

Phe Trp Lys Val Thr Pro Ala Leu Arg Gln Ala Phe Leu Met Pro Asn
                325                 330                 335

His Pro Ala Ala Gly Ile Ser Arg Ile Glu Glu Leu Ala His Pro
                340                 345                 350

Cys Pro Asn Trp Ala Gly Phe Ser Gly Ala Glu Glu Lys Thr Arg Gly
                355                 360                 365

Ala Leu Tyr Cys Leu Thr Pro Gly Asp Leu Cys Gly Val Glu Pro Lys
            370                 375                 380

Ala Cys Gly Tyr Lys Asp Leu Met
385                 390

<210> SEQ ID NO 19
<211> LENGTH: 1414
<212> TYPE: DNA
<213> ORGANISM: Palaemonidae sp

<400> SEQUENCE: 19
tgtagcgtga agacgacaga agtaatacga ctcactatag ggcaagcagt ggtatcaacg    60
cagagtacgc gggctccttg ttcagagctt taaagtcatg gctggcagga gacaattctt   120
cgtcttatct ttatatttcg tggccttttg gaacctttcc aaaggtcaag attgcgcctg   180
ggataaggat gcagacttcc cacttactcc tccccttctc ttggattctt ccctcaagat   240
gatatatcca gtgttagagg gatccctcag gatggtacga gtagcagctg gcagcactat   300
caccgtcgca tgttcaggga cgacaattag ctgctctagg tctcgaggct gttgagggga   360
```

```
acctgtgctg gcggcccaac tgatcactgg tgatggcact gataatgccc taaatgagtt    420
gggatgtgtg acgccgcatc tgagagcttg cagaagaacc tgggtgcctg tgagatgcag    480
atcttggtac ctccacgcag taggatttaa tattgccact acaggttcat tccatgaatt    540
cgaaagtata tgtttcgatc acgctgcaga gactactcta tacacaaagc atactctcca    600
tggagccaac atcatagcca agacgtgga tcctagcaga ccaccctca agcccgatac      660
tggattcttc acggtcgaag tcaataccgt ttatactcag gcttcacagc tggccttgat    720
ggaacagctg cttggtgatt ctgcactggc caaccagatc attaatccag atcaagagct    780
gttcatgtct agaggtcacc tctctccaga tgctgaccat gtactgatag ctgaacaaga    840
cgcaacttat tacttcatta cgttatgcc tcagtggcag gcatttaata atggaaactg     900
gaagtacttg gaatttgctg cagagatct tgctgtagcc cacggcactg acctgaccgt     960
ctacgatgga ggttggggag tgctggaact ggatgacatt aatggaaatc agtacagat   1020
ttacctggga ctcagtgaag gcaaagaagt tgttccagcg cctgctctca tgtataagat  1080
tctgcacgaa gaaagcacta accgagctgc agctgttata ggcatcaaca ccccccacat  1140
tacagtggct ccaactccta tttgcactga tatctgctcc agtcttacat ggattgactt  1200
cgacattact gacctcttcc gtggttttac atactgctgc accgttgatg atctcagagc  1260
agccattcct cacgttcctg atcttggaaa tgttggtctt ttggacagtt aaacatccgt  1320
gacactctgt gaaagaggat cagttgtcgt gggaattgtt ataaatgaat aaataatgac  1380
tacagtaaaa aagaaaaaa aaaaaaaaaa aaaa                                1414
```

<210> SEQ ID NO 20
<211> LENGTH: 404
<212> TYPE: PRT
<213> ORGANISM: Palaemonidae sp

<400> SEQUENCE: 20

```
Met Ala Gly Arg Arg Gln Phe Phe Val Leu Ser Leu Tyr Phe Val Ala
  1               5                  10                  15

Phe Trp Asn Leu Ser Lys Gly Gln Asp Cys Ala Trp Asp Lys Asp Ala
             20                  25                  30

Asp Phe Pro Leu Thr Pro Pro Leu Leu Leu Asp Ser Ser Leu Lys Met
         35                  40                  45

Ile Tyr Pro Val Leu Glu Gly Ser Leu Arg Met Val Arg Val Ala Ala
     50                  55                  60

Gly Ser Thr Ile Thr Val Ala Cys Ser Gly Thr Thr Ile Ser Cys Ser
 65                  70                  75                  80

Arg Ser Arg Gly Cys Trp Arg Glu Pro Val Leu Ala Ala Gln Leu Ile
                 85                  90                  95

Thr Gly Asp Gly Thr Asp Asn Ala Leu Asn Glu Leu Gly Cys Val Thr
            100                 105                 110

Pro His Leu Arg Ala Cys Arg Arg Thr Trp Val Pro Val Arg Cys Arg
        115                 120                 125

Ser Trp Tyr Leu His Ala Val Gly Phe Asn Ile Ala Thr Thr Gly Ser
    130                 135                 140

Phe His Glu Phe Glu Ser Ile Cys Phe Asp His Ala Ala Glu Thr Thr
145                 150                 155                 160

Leu Tyr Thr Lys His Thr Leu His Gly Ala Asn Ile Ile Ala Lys Asp
                165                 170                 175

Val Asp Pro Ser Arg Pro Pro Phe Lys Pro Asp Thr Gly Phe Phe Thr
            180                 185                 190
```

Val Glu Val Asn Thr Val Tyr Thr Gln Ala Ser Gln Leu Ala Leu Met
            195                 200                 205

Glu Gln Leu Leu Gly Asp Ser Ala Leu Ala Asn Gln Ile Ile Asn Pro
        210                 215                 220

Asp Gln Glu Leu Phe Met Ser Arg Gly His Leu Ser Pro Asp Ala Asp
225                 230                 235                 240

His Val Leu Ile Ala Glu Gln Asp Ala Thr Tyr Tyr Phe Ile Asn Val
                245                 250                 255

Met Pro Gln Trp Gln Ala Phe Asn Asn Gly Asn Trp Lys Tyr Leu Glu
            260                 265                 270

Phe Ala Gly Arg Asp Leu Ala Val Ala His Gly Thr Asp Leu Thr Val
        275                 280                 285

Tyr Asp Gly Gly Trp Gly Val Leu Glu Leu Asp Asp Ile Asn Gly Asn
    290                 295                 300

Pro Val Gln Ile Tyr Leu Gly Leu Ser Glu Gly Lys Glu Val Val Pro
305                 310                 315                 320

Ala Pro Ala Leu Met Tyr Lys Ile Leu His Glu Glu Ser Thr Asn Arg
                325                 330                 335

Ala Ala Ala Val Ile Gly Ile Asn Asn Pro His Ile Thr Val Ala Pro
            340                 345                 350

Thr Pro Ile Cys Thr Asp Ile Cys Ser Ser Leu Thr Trp Ile Asp Phe
        355                 360                 365

Asp Ile Thr Asp Leu Phe Arg Gly Phe Thr Tyr Cys Cys Thr Val Asp
    370                 375                 380

Asp Leu Arg Ala Ala Ile Pro His Val Pro Asp Leu Gly Asn Val Gly
385                 390                 395                 400

Leu Leu Asp Ser

<210> SEQ ID NO 21
<211> LENGTH: 1377
<212> TYPE: DNA
<213> ORGANISM: Uca crassipes

<400> SEQUENCE: 21
aagcagtggt atcaacgcag agtacgcggg ggggagaagc actgcgctga gagaagcaga      60
gaggaaatgg atctccgacg aagattctcc cggaccttac aactggtagt ccttctcttc     120
gcctgtgcaa gcaattgctt tggatgcgag tgggacaaag acttggactt ccctgaacac     180
ccgccgctca tcattaacaa ccagctagat ttcgtgctgc cggtgttgga gggagtcaac     240
agggtggtga gggtggcaga gggagaaacc gtgactctgg cgtgctctgg tagcgagttg     300
gtaaatcttg gggaagcaga ggtgcaggct cggtgcctca gcagtggcct cctaacgatc     360
ggtgatgcag agtgggactt ggcgagcctt ggttgcagca gtgatgtaaa agagaccatt     420
ttccgcgacc tggggacctg cggcgccggt ggtgtcggga tcctaaatgg cattggcttc     480
cagattttca gtctcaacta cgacaaagtg atcattaacg tttgcttcga agcagcttcc     540
gagacgaccc tcttcactga tcacatcctc acggcgccg acatcgccgc taaggacgta     600
gaggcgtcca ggccgtcctt taagacttcc acagggttct tcagtgtctc tatgaacacc     660
gtgtattcgc agaactcgca actccaactc atgactagta ttctcggaga cgaggacccc     720
gccaatacaa ttattgaccc ttccaaacaa ctatacttcg caagggtca catgtctcct     780 gacgccggtt tcgtgactat agcaagccag gatgccacct attacttcat caatgccttg     840
ccacagtggc aggccttcaa caatggcaac tggaagtatc tggagactaa cacgcgaaat     900

-continued

```
ctggcaatga agaagggacg cgaccttcgg gtgtacagtg gtgggtggga tgtcctggag      960
ctggacgaca ttaatggcaa tcccgtgaag gtcttcctgg gactgacaga aggcaaggag     1020
gtagtgcccg cgcctgccat cacctggaag gtggtacacg atgagtccac taactgcgcc     1080
gtggccgtag tgggcgtcaa caacccgcat ctcaccgccg cccccgccac gctttgtgaa     1140
gacctgtgtt cctcgctctc ctggatcacc ttcgacgtta gcagtctcgc aagcgggtac     1200
acctaccgct gttccgtggc ggaactgcgc gcctcggtgc cccacgttcc tgacttaggc     1260
aatgtctgtc ttctcaccga ctaaagacga aacacatgtt ggagtcaccc agtaaatgga     1320
cagtggtgac atcaggttga cctaatcata atagtgtcat catgctaaaa aaaaaaa       1377
```

<210> SEQ ID NO 22
<211> LENGTH: 405
<212> TYPE: PRT
<213> ORGANISM: Uca crassipes

<400> SEQUENCE: 22

```
Met Asp Leu Arg Arg Arg Phe Ser Arg Thr Leu Gln Leu Val Val Leu
 1               5                  10                  15

Leu Phe Ala Cys Ala Ser Asn Cys Phe Gly Cys Glu Trp Asp Lys Asp
            20                  25                  30

Leu Asp Phe Pro Glu His Pro Pro Leu Ile Ile Asn Asn Gln Leu Asp
        35                  40                  45

Phe Val Leu Pro Val Leu Glu Gly Val Asn Arg Val Val Arg Val Ala
    50                  55                  60

Glu Gly Glu Thr Val Thr Leu Ala Cys Ser Gly Ser Glu Leu Val Asn
65                  70                  75                  80

Leu Gly Glu Ala Glu Val Gln Ala Arg Cys Leu Ser Ser Gly Leu Leu
                85                  90                  95

Thr Ile Gly Asp Ala Glu Trp Asp Leu Ala Ser Leu Gly Cys Ser Ser
            100                 105                 110

Asp Val Lys Glu Thr Ile Phe Arg Asp Leu Gly Thr Cys Gly Ala Gly
        115                 120                 125

Gly Val Gly Ile Leu Asn Gly Ile Gly Phe Gln Ile Phe Ser Leu Asn
    130                 135                 140

Tyr Asp Lys Val Ile Ile Asn Val Cys Phe Glu Ala Ala Ser Glu Thr
145                 150                 155                 160

Thr Leu Phe Thr Asp His Ile Leu His Gly Ala Asp Ile Ala Ala Lys
                165                 170                 175

Asp Val Glu Ala Ser Arg Pro Ser Phe Lys Thr Ser Thr Gly Phe Phe
            180                 185                 190

Ser Val Ser Met Asn Thr Val Tyr Ser Gln Asn Ser Gln Leu Gln Leu
        195                 200                 205

Met Thr Ser Ile Leu Gly Asp Glu Asp Pro Ala Asn Thr Ile Ile Asp
    210                 215                 220

Pro Ser Lys Gln Leu Tyr Phe Ala Lys Gly His Met Ser Pro Asp Ala
225                 230                 235                 240

Gly Phe Val Thr Ile Ala Ser Gln Asp Ala Thr Tyr Tyr Phe Ile Asn
                245                 250                 255

Ala Leu Pro Gln Trp Gln Ala Phe Asn Asn Gly Asn Trp Lys Tyr Leu
            260                 265                 270

Glu Thr Asn Thr Arg Asn Leu Ala Met Lys Lys Gly Arg Asp Leu Arg
        275                 280                 285
```

```
Val Tyr Ser Gly Gly Trp Asp Val Leu Glu Leu Asp Asp Ile Asn Gly
    290                 295                 300
Asn Pro Val Lys Val Phe Leu Gly Leu Thr Glu Gly Lys Glu Val Val
305                 310                 315                 320
Pro Ala Pro Ala Ile Thr Trp Lys Val Val His Asp Glu Ser Thr Asn
                325                 330                 335
Cys Ala Val Ala Val Gly Val Asn Asn Pro His Leu Thr Ala Ala
                340                 345                 350
Pro Ala Thr Leu Cys Glu Asp Leu Cys Ser Ser Leu Ser Trp Ile Thr
                355                 360                 365
Phe Asp Val Ser Ser Leu Ala Ser Gly Tyr Thr Tyr Arg Cys Ser Val
370                 375                 380
Ala Glu Leu Arg Ala Ser Val Pro His Val Pro Asp Leu Gly Asn Val
385                 390                 395                 400
Cys Leu Leu Thr Asp
            405

<210> SEQ ID NO 23
<211> LENGTH: 114
<212> TYPE: DNA
<213> ORGANISM: homo sapiens

<400> SEQUENCE: 23
agtacgctca agacgacaga agtacgcccg ggcgtactct gcgttgttac cactgctttg     60
gagctccaat tcgccctata gtgagtcgta ttattctgtc gtcttcacgc taca          114

<210> SEQ ID NO 24
<211> LENGTH: 114
<212> TYPE: DNA
<213> ORGANISM: homo sapiens

<400> SEQUENCE: 24
agtacgctca agacgacaga agtacgcccg ggcgtactct gcgttgttac cactgctttg     60
gagctccaat tcgccctgta gtgagtcgta ttattctgtc gtcttcacgc taca          114

<210> SEQ ID NO 25
<211> LENGTH: 10
<212> TYPE: DNA
<213> ORGANISM: homo sapiens

<400> SEQUENCE: 25
gccctgtagt                                                           10

<210> SEQ ID NO 26
<211> LENGTH: 10
<212> TYPE: DNA
<213> ORGANISM: homo sapiens

<400> SEQUENCE: 26
gccctatagt                                                           10

<210> SEQ ID NO 27
<211> LENGTH: 10
<212> TYPE: DNA
<213> ORGANISM: homo sapiens

<400> SEQUENCE: 27
gtgagctaca                                                           10
```

```
<210> SEQ ID NO 28
<211> LENGTH: 18
<212> TYPE: DNA
<213> ORGANISM: homo sapiens

<400> SEQUENCE: 28
aaggggagcc tcaccacg                                                 18

<210> SEQ ID NO 29
<211> LENGTH: 20
<212> TYPE: DNA
<213> ORGANISM: homo sapiens

<400> SEQUENCE: 29
ccacggatct gaagggtgaa                                               20

<210> SEQ ID NO 30
<211> LENGTH: 21
<212> TYPE: DNA
<213> ORGANISM: homo sapiens

<400> SEQUENCE: 30
atggttccca ataaaagtga c                                             21

<210> SEQ ID NO 31
<211> LENGTH: 20
<212> TYPE: DNA
<213> ORGANISM: homo sapiens

<400> SEQUENCE: 31
aatagcactg ggagcattga                                               20

<210> SEQ ID NO 32
<211> LENGTH: 20
<212> TYPE: DNA
<213> ORGANISM: homo sapiens

<400> SEQUENCE: 32
cttgaaggag aaggtgtctg                                               20

<210> SEQ ID NO 33
<211> LENGTH: 21
<212> TYPE: DNA
<213> ORGANISM: homo sapiens

<400> SEQUENCE: 33
aagaaaagct gcgtgatgat g                                             21

<210> SEQ ID NO 34
<211> LENGTH: 10
<212> TYPE: DNA
<213> ORGANISM: homo sapiens

<400> SEQUENCE: 34
tgggcagtgc                                                          10

<210> SEQ ID NO 35
<211> LENGTH: 10
<212> TYPE: DNA
<213> ORGANISM: homo sapiens

<400> SEQUENCE: 35
tggacagtgc                                                          10
```

```
<210> SEQ ID NO 36
<211> LENGTH: 10
<212> TYPE: DNA
<213> ORGANISM: homo sapiens

<400> SEQUENCE: 36
gctcgctgag                                                          10

<210> SEQ ID NO 37
<211> LENGTH: 10
<212> TYPE: DNA
<213> ORGANISM: homo sapiens

<400> SEQUENCE: 37
gcttgctgag                                                          10

<210> SEQ ID NO 38
<211> LENGTH: 10
<212> TYPE: DNA
<213> ORGANISM: homo sapiens

<400> SEQUENCE: 38
tcggctcccg                                                          10

<210> SEQ ID NO 39
<211> LENGTH: 10
<212> TYPE: DNA
<213> ORGANISM: homo sapiens

<400> SEQUENCE: 39
tcgactcccg                                                          10

<210> SEQ ID NO 40
<211> LENGTH: 22
<212> TYPE: DNA
<213> ORGANISM: homo sapiens

<400> SEQUENCE: 40
tactaatctg taagagcaga tc                                            22

<210> SEQ ID NO 41
<211> LENGTH: 22
<212> TYPE: DNA
<213> ORGANISM: homo sapiens

<400> SEQUENCE: 41
gttacttcaa ggacaaaata cc                                            22

<210> SEQ ID NO 42
<211> LENGTH: 10
<212> TYPE: DNA
<213> ORGANISM: homo sapiens

<400> SEQUENCE: 42
aggcgaggaa                                                          10

<210> SEQ ID NO 43
<211> LENGTH: 10
<212> TYPE: DNA
<213> ORGANISM: homo sapiens

<400> SEQUENCE: 43
aggcaaggaa                                                          10
```

```
<210> SEQ ID NO 44
<211> LENGTH: 10
<212> TYPE: DNA
<213> ORGANISM: homo sapiens

<400> SEQUENCE: 44
aggcaaggaa                                                            10

<210> SEQ ID NO 45
<211> LENGTH: 17
<212> TYPE: DNA
<213> ORGANISM: homo sapiens

<400> SEQUENCE: 45
gcggacatgg aggacgt                                                    17

<210> SEQ ID NO 46
<211> LENGTH: 21
<212> TYPE: DNA
<213> ORGANISM: homo sapiens

<400> SEQUENCE: 46
ggcctgcacc tcgccgcggt a                                               21

<210> SEQ ID NO 47
<211> LENGTH: 10
<212> TYPE: DNA
<213> ORGANISM: homo sapiens

<400> SEQUENCE: 47
cgtgcgcggc                                                            10

<210> SEQ ID NO 48
<211> LENGTH: 10
<212> TYPE: DNA
<213> ORGANISM: homo sapiens

<400> SEQUENCE: 48
cgtgtgcggc                                                            10

<210> SEQ ID NO 49
<211> LENGTH: 17
<212> TYPE: DNA
<213> ORGANISM: homo sapiens

<400> SEQUENCE: 49
aggggagcct caccacg                                                    17

<210> SEQ ID NO 50
<211> LENGTH: 20
<212> TYPE: DNA
<213> ORGANISM: homo sapiens

<400> SEQUENCE: 50
ccacggatct gaagggtgaa                                                 20

<210> SEQ ID NO 51
<211> LENGTH: 30
<212> TYPE: DNA
<213> ORGANISM: homo sapiens

<400> SEQUENCE: 51
```

-continued gccctgtagt acacgtacta cgttgttgcc 30

<210> SEQ ID NO 52
<211> LENGTH: 20
<212> TYPE: DNA
<213> ORGANISM: homo sapiens

<400> SEQUENCE: 52
acagctccta ttgataggac 20

<210> SEQ ID NO 53
<211> LENGTH: 10
<212> TYPE: DNA
<213> ORGANISM: homo sapiens

<400> SEQUENCE: 53
gccctgtagt 10

<210> SEQ ID NO 54
<211> LENGTH: 10
<212> TYPE: DNA
<213> ORGANISM: homo sapiens

<400> SEQUENCE: 54
gctcgctgag 10

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
tgggcagtgc tcgcttagtg 20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
cactaagcga gcactgccca 20

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
tgggcagtgc tcgcttagtg 20

<210> SEQ ID NO 58
<211> LENGTH: 7
<212> TYPE: DNA
<213> ORGANISM: Artificial Sequence
<220> FEATURE:
<223> OTHER INFORMATION: synthetic oligonucleotide

<400> SEQUENCE: 58 cgagcac 7

<210> SEQ ID NO 59
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 59 gcgagcac                                                                8

<210> SEQ ID NO 60
<211> LENGTH: 9
<212> TYPE: DNA
<213> ORGANISM: Artificial Sequence
<220> FEATURE:
<223> OTHER INFORMATION: synthetic oligonucleotide

<400> SEQUENCE: 60 gcgagcact                                                               9

<210> SEQ ID NO 61
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 61
agcgagcact                                                              10

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
cactaagcga gcactgccca                                                   20

<210> SEQ ID NO 63
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 63
actcactata cggcgaat                                                     18

<210> SEQ ID NO 64
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 64
gccctatagt                                                              10

<210> SEQ ID NO 65
<211> LENGTH: 18
<212> TYPE: DNA
<213> ORGANISM: Artificial Sequence
<220> FEATURE:

```
-continued

<223> OTHER INFORMATION: synthetic oligonucleotide

<400> SEQUENCE: 65
actcactata ggtcgaat                                                    18

<210> SEQ ID NO 66
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 66
actcactata gggcgaat                                                    18
```